(12) United States Patent
Goodarzi

(10) Patent No.: US 12,398,429 B2
(45) Date of Patent: Aug. 26, 2025

(54) METHODS AND SYSTEMS FOR SEQUENCING POLYNUCLEOTIDES

(71) Applicant: The Regents of the University of California, Oakland, CA (US)

(72) Inventor: Hani Goodarzi, San Francisco, CA (US)

(73) Assignee: The Regents of the University of California

( * ) Notice: Subject to any disclaimer, the term of this patent is extended or adjusted under 35 U.S.C. 154(b) by 0 days.

(21) Appl. No.: 18/429,051

(22) Filed: Jan. 31, 2024

(65) Prior Publication Data

US 2025/0101509 A1    Mar. 27, 2025

Related U.S. Application Data

(63) Continuation of application No. 18/489,807, filed on Oct. 18, 2023, now abandoned, which is a continuation of application No. 16/763,540, filed as application No. PCT/US2018/060113 on Nov. 9, 2018, now abandoned.

(60) Provisional application No. 62/584,899, filed on Nov. 12, 2017.

(51) Int. Cl.
*C12Q 1/6886* (2018.01)
*C12Q 1/48* (2006.01)
*C12Q 1/6806* (2018.01)
*C12Q 1/686* (2018.01)
*C12Q 1/6874* (2018.01)

(52) U.S. Cl.
CPC ............ *C12Q 1/6886* (2013.01); *C12Q 1/485* (2013.01); *C12Q 1/6806* (2013.01); *C12Q 1/686* (2013.01); *C12Q 1/6874* (2013.01); *C12Q 2600/158* (2013.01); *C12Q 2600/16* (2013.01); *C12Q 2600/178* (2013.01); *C12Y 207/07049* (2013.01)

(58) Field of Classification Search
CPC ...... C12Q 1/686; C12Q 1/6805; C12Q 1/485; C12Q 1/6874
See application file for complete search history.

(56) References Cited

U.S. PATENT DOCUMENTS

2008/0076674 A1* 3/2008 Litman ............... C40B 30/04
536/24.31

OTHER PUBLICATIONS

Lo et al, Noncoding RNAs in breast cancer, 2016, Briefings in Functional Genomics, 15(3),200-221. (Year: 2016).*

(Continued)

*Primary Examiner* — Gary Benzion
*Assistant Examiner* — Lisa Horth
(74) *Attorney, Agent, or Firm* — Regents of UCal with Exai

(57) ABSTRACT

The present disclosure relates generally to detection on non-coding RNAS molecules in a sample or diagnosis of subject based upon detection or quantification of non-coding nucleic acid sequences in a sample, specifically to identify and use of molecular biomarkers for cancer including breast cancer.

20 Claims, 32 Drawing Sheets

Specification includes a Sequence Listing.

(56) References Cited

OTHER PUBLICATIONS

Cuk et al. (Int J. Cancer, 2013, 132: 1602-1612).
Argyopoulos et al (PLoS One, 2013, 8(1)(54662): 1-13).
Cheng et al. (Kidney International, 2014, 86: 433-444).
Peng et al. (Forensic Science International: Genetics Supplement Series 5, 2015, e674-e675).
Zhang et al (World J Gastroenterol, 2014, 20(34): 12241-12248).
Mar-Aguilar at al. (Asia Pac J Chin Oncol, 2013, 9(1): Abstract).
Li et al (Cancer Medicine, 2019, 8:7006-7017).
Liao et al. (Molecular Cancer, 2010, 9(198): 1-10).

* cited by examiner

| $P < 10^{-14}$ | T3p Expression | |
|---|---|---|
| | =0 | >0 |
| TCGA Normal | 70 | 34 |
| TCGA BRCA | 237 | 598 |

| $P < 10^{-14}$ | T3p Expression | |
|---|---|---|
| | <0.1 | >0.1 |
| TCGA Normal | 73 | 31 |
| TCGA BRCA | 253 | 582 |

FIG. 4A

```
SEQUENCE LISTING

Sequence total quantity: 212
SEQ ID NO: 1              moltype = DNA  length = 50
FEATURE                   Location/Qualifiers
source                    1..50
                          mol_type = other DNA
                          organism = Homo sapiens
SEQUENCE: 1
ggcggactcg ggactgctgc taaagcgggg ttcctgccgt tccacttggc          50

SEQ ID NO: 2              moltype = DNA  length = 50
FEATURE                   Location/Qualifiers
source                    1..50
                          mol_type = other DNA
                          organism = Homo sapiens
SEQUENCE: 2
gggtggcaga cccagatcct gaggtcctgc ggcttcctcc ccgggggagc          50

SEQ ID NO: 3              moltype = DNA  length = 50
FEATURE                   Location/Qualifiers
source                    1..50
                          mol_type = other DNA
                          organism = Homo sapiens
SEQUENCE: 3
ggcggctggg actggaggac agcggtggcg gaggcgacta gcggcggcgg          50

SEQ ID NO: 4              moltype = DNA  length = 50
FEATURE                   Location/Qualifiers
source                    1..50
                          mol_type = other DNA
                          organism = Homo sapiens
SEQUENCE: 4
gctcgctcgc tccctccctc cgctggtgcg tttagtcagt cagccagcag          50

SEQ ID NO: 5              moltype = DNA  length = 50
FEATURE                   Location/Qualifiers
source                    1..50
                          mol_type = other DNA
                          organism = Homo sapiens
SEQUENCE: 5
gcttccttct ttattttct ctacagctct cctcaccatc tgacacatac           50

SEQ ID NO: 6              moltype = DNA  length = 50
FEATURE                   Location/Qualifiers
source                    1..50
                          mol_type = other DNA
                          organism = Homo sapiens
SEQUENCE: 6
ttttacaagc catttctgag atgggaaact attaggtcag tgcaaaagtg          50

SEQ ID NO: 7              moltype = DNA  length = 50
FEATURE                   Location/Qualifiers
source                    1..50
                          mol_type = other DNA
                          organism = Homo sapiens
SEQUENCE: 7
gtctaagaaa tattttgtg ctttctggcc ttcttttccc accttaggct            50

SEQ ID NO: 8              moltype = DNA  length = 50
```

```
FEATURE                 Location/Qualifiers
source                  1..50
                        mol_type = other DNA
                        organism = Homo sapiens
SEQUENCE: 8
acttccggcg gcggctgagg cggcggccga ggagcggcgg actcgggcg          50

SEQ ID NO: 9            moltype = DNA   length = 50
FEATURE                 Location/Qualifiers
source                  1..50
                        mol_type = other DNA
                        organism = Homo sapiens
SEQUENCE: 9
tcaaacaaaa tactggtttt gttttactga gaggcactgt gggttttgt          50

SEQ ID NO: 10           moltype = DNA   length = 50
FEATURE                 Location/Qualifiers
source                  1..50
                        mol_type = other DNA
                        organism = Homo sapiens
SEQUENCE: 10
agcggcctct gacaccagca cagcaaaccc gccgggatca aagtgtacca          50

SEQ ID NO: 11           moltype = DNA   length = 50
FEATURE                 Location/Qualifiers
source                  1..50
                        mol_type = other DNA
                        organism = Homo sapiens
SEQUENCE: 11
cggtagggcc gctgtatctg ggagtagggg actaagagtc tgagggtcca          50

SEQ ID NO: 12           moltype = DNA   length = 50
FEATURE                 Location/Qualifiers
source                  1..50
                        mol_type = other DNA
                        organism = Homo sapiens
SEQUENCE: 12
tactgaccac cctcacccat gaggctttct ggatcattct ctgaacttta          50

SEQ ID NO: 13           moltype = DNA   length = 50
FEATURE                 Location/Qualifiers
source                  1..50
                        mol_type = other DNA
                        organism = Homo sapiens
SEQUENCE: 13
ttgtacctt ctctcctcga ctgtgaagcg ggccgggacc tgccaggcca           50

SEQ ID NO: 14           moltype = DNA   length = 50
FEATURE                 Location/Qualifiers
source                  1..50
                        mol_type = other DNA
                        organism = Homo sapiens
SEQUENCE: 14
atggggctgg ctggttgtgg gatctggagg catctgggt tggaatgtga           50

SEQ ID NO: 15           moltype = DNA   length = 50
FEATURE                 Location/Qualifiers
source                  1..50
                        mol_type = other DNA
                        organism = Homo sapiens
SEQUENCE: 15
ggctgcttga agtcccggga gtcggtgagg cggctgcagg tccctccctg          50

SEQ ID NO: 16           moltype = DNA   length = 50
FEATURE                 Location/Qualifiers
source                  1..50
                        mol_type = other DNA
                        organism = Homo sapiens
SEQUENCE: 16
ctgtatatgt ttctggagtc ctgagcctga gctaaacaaa agcaggaggc          50

SEQ ID NO: 17           moltype = DNA   length = 50
FEATURE                 Location/Qualifiers
source                  1..50
                        mol_type = other DNA
                        organism = Homo sapiens
SEQUENCE: 17
tctggaagaa gtaatttgct ctatggttct ctggtgtcct gaaaagtgta         50
```

```
SEQ ID NO: 18            moltype = DNA   length = 50
FEATURE                  Location/Qualifiers
source                   1..50
                         mol_type = other DNA
                         organism = Homo sapiens
SEQUENCE: 18
ggttcacagc gggcagggaa agccgcggga agggtactcc aggcgagagg               50

SEQ ID NO: 19            moltype = DNA   length = 50
FEATURE                  Location/Qualifiers
source                   1..50
                         mol_type = other DNA
                         organism = Homo sapiens
SEQUENCE: 19
tggcggagcg aacgggaccg gcccggcttc agagcgcgag gtggagggtg               50

SEQ ID NO: 20            moltype = DNA   length = 50
FEATURE                  Location/Qualifiers
source                   1..50
                         mol_type = other DNA
                         organism = Homo sapiens
SEQUENCE: 20
gcaggaggaa actgctcggg ctgcaagcag tcttccaggc tttgcggctg               50

SEQ ID NO: 21            moltype = DNA   length = 50
FEATURE                  Location/Qualifiers
source                   1..50
                         mol_type = other DNA
                         organism = Homo sapiens
SEQUENCE: 21
cgcaagctgg gttggcagag gacgctggaa cctggctggt cggggagaaa               50

SEQ ID NO: 22            moltype = DNA   length = 50
FEATURE                  Location/Qualifiers
source                   1..50
                         mol_type = other DNA
                         organism = Homo sapiens
SEQUENCE: 22
tgaccacaac atggctgcgg cgcctgggct gctcgtctgg ctgctcgtgc               50

SEQ ID NO: 23            moltype = DNA   length = 150
FEATURE                  Location/Qualifiers
source                   1..150
                         mol_type = other DNA
                         organism = Homo sapiens
SEQUENCE: 23
ggaacatctg aatgctgagg cctagagatc gttcagggtg ttgtaactgg gaacatctga   60
atgctgaggc ctagagatcg ttcagggtgt tgtaactggg aacatctgaa tgctgaggcc   120
tagagatcgt tcagggtgtt gtaactggga                                    150

SEQ ID NO: 24            moltype = DNA   length = 50
FEATURE                  Location/Qualifiers
source                   1..50
                         mol_type = other DNA
                         organism = Homo sapiens
SEQUENCE: 24
tccggagcgc gtggcgggcg tcagcgcggt ggccagcgcg cagaggcggg               50

SEQ ID NO: 25            moltype = DNA   length = 50
FEATURE                  Location/Qualifiers
source                   1..50
                         mol_type = other DNA
                         organism = Homo sapiens
SEQUENCE: 25
gcgtttctgt ttggagagac tcagccatca tgccagaccc gtccaaatcg               50

SEQ ID NO: 26            moltype = DNA   length = 50
FEATURE                  Location/Qualifiers
source                   1..50
                         mol_type = other DNA
                         organism = Homo sapiens
SEQUENCE: 26
tgtttgcaca aatttcctta aaaatcaact tgtactgtag cataagaaaa               50

SEQ ID NO: 27            moltype = DNA   length = 50
FEATURE                  Location/Qualifiers
source                   1..50
                         mol_type = other DNA
                         organism = Homo sapiens
```

-continued

```
SEQUENCE: 27
ctttatggca ctggtagaca aaactatcaa ctgtgttaaa ataattctag          50

SEQ ID NO: 28          moltype = DNA  length = 50
FEATURE                Location/Qualifiers
source                 1..50
                       mol_type = other DNA
                       organism = Homo sapiens
SEQUENCE: 28
ctgcccttat cagttttgac ctgctaggtg cttcacagaa ctttgcttga          50

SEQ ID NO: 29          moltype = DNA  length = 150
FEATURE                Location/Qualifiers
source                 1..150
                       mol_type = other DNA
                       organism = Homo sapiens
SEQUENCE: 29
tcatcatatt atacagaccg aactgttgta taaatttatt tactgctagt cttaagaact   60
gctttcttte gtttgtttgt ttcaatattt tccttctctc tcaattttg gttgaataaa   120
ctagattaca ttcagttggc ctaaggtggt                                    150

SEQ ID NO: 30          moltype = DNA  length = 50
FEATURE                Location/Qualifiers
source                 1..50
                       mol_type = other DNA
                       organism = Homo sapiens
SEQUENCE: 30
ccagcctgag caacatagcg agaccccgtg tctctttttt tttttttttt          50

SEQ ID NO: 31          moltype = DNA  length = 50
FEATURE                Location/Qualifiers
source                 1..50
                       mol_type = other DNA
                       organism = Homo sapiens
SEQUENCE: 31
gtgggaggat cacttgagcc cggaagttca agaccaccct aggcaatata          50

SEQ ID NO: 32          moltype = DNA  length = 50
FEATURE                Location/Qualifiers
source                 1..50
                       mol_type = other DNA
                       organism = Homo sapiens
SEQUENCE: 32
atgaatctaa gagagaatgg aatgtatggg aaaagaaagt tactggaact          50

SEQ ID NO: 33          moltype = DNA  length = 50
FEATURE                Location/Qualifiers
source                 1..50
                       mol_type = other DNA
                       organism = Homo sapiens
SEQUENCE: 33
aataaatatg cattctctta ttggagcagg cagccaggaa tgtagagctc          50

SEQ ID NO: 34          moltype = DNA  length = 50
FEATURE                Location/Qualifiers
source                 1..50
                       mol_type = other DNA
                       organism = Homo sapiens
SEQUENCE: 34
ggactcacgt ggatgacagt ggaggcctcc tggatctcta ggtctcaggg          50

SEQ ID NO: 35          moltype = DNA  length = 50
FEATURE                Location/Qualifiers
source                 1..50
                       mol_type = other DNA
                       organism = Homo sapiens
SEQUENCE: 35
agacacctgc gggagggacc agagcccggt cagggcgagg gggcggaggc          50

SEQ ID NO: 36          moltype = DNA  length = 50
FEATURE                Location/Qualifiers
source                 1..50
                       mol_type = other DNA
                       organism = Homo sapiens
SEQUENCE: 36
tgtcgatttc ctgtagtgaa tcaggcaccg gagtgcaggt tcggggtgg           50

SEQ ID NO: 37          moltype = DNA  length = 50
FEATURE                Location/Qualifiers
```

```
                          -continued source                    1..50
                          mol_type = other DNA
                          organism = Homo sapiens
SEQUENCE: 37
cccccccgcca ctgctgaatt tgactggcta taaaaataaa ataaaatcca              50

SEQ ID NO: 38             moltype = DNA   length = 50
FEATURE                   Location/Qualifiers
source                    1..50
                          mol_type = other DNA
                          organism = Homo sapiens
SEQUENCE: 38
tccttgatgt ataaaaatta acaaaaataa ttttacttgt ggcaatgttc              50

SEQ ID NO: 39             moltype = DNA   length = 350
FEATURE                   Location/Qualifiers
source                    1..350
                          mol_type = other DNA
                          organism = Homo sapiens
SEQUENCE: 39
cactgccacc cagaagactg tggatggccc ctccgggaaa ctgtggcgtg atggccgcgg    60
ggctctccag aacatcatcc ctgcctctac tggcgctgcc aaggctgtgg gcaaggtcat  120
ccctgagctg aacgggaagc tcactggcat ggccttccgt gtccccactg ccaacgtgtc  180
agtggtggac ctgacctgcc gtctagaaaa acctgccaaa tatgatgaca tcaagaaggt  240
ggtgaagcag gcgtcggagg gcccctcaa gggcatcctg ggctacactg agcaccaggt  300
ggtctcctct gacttcaaca gcgacaccca ctcctccacc tttgacgctg             350

SEQ ID NO: 40             moltype = DNA   length = 50
FEATURE                   Location/Qualifiers
source                    1..50
                          mol_type = other DNA
                          organism = Homo sapiens
SEQUENCE: 40
acttttttt ttttttttta gcagtttgag ttggtgtagt gtattcttgg               50

SEQ ID NO: 41             moltype = DNA   length = 100
FEATURE                   Location/Qualifiers
source                    1..100
                          mol_type = other DNA
                          organism = Homo sapiens
SEQUENCE: 41
tatgaggagc tgcagagcct ggctgggaag cacggggatg acctgcggcg cacaaagact    60
gagatctctg agatgaaccg gaacatcagc cggctccagg                         100

SEQ ID NO: 42             moltype = DNA   length = 50
FEATURE                   Location/Qualifiers
source                    1..50
                          mol_type = other DNA
                          organism = Homo sapiens
SEQUENCE: 42
tggacccaaa ctgaggagcc cggagctgcc gctgggggat cggggccggg               50

SEQ ID NO: 43             moltype = DNA   length = 50
FEATURE                   Location/Qualifiers
source                    1..50
                          mol_type = other DNA
                          organism = Homo sapiens
SEQUENCE: 43
agggccgggc gggacgggaa acgttagggc agcggccccc ggggtgaggg               50

SEQ ID NO: 44             moltype = DNA   length = 50
FEATURE                   Location/Qualifiers
source                    1..50
                          mol_type = other DNA
                          organism = Homo sapiens
SEQUENCE: 44
cgtagcccca gctgaggcag gagaattgct tgagcccagg aactggaggc               50

SEQ ID NO: 45             moltype = DNA   length = 50
FEATURE                   Location/Qualifiers
source                    1..50
                          mol_type = other DNA
                          organism = Homo sapiens
SEQUENCE: 45
gccagcccag aacactggtc tcgggcccga aagacctcc ttttccagg                 50

SEQ ID NO: 46             moltype = DNA   length = 50
FEATURE                   Location/Qualifiers
source                    1..50
```

```
                        mol_type = other DNA
                        organism = Homo sapiens
SEQUENCE: 46
cttgttacaa ctgagtccgg gttggaggag gtgtggggcc gctgccgcca            50

SEQ ID NO: 47           moltype = DNA  length = 50
FEATURE                 Location/Qualifiers
source                  1..50
                        mol_type = other DNA
                        organism = Homo sapiens
SEQUENCE: 47
cccccacaac cgcgcctggc tacttttgt attttagta gagacagggt              50

SEQ ID NO: 48           moltype = DNA  length = 50
FEATURE                 Location/Qualifiers
source                  1..50
                        mol_type = other DNA
                        organism = Homo sapiens
SEQUENCE: 48
aatgtcaagt tagaaaaaat gttgtagttt catgttgttg gtttgcaaat            50

SEQ ID NO: 49           moltype = DNA  length = 50
FEATURE                 Location/Qualifiers
source                  1..50
                        mol_type = other DNA
                        organism = Homo sapiens
SEQUENCE: 49
tgggtctgaa ttccagtcta tcacttgtta tgtgacctcg gatgaatcac            50

SEQ ID NO: 50           moltype = DNA  length = 50
FEATURE                 Location/Qualifiers
source                  1..50
                        mol_type = other DNA
                        organism = Homo sapiens
SEQUENCE: 50
tgaaatgctt aggaccaaaa gtgtttcaga tttcagattt ttaaaatatt            50

SEQ ID NO: 51           moltype = DNA  length = 50
FEATURE                 Location/Qualifiers
source                  1..50
                        mol_type = other DNA
                        organism = Homo sapiens
SEQUENCE: 51
taagccgtgg aaaatgttct tgatcatttg cagttaagga ctttaaataa            50

SEQ ID NO: 52           moltype = DNA  length = 50
FEATURE                 Location/Qualifiers
source                  1..50
                        mol_type = other DNA
                        organism = Homo sapiens
SEQUENCE: 52
ttgtcagtgc cgcagccccg accgccggga gctcgaaccc gagccggggc            50

SEQ ID NO: 53           moltype = DNA  length = 50
FEATURE                 Location/Qualifiers
source                  1..50
                        mol_type = other DNA
                        organism = Homo sapiens
SEQUENCE: 53
ttgtgggtaa gttctctctg agatttggga gattcataaa tttgtgtttt            50

SEQ ID NO: 54           moltype = DNA  length = 50
FEATURE                 Location/Qualifiers
source                  1..50
                        mol_type = other DNA
                        organism = Homo sapiens
SEQUENCE: 54
cactcctgac atcatctgat aaagaaagt cttcagccga atttaattta             50

SEQ ID NO: 55           moltype = DNA  length = 50
FEATURE                 Location/Qualifiers
source                  1..50
                        mol_type = other DNA
                        organism = Homo sapiens
SEQUENCE: 55
tgagccgctt ggcgtcgtgg tatctgagaa gctgctctat tcctttcctt            50

SEQ ID NO: 56           moltype = DNA  length = 50
FEATURE                 Location/Qualifiers
```

```
source                          1..50
                                mol_type = other DNA
                                organism = Homo sapiens
SEQUENCE: 56
ctcagctgcg cccagagcct tcggccggac ctgaaaaagc gagagggaga                    50

SEQ ID NO: 57                   moltype = DNA   length = 50
FEATURE                         Location/Qualifiers
source                          1..50
                                mol_type = other DNA
                                organism = Homo sapiens
SEQUENCE: 57
tctgtcacct gactcggctc aaacatggct gcgctgagag ctctattgct                    50

SEQ ID NO: 58                   moltype = DNA   length = 50
FEATURE                         Location/Qualifiers
source                          1..50
                                mol_type = other DNA
                                organism = Homo sapiens
SEQUENCE: 58
gttctgagat tcactactgg tatggcctgg agaatgcaga ccctgtccag                    50

SEQ ID NO: 59                   moltype = DNA   length = 50
FEATURE                         Location/Qualifiers
source                          1..50
                                mol_type = other DNA
                                organism = Homo sapiens
SEQUENCE: 59
ccaaaactat tcatttgcat tgtagtagtt tgtacagtca tatgtaaaac                    50

SEQ ID NO: 60                   moltype = DNA   length = 50
FEATURE                         Location/Qualifiers
source                          1..50
                                mol_type = other DNA
                                organism = Homo sapiens
SEQUENCE: 60
gtcggggaag cgttctaggc tgggcgcgcg gtctcgggtc aggtgtggcg                    50

SEQ ID NO: 61                   moltype = DNA   length = 50
FEATURE                         Location/Qualifiers
source                          1..50
                                mol_type = other DNA
                                organism = Homo sapiens
SEQUENCE: 61
tatgtcctgg tgaggctcca gcaagcagtg aagccccacc tgtccatccc                    50

SEQ ID NO: 62                   moltype = DNA   length = 50
FEATURE                         Location/Qualifiers
source                          1..50
                                mol_type = other DNA
                                organism = Homo sapiens
SEQUENCE: 62
catgttttgt tacaggttgt agagtatttg cagaaggaaa ccatttctgg                    50

SEQ ID NO: 63                   moltype = DNA   length = 50
FEATURE                         Location/Qualifiers
source                          1..50
                                mol_type = other DNA
                                organism = Homo sapiens
SEQUENCE: 63
gggacacagc gggacaggtg agaagctggg cgcggcctct actggtctgc                    50

SEQ ID NO: 64                   moltype = DNA   length = 50
FEATURE                         Location/Qualifiers
source                          1..50
                                mol_type = other DNA
                                organism = Homo sapiens
SEQUENCE: 64
tttatcccac tcctgacagt ttatcccact cttgacactt ccccttgagc                    50

SEQ ID NO: 65                   moltype = DNA   length = 50
FEATURE                         Location/Qualifiers
source                          1..50
                                mol_type = other DNA
                                organism = Homo sapiens
SEQUENCE: 65
acaccaggtc tcctggcctt gctgactccc agtccaggga gatggaggct                    50

SEQ ID NO: 66                   moltype = DNA   length = 50
```

```
FEATURE                 Location/Qualifiers
source                  1..50
                        mol_type = other DNA
                        organism = Homo sapiens
SEQUENCE: 66
atatggtgac ctcctgggag cgggggacca ccaggttgcc taaggatggg              50

SEQ ID NO: 67           moltype = DNA  length = 250
FEATURE                 Location/Qualifiers
source                  1..250
                        mol_type = other DNA
                        organism = Homo sapiens
SEQUENCE: 67
caccagcccg gaggggcagg tctcggtcta gaacacctgc taggcgcaga tctaggaccc   60
gatcaccagt acgacgcagg tctcgtagta gatcaccagc caggagaagt ggcaggtcac  120
gctctagaac cccagctaga cgtggccgct cacgctccag aacccagcc agacgtggcc   180
gctcacgctc tagaacccca gctagacgca gtggtcgctc acgctccaga acaccagcca  240
ggagagggag                                                         250

SEQ ID NO: 68           moltype = DNA  length = 50
FEATURE                 Location/Qualifiers
source                  1..50
                        mol_type = other DNA
                        organism = Homo sapiens
SEQUENCE: 68
tggctctgta cctggacagg gctgcggtag gccagcggtg ggctggcggt              50

SEQ ID NO: 69           moltype = DNA  length = 50
FEATURE                 Location/Qualifiers
source                  1..50
                        mol_type = other DNA
                        organism = Homo sapiens
SEQUENCE: 69
ctgcaatatc tgattacatt gatgaattcc gttgtattgt atgtgtgaat              50

SEQ ID NO: 70           moltype = DNA  length = 50
FEATURE                 Location/Qualifiers
source                  1..50
                        mol_type = other DNA
                        organism = Homo sapiens
SEQUENCE: 70
attagaatga gtagtagtgt ctgggtgcag tgactcatgc cccattgaaa              50

SEQ ID NO: 71           moltype = DNA  length = 50
FEATURE                 Location/Qualifiers
source                  1..50
                        mol_type = other DNA
                        organism = Homo sapiens
SEQUENCE: 71
tgagcccagg aactggaggc tgcagtgagc tatgactgtt ccacttcact              50

SEQ ID NO: 72           moltype = DNA  length = 50
FEATURE                 Location/Qualifiers
source                  1..50
                        mol_type = other DNA
                        organism = Homo sapiens
SEQUENCE: 72
gtcgcagcca ccggtcacct cagctgtgaa ccatgtagga gccgtctggg              50

SEQ ID NO: 73           moltype = DNA  length = 50
FEATURE                 Location/Qualifiers
source                  1..50
                        mol_type = other DNA
                        organism = Homo sapiens
SEQUENCE: 73
cctcgtgaac tcagaagtta gttttcgtct ctggaccttt ttataatcgg              50

SEQ ID NO: 74           moltype = DNA  length = 50
FEATURE                 Location/Qualifiers
source                  1..50
                        mol_type = other DNA
                        organism = Homo sapiens
SEQUENCE: 74
ccatcatgtt ctttattatt gtgattgaga cctttctgtg ggccaggcat              50

SEQ ID NO: 75           moltype = DNA  length = 50
FEATURE                 Location/Qualifiers
source                  1..50
                        mol_type = other DNA
```

```
                            organism = Homo sapiens
SEQUENCE: 75
tgtcgggccg cggcggcgct tggcagccag gagctctgca ttgaaggcac                50

SEQ ID NO: 76           moltype = DNA  length = 50
FEATURE                 Location/Qualifiers
source                  1..50
                        mol_type = other DNA
                        organism = Homo sapiens
SEQUENCE: 76
tgccaggggc actgccttct cacagctggc cttgccccgt ccaccctgtg                50

SEQ ID NO: 77           moltype = DNA  length = 50
FEATURE                 Location/Qualifiers
source                  1..50
                        mol_type = other DNA
                        organism = Homo sapiens
SEQUENCE: 77
gtgctactcg ctcgaacccg ccgggcgaag gaagcacttc ccatgctctc                50

SEQ ID NO: 78           moltype = DNA  length = 50
FEATURE                 Location/Qualifiers
source                  1..50
                        mol_type = other DNA
                        organism = Homo sapiens
SEQUENCE: 78
agtggactca ggcatcaaag aagtggccaa cgtgtgcaac cagagcctga                50

SEQ ID NO: 79           moltype = DNA  length = 50
FEATURE                 Location/Qualifiers
source                  1..50
                        mol_type = other DNA
                        organism = Homo sapiens
SEQUENCE: 79
attcagccgt atcagtgaag agtgaagcac tgcactcttt aaggataggg                50

SEQ ID NO: 80           moltype = DNA  length = 100
FEATURE                 Location/Qualifiers
source                  1..100
                        mol_type = other DNA
                        organism = Homo sapiens
SEQUENCE: 80
agcacaaata tggtgacctc ctgggagcgg gggaccacca ggttgcctaa ggaggggtga    60
accagggcag gtcggaaatg gagcatgtca aaactcccgc                          100

SEQ ID NO: 81           moltype = DNA  length = 50
FEATURE                 Location/Qualifiers
source                  1..50
                        mol_type = other DNA
                        organism = Homo sapiens
SEQUENCE: 81
ccttggatcc ggcctcccgc ccagtgcctt tggtcgccgg ctgccgcacc                50

SEQ ID NO: 82           moltype = DNA  length = 50
FEATURE                 Location/Qualifiers
source                  1..50
                        mol_type = other DNA
                        organism = Homo sapiens
SEQUENCE: 82
ccctgagctg cccttgcgtt cagttggaag ccacgcaaaa tgaactgaac                50

SEQ ID NO: 83           moltype = DNA  length = 50
FEATURE                 Location/Qualifiers
source                  1..50
                        mol_type = other DNA
                        organism = Homo sapiens
SEQUENCE: 83
gcgtgagagg cgcgcggcgg cgcagtgaac agtctccttc cacaaaacca                50

SEQ ID NO: 84           moltype = DNA  length = 50
FEATURE                 Location/Qualifiers
source                  1..50
                        mol_type = other DNA
                        organism = Homo sapiens
SEQUENCE: 84
gcagccctgg cagtgcctcc ggcgctttgc cctggcctgg tgggagagga                50

SEQ ID NO: 85           moltype = DNA  length = 50
FEATURE                 Location/Qualifiers
```

```
source                  1..50
                        mol_type = other DNA
                        organism = Homo sapiens
SEQUENCE: 85
tgacacctag cggagcgatg cccaaccagg cgcagatgcg gatcctgaaa        50

SEQ ID NO: 86           moltype = DNA   length = 100
FEATURE                 Location/Qualifiers
source                  1..100
                        mol_type = other DNA
                        organism = Homo sapiens
SEQUENCE: 86
tccccctggac ccgcccccat ctgcccaaga taattttagt ttccttgggc ctggaatctg    60
gacacacagg gctcccccc gcctctgact tctctgtccg                           100

SEQ ID NO: 87           moltype = DNA   length = 50
FEATURE                 Location/Qualifiers
source                  1..50
                        mol_type = other DNA
                        organism = Homo sapiens
SEQUENCE: 87
acatcctggt ggtagagggg aagggaggag gtcagacctg tcactctcct        50

SEQ ID NO: 88           moltype = DNA   length = 50
FEATURE                 Location/Qualifiers
source                  1..50
                        mol_type = other DNA
                        organism = Homo sapiens
SEQUENCE: 88
ccaaaatggc gatgcctacc acctagaact ggattgtgcg gtaggcttaa        50

SEQ ID NO: 89           moltype = DNA   length = 50
FEATURE                 Location/Qualifiers
source                  1..50
                        mol_type = other DNA
                        organism = Homo sapiens
SEQUENCE: 89
taaccggctg gccgggcgga gctggcagca tttgattgtg gcttgggacg        50

SEQ ID NO: 90           moltype = DNA   length = 50
FEATURE                 Location/Qualifiers
source                  1..50
                        mol_type = other DNA
                        organism = Homo sapiens
SEQUENCE: 90
gaatcctgaa caaacaatct gatctagctt tggcctctct gctccccaat        50

SEQ ID NO: 91           moltype = DNA   length = 50
FEATURE                 Location/Qualifiers
source                  1..50
                        mol_type = other DNA
                        organism = Homo sapiens
SEQUENCE: 91
cgccacactc tgggcacggc gtgggctggg acatttggaa taaacggatc        50

SEQ ID NO: 92           moltype = DNA   length = 50
FEATURE                 Location/Qualifiers
source                  1..50
                        mol_type = other DNA
                        organism = Homo sapiens
SEQUENCE: 92
cgcgcgtcgg ccgcgctcag cggcagagcg gagcggagct gtgaggcgcc        50

SEQ ID NO: 93           moltype = DNA   length = 50
FEATURE                 Location/Qualifiers
source                  1..50
                        mol_type = other DNA
                        organism = Homo sapiens
SEQUENCE: 93
tagtgtgcgg agaggggcgc ggggtggaat tgctgcggga agtgggaaac        50

SEQ ID NO: 94           moltype = DNA   length = 50
FEATURE                 Location/Qualifiers
source                  1..50
                        mol_type = other DNA
                        organism = Homo sapiens
SEQUENCE: 94
gcggctgaag gcgatccgca gtgaggcccc agccattcgg attgagcctt        50
```

```
SEQ ID NO: 95            moltype = DNA   length = 50
FEATURE                  Location/Qualifiers
source                   1..50
                         mol_type = other DNA
                         organism = Homo sapiens
SEQUENCE: 95
gcagcgctgg aggaagaatt cacgttgtct tcggtagtcc tgagcgccgg                 50

SEQ ID NO: 96            moltype = DNA   length = 50
FEATURE                  Location/Qualifiers
source                   1..50
                         mol_type = other DNA
                         organism = Homo sapiens
SEQUENCE: 96
ggcctgtcgg gtcagggcgg ttcgcgggtg ctgtcagagc tgggccgggg                 50

SEQ ID NO: 97            moltype = DNA   length = 50
FEATURE                  Location/Qualifiers
source                   1..50
                         mol_type = other DNA
                         organism = Homo sapiens
SEQUENCE: 97
atggctgccc ccgcagtgaa ggttgcccga ggatggtcgg gcctggcgtt                 50

SEQ ID NO: 98            moltype = DNA   length = 50
FEATURE                  Location/Qualifiers
source                   1..50
                         mol_type = other DNA
                         organism = Homo sapiens
SEQUENCE: 98
gggcagaggc agtgtgggct gatgatgtgc tttggccttc tcgggactgt                 50

SEQ ID NO: 99            moltype = DNA   length = 50
FEATURE                  Location/Qualifiers
source                   1..50
                         mol_type = other DNA
                         organism = Homo sapiens
SEQUENCE: 99
ctggcctggc aggtgacggt gctggatgtg gcctttttgc cttttctaaa                 50

SEQ ID NO: 100           moltype = DNA   length = 50
FEATURE                  Location/Qualifiers
source                   1..50
                         mol_type = other DNA
                         organism = Homo sapiens
SEQUENCE: 100
tttccttaac attcttcctc ccctgcctgg cccagtcctt atccctgct                  50

SEQ ID NO: 101           moltype = DNA   length = 200
FEATURE                  Location/Qualifiers
source                   1..200
                         mol_type = other DNA
                         organism = Homo sapiens
SEQUENCE: 101
aagaaaatag acaatacact tatctggctg gggagatacc atgatcatga aggtggttct      60
cagagtgagg ctcatccatt gcactttggt tgtgctgacc cctgtgattt ccccaaatgc     120
agaatttgta gtagtgaggg actgtgttcg tgctttcccc tgtcattttt tgtcctaaga    180
gatcatagtg tgaagtttat                                                  200

SEQ ID NO: 102           moltype = DNA   length = 100
FEATURE                  Location/Qualifiers
source                   1..100
                         mol_type = other DNA
                         organism = Homo sapiens
SEQUENCE: 102
actgccatga agctctgcag aagaaagatc tggaagtggg agacactttc actatatata      60
gtggctccca cttccagatc tttctctctg tatatatagt                            100

SEQ ID NO: 103           moltype = DNA   length = 50
FEATURE                  Location/Qualifiers
source                   1..50
                         mol_type = other DNA
                         organism = Homo sapiens
SEQUENCE: 103
cattggtgat taaggcttca acatacaaat ttcgggggggg acaaaaacat                50

SEQ ID NO: 104           moltype = DNA   length = 50
FEATURE                  Location/Qualifiers
source                   1..50
```

```
                        mol_type = other DNA
                        organism = Homo sapiens
SEQUENCE: 104
gcggccgcca cgcgacgcct ggctgggccc gcaccggaga ggcgtctcgg          50

SEQ ID NO: 105          moltype = DNA  length = 50
FEATURE                 Location/Qualifiers
source                  1..50
                        mol_type = other DNA
                        organism = Homo sapiens
SEQUENCE: 105
ccctttcgcc acagagcgcg cggaggacaa ggtgaccaga ggttccccag          50

SEQ ID NO: 106          moltype = DNA  length = 50
FEATURE                 Location/Qualifiers
source                  1..50
                        mol_type = other DNA
                        organism = Homo sapiens
SEQUENCE: 106
agttgcacgg cggcgtgtgc gtttcctagt tgtctggtgc tgctatatag          50

SEQ ID NO: 107          moltype = DNA  length = 50
FEATURE                 Location/Qualifiers
source                  1..50
                        mol_type = other DNA
                        organism = Homo sapiens
SEQUENCE: 107
tcagacatga cattcagact gaggtcctca aaactgaggg gcattttctg          50

SEQ ID NO: 108          moltype = DNA  length = 50
FEATURE                 Location/Qualifiers
source                  1..50
                        mol_type = other DNA
                        organism = Homo sapiens
SEQUENCE: 108
aggctgtaaa gagggcgcta cccagaggtg catctgcagg aaaagcccac          50

SEQ ID NO: 109          moltype = DNA  length = 50
FEATURE                 Location/Qualifiers
source                  1..50
                        mol_type = other DNA
                        organism = Homo sapiens
SEQUENCE: 109
atataggaaa gaaccacagg tagtttcatg tggttggagg acagagggaa          50

SEQ ID NO: 110          moltype = DNA  length = 50
FEATURE                 Location/Qualifiers
source                  1..50
                        mol_type = other DNA
                        organism = Homo sapiens
SEQUENCE: 110
ggcaggcggg ccgcggcggc ggcgggcagc ggacgggcgg actgacgggc          50

SEQ ID NO: 111          moltype = DNA  length = 50
FEATURE                 Location/Qualifiers
source                  1..50
                        mol_type = other DNA
                        organism = Homo sapiens
SEQUENCE: 111
agtcctagct acttgagaga ctcagctggg atgatcactt gagcccagga          50

SEQ ID NO: 112          moltype = DNA  length = 50
FEATURE                 Location/Qualifiers
source                  1..50
                        mol_type = other DNA
                        organism = Homo sapiens
SEQUENCE: 112
agggcagctc gccccgcgga gtccgggctg aaccacactg cgcggccgcg          50

SEQ ID NO: 113          moltype = DNA  length = 50
FEATURE                 Location/Qualifiers
source                  1..50
                        mol_type = other DNA
                        organism = Homo sapiens
SEQUENCE: 113
aggtagtgag ttatctcaat tgattgttcg ctttcagtta cagattaagc          50

SEQ ID NO: 114          moltype = DNA  length = 50
FEATURE                 Location/Qualifiers
```

```
source                   1..50
                         mol_type = other DNA
                         organism = Homo sapiens
SEQUENCE: 114
tgctgttctc caaccagtgc ttatgctgca ggcaattttg ttgttcagaa            50

SEQ ID NO: 115           moltype = DNA  length = 50
FEATURE                  Location/Qualifiers
source                   1..50
                         mol_type = other DNA
                         organism = Homo sapiens
SEQUENCE: 115
ctaatcagac gttgctgaag tattgttttt caatgatgat tgactgagaa            50

SEQ ID NO: 116           moltype = DNA  length = 50
FEATURE                  Location/Qualifiers
source                   1..50
                         mol_type = other DNA
                         organism = Homo sapiens
SEQUENCE: 116
ccttctgtcc cctgctccct tgttccccag tccctgtgt catcaagatg             50

SEQ ID NO: 117           moltype = DNA  length = 150
FEATURE                  Location/Qualifiers
source                   1..150
                         mol_type = other DNA
                         organism = Homo sapiens
SEQUENCE: 117
ctcaccaagc aagtgtcgtg gggcttgctg gcttgcaccg tgactcactc tcactaagca 60
agtgtcgtgg ggcttgctgg cttgcaccgt gactcactct cactaagcaa gtgtcgtggg 120
gcttgctggc ttgcaccgtg actccctctc                                  150

SEQ ID NO: 118           moltype = DNA  length = 50
FEATURE                  Location/Qualifiers
source                   1..50
                         mol_type = other DNA
                         organism = Homo sapiens
SEQUENCE: 118
cgaggcgaca gctcgggctc tggagccggg aggcgagaac gaggagggag             50

SEQ ID NO: 119           moltype = DNA  length = 50
FEATURE                  Location/Qualifiers
source                   1..50
                         mol_type = other DNA
                         organism = Homo sapiens
SEQUENCE: 119
ttccgggctc cgggctctgg gtggcggcgg ctgtgagcgg cggcactgcg             50

SEQ ID NO: 120           moltype = DNA  length = 50
FEATURE                  Location/Qualifiers
source                   1..50
                         mol_type = other DNA
                         organism = Homo sapiens
SEQUENCE: 120
gagtctgaga tcagtctggg ccacatagcg agaccccgtc tctatgttaa             50

SEQ ID NO: 121           moltype = DNA  length = 50
FEATURE                  Location/Qualifiers
source                   1..50
                         mol_type = other DNA
                         organism = Homo sapiens
SEQUENCE: 121
gttcaagacc agccttggca atatagcgag accccgtctc tacaaaaaca             50

SEQ ID NO: 122           moltype = DNA  length = 50
FEATURE                  Location/Qualifiers
source                   1..50
                         mol_type = other DNA
                         organism = Homo sapiens
SEQUENCE: 122
aaaagcatat atacctctga ccagtgacgt ggaataggca tgagacgagt             50

SEQ ID NO: 123           moltype = DNA  length = 50
FEATURE                  Location/Qualifiers
source                   1..50
                         mol_type = other DNA
                         organism = Homo sapiens
SEQUENCE: 123
ttacaaattt gactcttgaa tggcaaaata atgttagtat gtagaaggtt             50
```

```
SEQ ID NO: 124          moltype = DNA   length = 150
FEATURE                 Location/Qualifiers
source                  1..150
                        mol_type = other DNA
                        organism = Homo sapiens
SEQUENCE: 124
acgactcctg gtttgccaca agcccggcct ctgtagtgag agagctgtga ctgcgtttcc    60
agctccttga aggcagagag actcctgcct ttcggggcgg gcgggctgga acaaagacac   120
caacggggcc acctcggaaa gtcttttga                                     150

SEQ ID NO: 125          moltype = DNA   length = 50
FEATURE                 Location/Qualifiers
source                  1..50
                        mol_type = other DNA
                        organism = Homo sapiens
SEQUENCE: 125
atggcggcca ccatgaagaa ggcggtgagt ggggagctcg gggctctgga               50

SEQ ID NO: 126          moltype = DNA   length = 100
FEATURE                 Location/Qualifiers
source                  1..100
                        mol_type = other DNA
                        organism = Homo sapiens
SEQUENCE: 126
aacaccaaga gcagctctga gatcatgctg gccctacgcg aattgagttt ctgtggccta    60
attggatttg gagaacgcct tccctggccc cttttcctca                         100

SEQ ID NO: 127          moltype = DNA   length = 50
FEATURE                 Location/Qualifiers
source                  1..50
                        mol_type = other DNA
                        organism = Homo sapiens
SEQUENCE: 127
aacggcgcgc cggctgtggc cggcgcagag tagtgctcgg gccgggggtc               50

SEQ ID NO: 128          moltype = DNA   length = 50
FEATURE                 Location/Qualifiers
source                  1..50
                        mol_type = other DNA
                        organism = Homo sapiens
SEQUENCE: 128
tgagattggt agacatatga cactggtaga attagtttga acatctgtgt               50

SEQ ID NO: 129          moltype = DNA   length = 50
FEATURE                 Location/Qualifiers
source                  1..50
                        mol_type = other DNA
                        organism = Homo sapiens
SEQUENCE: 129
tgtgggtcct ctgctctggc aacaggcaga gcactgcttt agagcctctg               50

SEQ ID NO: 130          moltype = DNA   length = 50
FEATURE                 Location/Qualifiers
source                  1..50
                        mol_type = other DNA
                        organism = Homo sapiens
SEQUENCE: 130
ttggagagtg catccggccc ggtacttgtg atcggaggag agccggatcg               50

SEQ ID NO: 131          moltype = DNA   length = 50
FEATURE                 Location/Qualifiers
source                  1..50
                        mol_type = other DNA
                        organism = Homo sapiens
SEQUENCE: 131
tggcgccaga actagtggcg ggctgaggac gccgtacccc tcggaaggca               50

SEQ ID NO: 132          moltype = DNA   length = 50
FEATURE                 Location/Qualifiers
source                  1..50
                        mol_type = other DNA
                        organism = Homo sapiens
SEQUENCE: 132
cttggcaaca tagcgagacc ccgtctctac aaaaaaattt aaaaattagc               50

SEQ ID NO: 133          moltype = DNA   length = 50
FEATURE                 Location/Qualifiers
source                  1..50
```

```
                        mol_type = other DNA
                        organism = Homo sapiens
SEQUENCE: 133
ccacgaggac tttaaagaag acctgaagaa gttccgcacc aagagccgga              50

SEQ ID NO: 134          moltype = DNA  length = 50
FEATURE                 Location/Qualifiers
source                  1..50
                        mol_type = other DNA
                        organism = Homo sapiens
SEQUENCE: 134
aggctgctaa gtcatcctgg cagcattgcc acatgagccc catgcggtgc              50

SEQ ID NO: 135          moltype = DNA  length = 50
FEATURE                 Location/Qualifiers
source                  1..50
                        mol_type = other DNA
                        organism = Homo sapiens
SEQUENCE: 135
gtgaagatgc tgctggaatt gtccgaggag cataaggaac acctggcctt              50

SEQ ID NO: 136          moltype = DNA  length = 50
FEATURE                 Location/Qualifiers
source                  1..50
                        mol_type = other DNA
                        organism = Homo sapiens
SEQUENCE: 136
tgagctgtgg gacgtgcacc caggactcgg ctcacacatg cagttcgctt              50

SEQ ID NO: 137          moltype = DNA  length = 50
FEATURE                 Location/Qualifiers
source                  1..50
                        mol_type = other DNA
                        organism = Homo sapiens
SEQUENCE: 137
cactgctgta gatgggcggt ctgcgagcgg agttaccgag ttttactccg              50

SEQ ID NO: 138          moltype = DNA  length = 50
FEATURE                 Location/Qualifiers
source                  1..50
                        mol_type = other DNA
                        organism = Homo sapiens
SEQUENCE: 138
ccctggatgc ctgccccttg aatgggggtc aggctgtgca tacattgtga              50

SEQ ID NO: 139          moltype = DNA  length = 50
FEATURE                 Location/Qualifiers
source                  1..50
                        mol_type = other DNA
                        organism = Homo sapiens
SEQUENCE: 139
cagtctgcgc agggactggc gggactgcgc ggcggcgact acagacgtgt              50

SEQ ID NO: 140          moltype = DNA  length = 250
FEATURE                 Location/Qualifiers
source                  1..250
                        mol_type = other DNA
                        organism = Homo sapiens
SEQUENCE: 140
gggatgtgag ggcgatctgg ctgcgacatc tgtcacgcca ttgattgcca gggttgattc    60
ggttgatctt gctggctaga cgggtgtccc cttcctccct cactgctcca catgcgtccc   120
tcccaaagct gcatgctcca ttgaccatcc ccaacagagg aggaccggtc ttcggtcaag   180
ggtatatgag tagctgcact cccctgctag aacctccaaa caagctctca aggtccaaat   240
gacactgggg                                                         250

SEQ ID NO: 141          moltype = DNA  length = 50
FEATURE                 Location/Qualifiers
source                  1..50
                        mol_type = other DNA
                        organism = Homo sapiens
SEQUENCE: 141
gcttaaagga aagcaaaagc tgtgttgaga gaataaaaca gggataagtc              50

SEQ ID NO: 142          moltype = DNA  length = 50
FEATURE                 Location/Qualifiers
source                  1..50
                        mol_type = other DNA
                        organism = Homo sapiens
SEQUENCE: 142
```

```
aaaatgccta tttaaattac tatttcatta tttttctcaa aagtgtgaaa              50

SEQ ID NO: 143          moltype = DNA   length = 50
FEATURE                 Location/Qualifiers
source                  1..50
                        mol_type = other DNA
                        organism = Homo sapiens
SEQUENCE: 143
cccaggaact ggaggctgca gtgagctatg attgcaatta cactccagcc              50

SEQ ID NO: 144          moltype = DNA   length = 50
FEATURE                 Location/Qualifiers
source                  1..50
                        mol_type = other DNA
                        organism = Homo sapiens
SEQUENCE: 144
tggggagagg aggcgagagg ctctccttcc ccgcttcccc cctaggggtt              50

SEQ ID NO: 145          moltype = DNA   length = 50
FEATURE                 Location/Qualifiers
source                  1..50
                        mol_type = other DNA
                        organism = Homo sapiens
SEQUENCE: 145
gactgcagtc ctgagaccct ataacctgta tgactgagag agtgaaacta              50

SEQ ID NO: 146          moltype = DNA   length = 50
FEATURE                 Location/Qualifiers
source                  1..50
                        mol_type = other DNA
                        organism = Homo sapiens
SEQUENCE: 146
gaaaaacccc ccaaacctta aaaatgtaga atctctcagc taatctatat              50

SEQ ID NO: 147          moltype = DNA   length = 50
FEATURE                 Location/Qualifiers
source                  1..50
                        mol_type = other DNA
                        organism = Homo sapiens
SEQUENCE: 147
cagggcttcg gcctccggcg tcgggaaatg gcggcggggg gcaggatgga              50

SEQ ID NO: 148          moltype = DNA   length = 50
FEATURE                 Location/Qualifiers
source                  1..50
                        mol_type = other DNA
                        organism = Homo sapiens
SEQUENCE: 148
aaaaatgtta gggtggtgca aaagtgatcg tggttttgc aatttttaa                50

SEQ ID NO: 149          moltype = DNA   length = 50
FEATURE                 Location/Qualifiers
source                  1..50
                        mol_type = other DNA
                        organism = Homo sapiens
SEQUENCE: 149
tattgtgtga tactgaggct tggagtgtga atgaatcctt cacccaggta              50

SEQ ID NO: 150          moltype = DNA   length = 50
FEATURE                 Location/Qualifiers
source                  1..50
                        mol_type = other DNA
                        organism = Homo sapiens
SEQUENCE: 150
tcggctcggt cctgaggaga aggactcagc cgcggctgcg ggacccgggc              50

SEQ ID NO: 151          moltype = DNA   length = 50
FEATURE                 Location/Qualifiers
source                  1..50
                        mol_type = other DNA
                        organism = Homo sapiens
SEQUENCE: 151
cgccgctgcc ggggttgccag cggagtcgcg cgtcgggagc tacgtagggc             50

SEQ ID NO: 152          moltype = DNA   length = 50
FEATURE                 Location/Qualifiers
source                  1..50
                        mol_type = other DNA
                        organism = Homo sapiens
```

```
SEQUENCE: 152
ccctctatc aatgatgaga ctgatgctga gaaaagtaac atgattatgt                    50

SEQ ID NO: 153           moltype = DNA   length = 50
FEATURE                  Location/Qualifiers
source                   1..50
                         mol_type = other DNA
                         organism = Homo sapiens
SEQUENCE: 153
tacacattaa agcagatctg gagtctgaag tagctataaa gcagctataa                   50

SEQ ID NO: 154           moltype = DNA   length = 50
FEATURE                  Location/Qualifiers
source                   1..50
                         mol_type = other DNA
                         organism = Homo sapiens
SEQUENCE: 154
agaagcatgc ctttcagggc attgataaaa agagtgaaat gttcaggacc                   50

SEQ ID NO: 155           moltype = DNA   length = 50
FEATURE                  Location/Qualifiers
source                   1..50
                         mol_type = other DNA
                         organism = Homo sapiens
SEQUENCE: 155
ctgagcaaga tgcaggatga caatcaggtc atggtgtctg agggcatcat                   50

SEQ ID NO: 156           moltype = DNA   length = 50
FEATURE                  Location/Qualifiers
source                   1..50
                         mol_type = other DNA
                         organism = Homo sapiens
SEQUENCE: 156
gcgcgttccc ggcagctgcg ggctccgagg ccagagagaa aagactgcga                   50

SEQ ID NO: 157           moltype = DNA   length = 50
FEATURE                  Location/Qualifiers
source                   1..50
                         mol_type = other DNA
                         organism = Homo sapiens
SEQUENCE: 157
gagcaacgcg actgaccgtg gtcgtgggcg gacggcggct gcagcgtgga                   50

SEQ ID NO: 158           moltype = DNA   length = 100
FEATURE                  Location/Qualifiers
source                   1..100
                         mol_type = other DNA
                         organism = Homo sapiens
SEQUENCE: 158
ctggttttcc gtctggtgag gggttacttc cgggtcggac ggcgctagct gcagcatcgg        60
agtgtggcag tgctgggctg gccggcgggc tgggctgcgg                             100

SEQ ID NO: 159           moltype = DNA   length = 50
FEATURE                  Location/Qualifiers
source                   1..50
                         mol_type = other DNA
                         organism = Homo sapiens
SEQUENCE: 159
ctgcgcagaa acgctgatcc ggaaggcgct ggctgagtcg attgcaggtc                   50

SEQ ID NO: 160           moltype = DNA   length = 50
FEATURE                  Location/Qualifiers
source                   1..50
                         mol_type = other DNA
                         organism = Homo sapiens
SEQUENCE: 160
ctttcggcgg gtgacatctt tgctgagggc tcaagcggag cgataggtca                   50

SEQ ID NO: 161           moltype = DNA   length = 50
FEATURE                  Location/Qualifiers
source                   1..50
                         mol_type = other DNA
                         organism = Homo sapiens
SEQUENCE: 161
cttcgaaaat gagggtgaag atgaagccat gtttgtagaa tatagaaaac                   50

SEQ ID NO: 162           moltype = DNA   length = 50
FEATURE                  Location/Qualifiers
source                   1..50
```

```
                        mol_type = other DNA
                        organism = Homo sapiens
SEQUENCE: 162
ggagctgctg gccaggccgg agcgaggcag cgcgcccggc tcccgcgcca        50

SEQ ID NO: 163          moltype = DNA  length = 50
FEATURE                 Location/Qualifiers
source                  1..50
                        mol_type = other DNA
                        organism = Homo sapiens
SEQUENCE: 163
tggcaggtct agtgtctttg ccacttgcct ggtgatttct atgatgaaat        50

SEQ ID NO: 164          moltype = DNA  length = 150
FEATURE                 Location/Qualifiers
source                  1..150
                        mol_type = other DNA
                        organism = Homo sapiens
SEQUENCE: 164
ggttacttct gtggacttgg gccgaacagc actgtctaag caggacatga aaagaagggg    60
gaagcgtctc tccttttccc ttcatggaac tttccattga aaaattagcc ccttccagtc   120
cttctcggat gaagcacagt tgccggttac                                    150

SEQ ID NO: 165          moltype = DNA  length = 50
FEATURE                 Location/Qualifiers
source                  1..50
                        mol_type = other DNA
                        organism = Homo sapiens
SEQUENCE: 165
cagcaactgt gataccttgt agaatatgag tgatatgcaa gctgtgtttt        50

SEQ ID NO: 166          moltype = DNA  length = 50
FEATURE                 Location/Qualifiers
source                  1..50
                        mol_type = other DNA
                        organism = Homo sapiens
SEQUENCE: 166
aaccccaggc cagggaggcc cgggtttggg atgccttcct cgggagtgtg        50

SEQ ID NO: 167          moltype = DNA  length = 50
FEATURE                 Location/Qualifiers
source                  1..50
                        mol_type = other DNA
                        organism = Homo sapiens
SEQUENCE: 167
aggccacagc cgctccctcg ctctgctggg gcctccggac gcgcttccca        50

SEQ ID NO: 168          moltype = DNA  length = 150
FEATURE                 Location/Qualifiers
source                  1..150
                        mol_type = other DNA
                        organism = Homo sapiens
SEQUENCE: 168
gttggtgttg aggtgagtcc ggtccctttt gcatccctac cccgacactg cgggttgtca    60
caacggcacc ctccgctttt ctctctgcct cggatttagt cgtgactgtg tgtctccgcc   120
gtggtgcagc ttcaggcctc tcccgcatct                                    150

SEQ ID NO: 169          moltype = DNA  length = 50
FEATURE                 Location/Qualifiers
source                  1..50
                        mol_type = other DNA
                        organism = Homo sapiens
SEQUENCE: 169
tgaagtgagg taggaggttg atcaaatttt ctgtataaca ggaatatgga        50

SEQ ID NO: 170          moltype = DNA  length = 50
FEATURE                 Location/Qualifiers
source                  1..50
                        mol_type = other DNA
                        organism = Homo sapiens
SEQUENCE: 170
tgaataatag gcttatatgt tataacatca aaatataatt cgagtttgac        50

SEQ ID NO: 171          moltype = DNA  length = 50
FEATURE                 Location/Qualifiers
source                  1..50
                        mol_type = other DNA
                        organism = Homo sapiens
SEQUENCE: 171
```

```
taagtgtaac attcagaacc gggtaacatt cggcgaccga acgcggcggt              50

SEQ ID NO: 172          moltype = DNA   length = 50
FEATURE                 Location/Qualifiers
source                  1..50
                        mol_type = other DNA
                        organism = Homo sapiens
SEQUENCE: 172
cacaaagtag ggaatattca agattgtatt aggttggtgc aaaagtgatt              50

SEQ ID NO: 173          moltype = DNA   length = 50
FEATURE                 Location/Qualifiers
source                  1..50
                        mol_type = other DNA
                        organism = Homo sapiens
SEQUENCE: 173
ctgctggttt ccaactttcc gctcatcttc gtctccgcag cctcctgcaa              50

SEQ ID NO: 174          moltype = DNA   length = 50
FEATURE                 Location/Qualifiers
source                  1..50
                        mol_type = other DNA
                        organism = Homo sapiens
SEQUENCE: 174
gcagggacaa cagtcagagg gctgcagggg cctgaagcca gacacgggac              50

SEQ ID NO: 175          moltype = DNA   length = 50
FEATURE                 Location/Qualifiers
source                  1..50
                        mol_type = other DNA
                        organism = Homo sapiens
SEQUENCE: 175
gaccggaggg aggaggagga ggaagaagag cggagagaga aggaagaggc              50

SEQ ID NO: 176          moltype = DNA   length = 50
FEATURE                 Location/Qualifiers
source                  1..50
                        mol_type = other DNA
                        organism = Homo sapiens
SEQUENCE: 176
gactttggac atgaagtccc cagcatctct accagctcca ctgaattaag              50

SEQ ID NO: 177          moltype = DNA   length = 100
FEATURE                 Location/Qualifiers
source                  1..100
                        mol_type = other DNA
                        organism = Homo sapiens
SEQUENCE: 177
gctgtcggcc gagcgcgccg tcaccggcta caccgacccc tacaccgggc agcagatctc  60
cctcttccag gccatgcaga aggacctcat cgtccgggag                        100

SEQ ID NO: 178          moltype = DNA   length = 100
FEATURE                 Location/Qualifiers
source                  1..100
                        mol_type = other DNA
                        organism = Homo sapiens
SEQUENCE: 178
tgctgtcggc cgagcgcgcc gtcaccggct acaccgaccc ctacaccggg cagcagatct  60
ccctcttcca ggccatgcag aaggacctca tcgtccggga                        100

SEQ ID NO: 179          moltype = DNA   length = 100
FEATURE                 Location/Qualifiers
source                  1..100
                        mol_type = other DNA
                        organism = Homo sapiens
SEQUENCE: 179
ctgtcggccg agcgcgccgt caccggctac accgacccct acaccgggca gcagatctcc  60
ctcttccagg ccatgcagaa ggacctcatc gtccgggagc                        100

SEQ ID NO: 180          moltype = DNA   length = 100
FEATURE                 Location/Qualifiers
source                  1..100
                        mol_type = other DNA
                        organism = Homo sapiens
SEQUENCE: 180
gtcggccgag cgcgccgtca ccggctacac cgacccctac accggcagc agatctccct   60
cttccaggcc atgcagaagg acctcatcgt ccgggagcac                        100

SEQ ID NO: 181          moltype = DNA   length = 150
```

| FEATURE | Location/Qualifiers |
|---|---|
| source | 1..150 |
| | mol_type = other DNA |
| | organism = Homo sapiens |

SEQUENCE: 181

```
agctgctgtc ggccgagcgc gccgtcaccg gctacaccga ccccctacacc gggcagcaga    60
tctccctctt ccaggccatg cagaaggacc tcatcgtccg ggagcacggc atccgcctgc   120
tggaggccca gatcgccacg ggcggcgtca                                    150
```

| SEQ ID NO: 182 | moltype = DNA   length = 100 |
|---|---|
| FEATURE | Location/Qualifiers |
| source | 1..100 |
| | mol_type = other DNA |
| | organism = Homo sapiens |

SEQUENCE: 182

```
tcggccgagc gcgccgtcac cggctacacc gaccccctaca ccgggcagca gatctccctc    60
ttccaggcca tgcagaagga cctcatcgtc cgggagcacg                         100
```

| SEQ ID NO: 183 | moltype = DNA   length = 100 |
|---|---|
| FEATURE | Location/Qualifiers |
| source | 1..100 |
| | mol_type = other DNA |
| | organism = Homo sapiens |

SEQUENCE: 183

```
ggagaaccgg aagctgaccg tggaggaggc gttcaaagca ggaatgttcg ggaaagaaac    60
ctacgtgaag ctgctgtcgg ccgagcgcgc cgtcaccggc                         100
```

| SEQ ID NO: 184 | moltype = DNA   length = 50 |
|---|---|
| FEATURE | Location/Qualifiers |
| source | 1..50 |
| | mol_type = other DNA |
| | organism = Homo sapiens |

SEQUENCE: 184

```
ggcgagcggg caggtgcggc gggtgcggcg ggtgcggcgg gtgcggcggg              50
```

| SEQ ID NO: 185 | moltype = DNA   length = 100 |
|---|---|
| FEATURE | Location/Qualifiers |
| source | 1..100 |
| | mol_type = other DNA |
| | organism = Homo sapiens |

SEQUENCE: 185

```
cagagatgcc cctgctggcc gcaaagtggg tctcattgct gcccgccgga ctggacgtct    60
ccggggaacc aagactgtgc aggagaaaga gaactagtgc                         100
```

| SEQ ID NO: 186 | moltype = DNA   length = 50 |
|---|---|
| FEATURE | Location/Qualifiers |
| source | 1..50 |
| | mol_type = other DNA |
| | organism = Homo sapiens |

SEQUENCE: 186

```
gggctccgag tcccgggagc ggaggccgga gtcgggttcc tgtagaggct              50
```

| SEQ ID NO: 187 | moltype = DNA   length = 50 |
|---|---|
| FEATURE | Location/Qualifiers |
| source | 1..50 |
| | mol_type = other DNA |
| | organism = Homo sapiens |

SEQUENCE: 187

```
agacaagctc ggtctgaggt tgttttcctt tgaactggct ctctcacatt              50
```

| SEQ ID NO: 188 | moltype = DNA   length = 50 |
|---|---|
| FEATURE | Location/Qualifiers |
| source | 1..50 |
| | mol_type = other DNA |
| | organism = Homo sapiens |

SEQUENCE: 188

```
gagattgaga ccagcctggg ctaacatagc gagaccccgt ctctacaaaa              50
```

| SEQ ID NO: 189 | moltype = DNA   length = 50 |
|---|---|
| FEATURE | Location/Qualifiers |
| source | 1..50 |
| | mol_type = other DNA |
| | organism = Homo sapiens |

SEQUENCE: 189

```
accacgccat aggcccacac atcagactct gtagtgtagc ggttataaaa              50
```

| SEQ ID NO: 190 | moltype = DNA   length = 50 |
|---|---|
| FEATURE | Location/Qualifiers |
| source | 1..50 |

```
                        mol_type = other DNA
                        organism = Homo sapiens
SEQUENCE: 190
cctctaaaaa acccattccc acactagctc ggactgaggc caagataacc        50

SEQ ID NO: 191          moltype = DNA   length = 50
FEATURE                 Location/Qualifiers
source                  1..50
                        mol_type = other DNA
                        organism = Homo sapiens
SEQUENCE: 191
tgtagtggtc ctgcaggagt ggagcctgta ggacttgctt ctcagcggct        50

SEQ ID NO: 192          moltype = DNA   length = 50
FEATURE                 Location/Qualifiers
source                  1..50
                        mol_type = other DNA
                        organism = Homo sapiens
SEQUENCE: 192
tgtcaggcag tggagttact tacagacaag agccttgctc aggccagccc        50

SEQ ID NO: 193          moltype = DNA   length = 50
FEATURE                 Location/Qualifiers
source                  1..50
                        mol_type = other DNA
                        organism = Homo sapiens
SEQUENCE: 193
tggaggctgc agttagctat gatcacacca ctgcattcca gcctgagtga        50

SEQ ID NO: 194          moltype = DNA   length = 50
FEATURE                 Location/Qualifiers
source                  1..50
                        mol_type = other DNA
                        organism = Homo sapiens
SEQUENCE: 194
ctaattgatc acaaccaatt acagatttct tgtttcttc tcctctccca         50

SEQ ID NO: 195          moltype = DNA   length = 50
FEATURE                 Location/Qualifiers
source                  1..50
                        mol_type = other DNA
                        organism = Homo sapiens
SEQUENCE: 195
cttttcctca ttcgccagct ttgtaggtga ctgacctagt aggcatgtgg        50

SEQ ID NO: 196          moltype = DNA   length = 50
FEATURE                 Location/Qualifiers
source                  1..50
                        mol_type = other DNA
                        organism = Homo sapiens
SEQUENCE: 196
ctgggcaaca tagcgagacc ccgtctctct ctagtgtgtg tgtgtgtgtg        50

SEQ ID NO: 197          moltype = DNA   length = 50
FEATURE                 Location/Qualifiers
source                  1..50
                        mol_type = other DNA
                        organism = Homo sapiens
SEQUENCE: 197
caggggagtt gaggaggttt actgcaaaca actgttcttt tttcttttgg        50

SEQ ID NO: 198          moltype = DNA   length = 50
FEATURE                 Location/Qualifiers
source                  1..50
                        mol_type = other DNA
                        organism = Homo sapiens
SEQUENCE: 198
gattctagaa tcacaaataa agccaattaa aatctttaaa tttgttgtac        50

SEQ ID NO: 199          moltype = DNA   length = 50
FEATURE                 Location/Qualifiers
source                  1..50
                        mol_type = other DNA
                        organism = Homo sapiens
SEQUENCE: 199
tggcacatct agcaacagag ccagatcaga acccaggtaa gctcggtctc        50

SEQ ID NO: 200          moltype = DNA   length = 200
FEATURE                 Location/Qualifiers
```

```
source                  1..200
                        mol_type = other DNA
                        organism = Homo sapiens
SEQUENCE: 200
accatggttg tctgagcatg cagcatgctt gtctgctcat accccatggt ttctgagcag    60
gaaccttcat tgtctactgc tttacaggga aatagtgttt tatgcatcgt gtatatgagt   120
ttagtattta ctcatattct atgactctct actcttagat cacttctgcc tttttctgca   180
cattgtttat ctgttccaaa                                               200

SEQ ID NO: 201          moltype = DNA   length = 50
FEATURE                 Location/Qualifiers
source                  1..50
                        mol_type = other DNA
                        organism = Homo sapiens
SEQUENCE: 201
aacccaaaaa gtcacacctg tgtcctgtgc gcgggtgctg caggcttagg               50

SEQ ID NO: 202          moltype = DNA   length = 20
FEATURE                 Location/Qualifiers
source                  1..20
                        mol_type = other DNA
                        organism = synthetic construct
SEQUENCE: 202
ccagtgcagg gtccgaggta                                                20

SEQ ID NO: 203          moltype = DNA   length = 19
FEATURE                 Location/Qualifiers
source                  1..19
                        mol_type = other DNA
                        organism = synthetic construct
SEQUENCE: 203
cccaggactc ggctcacac                                                 19

SEQ ID NO: 204          moltype = DNA   length = 21
FEATURE                 Location/Qualifiers
source                  1..21
                        mol_type = other DNA
                        organism = Homo sapiens
SEQUENCE: 204
caggactcgg ctcacacatg c                                              21

SEQ ID NO: 205          moltype = DNA   length = 23
FEATURE                 Location/Qualifiers
source                  1..23
                        mol_type = other DNA
                        organism = Homo sapiens
SEQUENCE: 205
ttgtctaacc ctaactgaga agg                                            23

SEQ ID NO: 206          moltype = DNA   length = 21
FEATURE                 Location/Qualifiers
source                  1..21
                        mol_type = other DNA
                        organism = synthetic construct
SEQUENCE: 206
agacgacagc tggatcacac g                                              21

SEQ ID NO: 207          moltype = RNA   length = 21
FEATURE                 Location/Qualifiers
source                  1..21
                        mol_type = other RNA
                        organism = synthetic construct
SEQUENCE: 207
caggactcgg ctcacacatg c                                              21

SEQ ID NO: 208          moltype = RNA   length = 21
FEATURE                 Location/Qualifiers
source                  1..21
                        mol_type = other RNA
                        organism = synthetic construct
SEQUENCE: 208
agacgacagc tggatcacac g                                              21

SEQ ID NO: 209          moltype = DNA   length = 26
FEATURE                 Location/Qualifiers
source                  1..26
                        mol_type = other DNA
                        organism = Homo sapiens
SEQUENCE: 209
```

```
acctgggatt ctctacgaaa ttcagt                                                              26

SEQ ID NO: 210          moltype = DNA  length = 26
FEATURE                 Location/Qualifiers
source                  1..26
                        mol_type = other DNA
                        organism = Homo sapiens
SEQUENCE: 210
ccttgattga ggtatagttc ttgtct                                                              26

SEQ ID NO: 211          moltype = DNA  length = 26
FEATURE                 Location/Qualifiers
source                  1..26
                        mol_type = other DNA
                        organism = Homo sapiens
SEQUENCE: 211
tggtgcttag taaactcttg gttcca                                                              26

SEQ ID NO: 212          moltype = DNA  length = 26
FEATURE                 Location/Qualifiers
source                  1..26
                        mol_type = other DNA
                        organism = Homo sapiens
SEQUENCE: 212
ctgcaggagt aaggacagga aggtgc                                                              26
```

METHODS AND SYSTEMS FOR SEQUENCING POLYNUCLEOTIDES

SUBMISSION OF SEQUENCE LISTING

The Sequence Listing associated with this application is filed in electronic format via EFS-Web and hereby incorporated by reference into the specification in its entirety. The name of the text file containing the Sequence Listing is "UCAL034USSeqListing.xml." The size of the text file is 194 KB and the text file was created on Sep. 21, 2023.

TECHNOLOGY FIELD

The present disclosure relates generally to detection of non-coding RNAs molecules in a sample or diagnosis of subject based upon detection or quantification of non-coding nucleic acid sequences in a sample, specifically to identify and use of molecular biomarkers for cancer including breast cancer.

BACKGROUND

The widespread reprogramming of the gene expression landscape is a hallmark of cancer development. Thus, the systematic identification of regulatory pathways that drive pathologic gene expression patterns is a crucial step towards understanding and treating cancer. Over the years, a multitude of regulatory mechanisms have been implicated in oncogenic expression of genes involved in cancer cell differentiation, survival, invasion, and spread. While numerous studies have focused on the transcriptional pathways that underlie oncogenesis, post-transcriptional regulatory pathways have also emerged as major regulators of this process. For example, microRNAs (small non-coding RNAs), a subclass of small RNAs that function in gene silencing, were among the first characterized post-transcriptional regulators of breast cancer progression (1). RNA-binding proteins (RBPs) are also critical posttranscriptional regulators of gene expression, and several specific RBPs have been shown to affect oncogenesis and cancer progression (e.g. 2-5). Recently, it was demonstrated that tRNAs (6) and tRNA fragments (7), which are other classes of small non-coding RNAs, play a fundamental role in breast cancer progression.

Despite the diverse repertoire of regulatory mechanisms involved in cancers, a shared characteristic among them is that they co-opt and dys-regulate existing pathways within the cell. In other words, cancer cells adopt myriad strategies, such as somatic mutations (e.g. KRAS, 8), gene fusions (e.g. BCR-ABL, 9), epigenetic modifications (e.g. promoter hypermethylation, 10), and regulatory mechanisms disruptions (NFkB transcription factors, 10) to over-activate oncogenic and to down-regulate tumor suppressive pathways (11, 12). While these strategies rely on the pathologic modulation of regulatory programs that are already in place, there is an often-overlooked possibility that cancer cells may be capable of evolving or engineering specialized regulatory pathways that drive tumorigenesis.

SUMMARY

The described invention provides novel small non-coding RNAs that serve as biomarkers which are indicative of cancer such as breast cancer, and which may be used to accurately diagnose breast cancer in a subject. In some embodiments, the methods comprise detection of extracellular, circulating small RNAs in a suitable sample. In some embodiments, the sample is a human serum sample. In some embodiments, the sample is a fractionated human serum sample comprising exosomes that comprise small non-coding mRNA.

The invention also relates to detecting the presence of non-coding RNAs in a blood or blood serum sample. In some embodiments, the disclosure relates to a method for detecting a hyperproliferative cell in a subject comprising detecting the absence, presence or quantity of non-coding nucleic acid in a serum or plasma sample. In some embodiments, the methods comprise isolating total RNA from the sample and detecting the presence of non-coding mRNA sequences and correlating the quantity of non-coding mRNA to the likelihood of whether the subject comprises one or a plurality of hyperproliferative cells. In some embodiments, the methods comprise isolating total RNA from the sample and detecting the presence of non-coding mRNA sequences and correlating the quantity of non-coding mRNA to the likelihood of whether the subject comprises one or a plurality of cancer cells. In some embodiments, the methods comprise isolating total RNA from the sample and detecting the presence of non-coding mRNA sequences and correlating the quantity of non-coding mRNA to the likelihood of whether the subject comprises one or a plurality of solid tumor cells. In some embodiments, the methods comprise isolating total RNA from the sample and detecting the presence of non-coding mRNA sequences and correlating the quantity of non-coding mRNA to the likelihood of whether the subject comprises one or a plurality of breast cancer cells.

In some embodiments, methods are described herein for determining a diagnosis comprising determining the presence of one or a combination of non-coding nucleic acids from a sample derived from a subject's plasma or serum sample according to the methods previously described and providing a diagnosis based on the presence of said one or combination of non-coding nucleic acids. In some embodiments, the diagnosis determined is cancer such as breast cancer.

In some embodiments, a computer implemented method is used for determining the presence or absence of one or a combination of non-coding nucleic acids comprising practicing the methods previously described, comprising quantitating the abundance of one or a combination of non-coding nucleic acids of reference from one or a plurality of samples comprising one or a combination of non-coding nucleic acids, computationally determining the normalized amount of one or a combination of non-coding nucleic acids in the one or plurality of samples, and determining the presence or absence of one or a combination of non-coding nucleic acids based on said normalized amount. In some embodiments, quantitation comprising sequencing the sample of total RNA isolated from a sample in question. In some embodiments, computational analysis is performed on sequence data derived from a whole blood or serum sample. In some embodiments, the results of the previously described computer implemented methods are output wherein said output could be a diagnosis, for example a diagnosis of a hyperproliferative disorder, such as breast cancer. For other embodiments, additional sample related information can be output, such as information with regards to presence or absence of known tumor antigens in a sample. Outputting can be by a variety of means as described herein, for example results can be output visually on, for example a computer monitor and the like, or output can be hardcopy, such as a printed paper report and the like.

BRIEF DESCRIPTION OF THE DRAWINGS

FIG. 1A is a heatmap representing the relative abundance of 437 small non-coding RNAs that are significantly expressed in breast cancer lines but not normal HUMECs. HUMECs were processed in triplicate, whereas all other cell lines were assayed in duplicate. FIG. 1B is a heatmap that shows that of the 437 small RNAs identified in (FIG. 1A), 201 were significantly expressed in breast tumor biopsy small RNA gene expression profiles collected as part of the Cancer Genome Atlas (TCGA-BRCA), and these 201 were also largely absent from the adjacent normal tissue collected from the ~200 individuals in this dataset. FIG. 1C is a heatmap that shows that these 201 cancer-specific small RNAs were classified as orphan non-coding RNAs or oncRNAs and were independently validated in a third dataset comparing small RNA profiles from four normal epithelial samples and 10 patient-derived xenograft models.

In FIG. 2A, in order to identify cancer-specific small RNAs, those RNAs that are largely absent in normal cells/tissue but are generally expressed in cancer cells were searched. Such RNA species were identified from two independent sources: (i) profiling of breast cancer cell lines in comparison to HUMECs, and (ii) The Cancer Genome Atlas dataset (TCGA-BRCA) with ~200 normal tissue biopsies and ~1000 tumor samples. These two independent sets were then overlapped to identify orphan non-coding RNAs (oncRNAs). As shown in FIG. 2A, a strong overlap was seen between these two analyses (hypergeometric P~0). In FIG. 2B, the total abundance of the 201 oncRNAs were calculated across four normal epithelial samples and 10 PDX models. As shown in FIG. 2B, total oncRNA expression can perfectly predict whether samples are cancerous or normal (both AUC and AUPRC equals 1.0).

FIG. 3A is a volcano plot comparing the expression of oncRNAs in poorly metastatic breast cancer cells relative to their highly metastatic derivatives. Highlighted is the oncRNA T3p, which is significantly upregulated in highly metastatic cells. FIG. 3B is a schematic that shows that T3p maps to the 3' end (CR7 domain) of TERC, the RNA component of telomerase. FIG. 3C shows that expression of T3p (cpm) in breast tumor biopsies and their matched normal tissue in the TCGA-BRCA dataset. Paired Wilcoxon test was used to calculate the associated p-value. FIG. 3D shows T3p expression across the TCGA-BRCA dataset. FIG. 3E shows survival analysis in the TCGA-BRCA dataset for patients stratified based on the expression of T3p in their tumors. Top and bottom third of samples were included in this analysis (Log-rank test). FIG. 3F shows expression of T3p across normal, stage I, and stage II or III samples in the TCGA-BRCA dataset (*, $P<0.05$; ***, $P<0.001$; using Mann-Whitney test).

FIG. 4A-D shows that the oncRNA T3p is associated with aggressive breast cancers. FIG. 4A shows a tabulation of the number of samples in the TCGA-BRCA dataset based on the sample type (normal vs. breast cancer). Also included is the Fisher exact test $\chi^2$ test associated with each contingency table. FIG. 4B shows a stratification of patients in the TCGA-BRCA dataset based on whether T3p was detected in their tumor biopsies or not. Mere detection of T3p in biopsies is associated with poor survival in breast cancer (P calculated based on a log-rank test). FIG. 4C shows a comparison of T3p expression levels in TCGA-BRCA samples divided based on ER, PR, or HER2 status. FIG. 4D shows T3p is significantly expressed in breast cancer PDX models (***, $P<0.001$; Mann-Whitney test).

FIG. 6A shows a comparison of gene expression changes induced by anti-T3p LNAs in MDA-LM2 cells versus T3p mimetics in MDA-MB-231 cells. Reported is the associated Pearson correlation (P~0). FIG. 6B shows a bioluminescence imaging plot of lung metastasis by MDA-LM2 cells transfected with anti-T3p LNAs (LNA-T3p) or scrambled LNAs (LNA-Scr); n=4 or 5 in each cohort. Statistical significance was measured using two-way ANOVA. The area under the curve was also calculated for each mouse (change in normalized lung photon flux times days elapsed). Error bars indicate s.e.m.**, $P<0.01$ by a one-tailed Mann-Whitney test. FIG. 6C graphically shows the number of visible metastatic nodules that were counted in three mice from each cohort. The panel on the right shows hematoxylin and eosin stain (H&E) stained representative lung sections from each cohort along with the median counts. Error bars indicate s.e.m.*, $P<0.05$ by a one-tailed Mann-Whitney test.

FIG. 7A shows a large fraction of oncRNAs were detected in exosomal small RNA data collected from MDA-MB-231 cells but not normal HUVEC cells. FIG. 7B shows small RNA profiling of exososmal RNA collected from breast cancer cell lines and normal HUMECs. Shown is a heatmap showing the detection of oncRNAs among the extracellular population. FIG. 7C shows the detection of oncRNAs in serum samples collected from breast cancer patients with stage II and III disease. As a point of reference, data from 11 healthy individuals from an independent study is used as a reference.

FIG. 8A shows the results of validation of T3p upregulation in highly metastatic MDA-LM2 cells relative to poorly metastatic parental cells in a previously published small RNA-seq data (7) and quantitative RT-PCR (n=6 in each sample, **, $P<0.01$; using a two-tailed Mann-Whitney test. FIG. 8B shows T3p can be detected at high levels in the absolute majority of sera collected from patients but is present at very low levels (or undetected) in serum samples collected from healthy individuals.

FIG. 9A shows normalized T3p expression from small RNA sequencing of the indicated cell lines on the x-axis. All cancer lines were prepared and processed in biological duplicates and HMECs in biological triplicate. Cell lines shape-coded by sub-type: HMEC (circles on left hand side of panel), triple negative breast cancer (TNBC; squares, triangle and diamonds in the middle of the panel), HER2 positive (circles and squares to the right-hand side of the panel), and luminal (triangles to the right hand side of the panel). FIG. 9B depicts a comparison of T3p expression levels in TCGA-BRCA samples divided based on ER, PR, or HER2 status (n=1033, 1030, and 715, respectively). The mean±s.d. are shown for each cohort. FIG. 9C depict the relative T3p expression measured by qRT-PCR in two poorly and two highly metastatic breast cancer PDX models.

FIG. 10A depicts that T3p was present in the sequenced small RNA isolated from extracellular vesicles (EVs) from 7/8 breast cancer cell lines, and not present in HMEC EVs. Samples were processed and prepared in biological replicates and combined prior to calculation of counts-per-million. Cell lines shape-coded by sub-type: HMEC (the first column on the X-axis beginning from the left), triple negative breast cancer (TNBC; the next four columns to the right of HMEC), HER2 positive (the next two columns on the right of the HER2 set of samples), and luminal (the last two columns on the rightmost side of the graph). FIG. 10B shows Pearson correlation coefficients between oncRNA expression levels in total intracellular (IC) and extracellular (CM) compartments, as well as IC and extracellular vesicle (EV) compartments. n=2 biologically independent experiments per cell line. FIG. 10C shows 10 bootstrap based receiver operating characteristic (ROC) curves depicting the classification performance of a gradient boosted classifier trained on oncRNA expression levels in the TCGA-BRCA dataset and tested on serum samples from healthy volunteers or breast cancer patients (GSE49035). FIG. 10D shows T3p can be detected at high levels in the absolute majority of sera collected from patients but is present at very low levels (or undetected) in serum samples collected from healthy individuals. The panel on the right shows T3p levels in sera collected from individual breast cancer patients. n=biologically independent samples. Shown are mean±s.e.m; P was calculated using a two-tailed Mann Whitney test. FIG. 10E depicts that T3p can be detected at high levels in the absolute majority of sera collected from patients but is present at very low levels (or undetected) in serum samples collected from healthy individuals. The panel on the right shows T3p levels in sera collected from individual breast cancer patients. n=40 biologically independent samples. Shown are mean±s.e.m; P was calculated using a two-tailed Mann Whitney test. Bootstrapped ROC curves (10 times) were generated for a gradient boosted classifier trained on miRNAs expression in the TCGA-BRCA dataset, and tested on serum samples from healthy volunteers or breast cancer patients (data not shown).

DETAILED DESCRIPTION

Figure 1A:
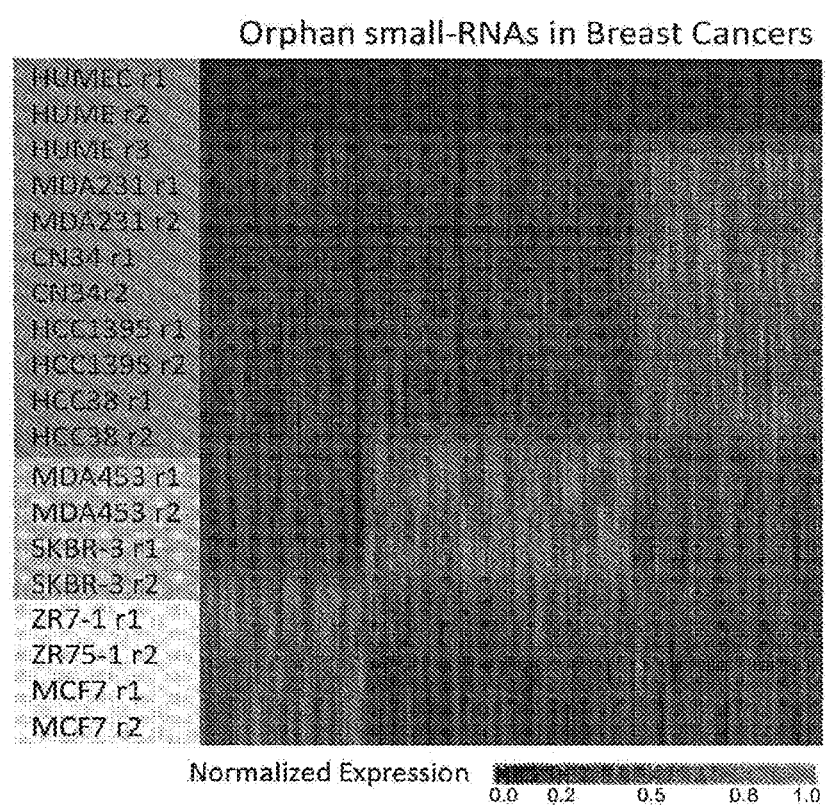
FIG. 1A-FIG. 1C show the discovery, annotation, and validation of cancer-specific orphan non-coding RNAs in breast cancer.

The disclosure provides novel small non-coding RNAs that serve as biomarkers which are indicative of breast cancer, and which may be used to accurately diagnose or grade breast cancer in a subject. In some embodiments, the methods entail detection of extracellular, circulating small RNAs in a suitable sample.

Definitions

Prior to setting forth the invention in detail, definitions of certain terms to be used herein are provided.

Unless defined otherwise, technical and scientific terms used herein have the same meaning as commonly understood by one of ordinary skill in the art to which this invention belongs. For example, Singleton et al., Dictionary of Microbiology and Molecular Biology 2nd ed., J. Wiley & Sons (New York, NY 1994), provide one skilled in the art with a general guide to many of the terms used in the present application. Additionally, the practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", 2nd edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", 4th edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

As used in the present disclosure and claims, the singular forms "a", "an" and "the" include plural forms unless the context clearly dictates otherwise.

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The term "about" or "approximately" as used herein is meant to refer to within 5%, within 4%, within 3%, within 2%, within 1%, of a given value or range.

The term "antibody" as used herein refers to an immunoglobulin molecule that recognizes and specifically binds a target, such as a protein, polypeptide, peptide, carbohydrate, polynucleotide, lipid, or combinations of the foregoing, through at least one antigen-binding site. As used herein, the term encompasses intact polyclonal antibodies, intact monoclonal antibodies, single chain antibodies, antibody fragments (such as Fab, Fab', F(ab')2, and Fv fragments), single chain Fv (scFv) antibodies, multispecific antibodies such as bispecific antibodies, monospecific antibodies, monovalent antibodies, chimeric antibodies, humanized antibodies, human antibodies, fusion proteins comprising an antigen-binding site of an antibody, and any other modified immunoglobulin molecule comprising an antigen-binding site as long as the antibodies exhibit the desired biological binding activity. An antibody can be any of the five major classes of immunoglobulins: IgA, IgD, IgE, IgG, and IgM, or subclasses (isotypes) thereof (e.g., IgG1, IgG2, IgG3, IgG4, IgA1, and IgA2), based on the identity of their heavy chain constant domains referred to as alpha, delta, epsilon, gamma, and mu, respectively. The different classes of immunoglobulins have different and well-known subunit structures and three-dimensional configurations. Antibodies can be naked or conjugated to other molecules, including but not limited to, toxins and radioisotopes.

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, single chain antibodies, and multispecific antibodies formed from antibody fragments. "Antibody fragment" as used herein comprises at least one antigen-binding site or epitope-binding site. The term "variable region" of an antibody refers to the variable region of an antibody light chain, or the variable region of an antibody heavy chain, either alone or in combination. The variable region of a heavy chain or a light chain generally consists of four framework regions (FR) connected by three complementarity determining regions (CDRs), also known as "hypervariable regions". The CDRs in each chain are held together in close proximity by the framework regions and contribute to the formation of the antigen-binding site(s) of the antibody. There are at least two techniques for determining CDRs: (1) an approach based on cross-species sequence variability (i.e., Kabat et al., 1991, Sequences of Proteins of Immunological Interest, 5th Edition, National Institutes of Health, Bethesda, MD), and (2) an approach based on crystallographic studies of antigen-antibody complexes (Al-Lazikani et al., 1997, J. Mol. Biol., 273:927-948). In addition, combinations of these two approaches are sometimes used in the art to determine CDRs.

The term "biomarker" as used herein refers to a biological molecule present in an individual at varying concentrations useful in predicting the cancer status of an individual. A biomarker may include but is not limited to, nucleic acids, proteins and variants and fragments thereof. A biomarker may be DNA comprising the entire or partial nucleic acid sequence encoding the biomarker, or the complement of such a sequence. Biomarker nucleic acids useful in the invention are considered to include both DNA and RNA comprising the entire or partial sequence of any of the nucleic acid sequences of interest.

The term "bodily fluid" as used herein refers to a bodily fluid comprising non-coding RNA (ncRNA) including blood (or a fraction of blood such as plasma or serum), lymph, mucus, tears, saliva, sputum, urine, semen, stool, CSF (cerebrospinal fluid), breast milk, and, ascities fluid. In some embodiments, the bodily fluid is urine. In some embodiments, the bodily fluid is fractionated serum comprising exosomes.

The terms "cancer" and "cancerous" as used herein refer to or describe the physiological condition in mammals in which a population of cells are characterized by unregulated cell growth. In some embodiments, the cancer is a breast cancer.

The term "correlate" or "correlating" as used herein refers to a statistical association between instances of two events, where events may include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases. The present invention provides small non-coding RNAs, the levels of which are correlated with a particular outcome measure, such as between the level of a small non-coding RNA and the likelihood of developing breast cancer. For example, the increased level of a small non-coding RNA may be negatively correlated with a likelihood of good clinical outcome for the patient. In this case, for example, the patient may have a decreased likelihood of long-term survival without recurrence of the cancer and/or a positive response to a chemotherapy, and the like. Such a negative correlation indicates that the patient likely has a poor prognosis or will respond poorly to a chemotherapy, and this may be demonstrated statistically in various ways, e.g., by a high hazard ratio.

The term "high stringency" as used herein refers to conditions that: (1) employ low ionic strength and high temperature for washing, for example 15 mM sodium chloride/1.5 mM sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 in 5× SSC (0.75M NaCl, 75 mM sodium citrate) at 42° C.; or (3) employ during hybridization 50% formamide in 5× SSC, 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2× SSC and 50% formamide, followed by a wash consisting of 0.1× SSC containing EDTA at 55° C.

The term "hyperproliferative disorder" refers to a disease or disorder characterized by abnormal proliferation, abnormal growth, abnormal senescence, abnormal quiescence, or abnormal removal of cells in an organism, and includes all forms of hyperplasias, neoplasias, and cancer. In some embodiments, the hyperproliferative disease is a cancer derived from the gastrointestinal tract or urinary system. In some embodiments, a hyperproliferative disease is a cancer of the adrenal gland, bladder, bone, bone marrow, brain, spine, breast, cervix, gall bladder, ganglia, gastrointestinal tract, stomach, colon, heart, kidney, liver, lung, muscle, ovary, pancreas, parathyroid, penis, prostate, salivary glands, skin, spleen, testis, thymus, thyroid, or uterus. In some embodiments, the term hyperproliferative disease is a cancer chosen from: lung cancer, bone cancer, CMML, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, testicular, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

The terms "identical" or "percent identity" or "homology" in the context of two or more nucleic acids, as used herein, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variations thereof. In some embodiments, two nucleic acids of the invention are substantially identical, meaning they have at least about 70%, at least about 75%, at least about 80%, at least about 85%, at least about 90%, and in some embodiments at least about 95%, 96%, 97%, 98%, 99% nucleotide or amino acid residue sequence identity, when compared and aligned for maximum correspondence, as measured using a sequence comparison algorithm or by visual inspection. In some embodiments, identity exists over a region of the sequences that is at least about 10, at least about 20, at least about 40-60 nucleotides, at least about 60-80 nucleotides or any integral value therebetween. In some embodiments, identity exists over a longer region than 60-80 nucleotides, such as at least about 80-100 nucleotides, and in some embodiments the sequences are substantially identical over the full length of the sequences being compared.

The term "level" as used herein refers to qualitative or quantitative determination of the number of copies of a non-coding RNA transcript. An RNA transcript exhibits an "increased level" when the level of the RNA transcript is higher in a first sample, such as in a clinically relevant subpopulation of patients (e.g., patients who have cancer), than in a second sample, such as in a related subpopulation (e.g., patients who do not have cancer). In the context of an analysis of a level of an RNA transcript in a tumor sample obtained from an individual patient, an RNA transcript exhibits "increased level" when the level of the RNA transcript in the subject trends toward, or more closely approximates, the level characteristic of a clinically relevant subpopulation of patients.

The term "metastasis" as used herein refers to the process by which a cancer spreads or transfers from the site of origin to other regions of the body with the development of a similar cancerous lesion at a new location. A "metastatic" or "metastasizing" cell is one that loses adhesive contacts with neighboring cells and migrates (e.g., via the bloodstream or lymph) from the primary site of disease to secondary sites.

The term "monoclonal antibody" as used herein refers to a homogeneous antibody population involved in the highly specific recognition and binding of a single antigenic determinant or epitope. This is in contrast to polyclonal antibodies that typically include a mixture of different antibodies directed against a variety of different antigenic determinants. The term "monoclonal antibody" encompasses both intact and full-length monoclonal antibodies as well as antibody fragments (e.g., Fab, Fab', F(ab')2, Fv), single chain (scFv) antibodies, fusion proteins comprising an antibody portion, and any other modified immunoglobulin molecule comprising an antigen-binding site. Furthermore, "monoclonal antibody" refers to such antibodies made by any number of techniques, including but not limited to, hybridoma production, phage selection, recombinant expression, and transgenic animals.

The term "normalized" as used herein with regard to non-coding RNA transcript, refers to the level of the RNA transcript, relative to the mean levels of transcript of a set of reference RNA transcripts. The reference RNA transcripts are based on their minimal variation across patients, tissues, or treatments. Alternatively, the non-coding RNA transcript may be normalized to the totality of tested RNA transcripts, or a subset of such tested RNA transcripts.

A "patient response" may be assessed using any endpoint indicating a benefit to the patient, including, without limitation, (1) inhibition, to some extent, of tumor growth, including slowing down and complete growth arrest; (2) reduction in the number of tumor cells; (3) reduction in tumor size; (4) inhibition (i.e., reduction, slowing down or complete stopping) of tumor cell infiltration into adjacent peripheral organs and/or tissues; (5) inhibition (i.e. reduction, slowing down or complete stopping) of metastasis; (6) enhancement of anti-tumor immune response, which may, but does not have to, result in the regression or rejection of the tumor; (7) relief, to some extent, of one or more symptoms associated with the cancer; (8) increase in the length of survival following treatment; and/or (9) decreased mortality at a given point of time following treatment.

The terms "polynucleotide" and "nucleic acid" and "nucleic acid molecule" are used interchangeably herein and refer to polymers of nucleotides of any length, and include DNA and RNA. The polynucleotides can be deoxyribonucleotides, ribonucleotides, modified nucleotides or bases, and/or their analogs, or any substrate that can be incorporated into a polymer by DNA or RNA polymerase.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids), as well as other modifications known in the art. It is understood that, because the polypeptides of this invention may be based upon antibodies or fusion proteins, in certain embodiments, the polypeptides can occur as single chains or associated chains (e.g., dimers).

The term "prognosis" as used herein refers to the prediction of the likelihood of cancer-attributable death or progression, including recurrence, metastatic spread, and drug resistance, of neoplastic disease, such as breast cancer.

The term "reference" RNA transcript as used herein refers to an RNA transcript whose level can be used to compare the level of an RNA transcript in a test sample. In an embodiment of the invention, reference RNA transcripts include housekeeping genes, such as beta-globin, alcohol dehydrogenase, or any other RNA transcript, the level or expression of which does not vary depending on the disease status of the cell containing the RNA transcript. In another embodiment, all of the assayed RNA transcripts, or a subset thereof, may serve as reference RNA transcripts.

The term "small non-coding RNA" (ncRNA) as used herein, refers to RNA that is not translated into protein and includes transfer RNA (tRNA), ribosomal RNA (rRNA), snoRNAs, microRNA (miRNA), siRNAs, small nuclear (snRNA), Y RNA, vault RNA, antisense RNA, tiRNA (transcription initiation RNA), TSSa-RNA (transcriptional start-site associated RNA) and piwiRNA (piRNA). Small ncRNA have a length of less than 200 nucleotides. Preferably, a small ncRNA as used herein is between 50 and 100 nucleotides. A ncRNA may be of endogenous origin (e.g., a human small non-coding RNA) or exogenous origin (e.g., virus, bacteria, parasite). "Canonical" ncRNA refers to the sequence of the RNA as predicted from the genome sequence and is the most abundant sequence identified for a particular RNA. "Trimmed" ncRNA refers to an ncRNA in which exonuclease-mediated nucleotide trimming has removed one or more nucleotides at the 5' and/or 3' end of the molecule. "Extended ncRNA" refers to an small non-coding RNA that is longer than the canonical small non-coding RNA sequence and is a term recognized in the art. The nucleotides making up the extension correspond to nucleotides of the precursor sequence and are therefore encoded by the genome in contrast to non-templated nucleotide addition. In some embodiments, any of the methods disclosed herein comprise detecting any one or combination of RNAs disclosed above.

The term "subject" as used herein refers to any animal (e.g., a mammal), including, but not limited to, humans, non-human primates, canines, felines, rodents, and the like. Preferably, the subject is a human subject. The terms "subject," "individual," and "patient" are used interchangeably herein. The terms "subject," "individual," and "patient" thus encompass individuals having cancer (e.g., breast cancer), including those who have undergone or are candidates for resection (surgery) to remove cancerous tissue.

The term "therapeutically effective amount" means a quantity sufficient to achieve a desired therapeutic effect, for example, an amount which results in the prevention or amelioration of or a decrease in the symptoms associated with a disease that is being treated, e.g., disorders associated with cancer growth or a hyperproliferative disorder. The amount of compound administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The regimen of administration can affect what constitutes an effective amount. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation. Typically, an effective amount of the compounds of the present invention, sufficient for achieving a therapeutic effect, range from about 0.000001 mg per kilogram body weight per day to about 10,000 mg per kilogram body weight per day. Preferably, the dosage ranges are from about 0.0001 mg per kilogram body weight per day to about 100 mg per kilogram body weight per day. The compounds disclosed herein can also be administered in combination with each other, or with one or more additional therapeutic compounds.

The term "salt" refers to acidic salts formed with inorganic and/or organic acids, as well as basic salts formed with inorganic and/or organic bases. Examples of these acids and bases are well known to those of ordinary skill in the art. Such acid addition salts will normally be pharmaceutically acceptable although salts of non-pharmaceutically acceptable acids may be of utility in the preparation and purification of the compound in question. Acid addition salts of the compounds of the invention are most suitably formed from pharmaceutically acceptable acids, and include for example those formed with inorganic acids e.g. hydrochloric, hydrobromic, sulphuric or phosphoric acids and organic acids e.g. succinic, malaeic, acetic or fumaric acid. Other non-pharmaceutically acceptable salts e.g. oxalates can be used for example in the isolation of the compounds of the invention, for laboratory use, or for subsequent conversion to a pharmaceutically acceptable acid addition salt. Also included within the scope of the invention are solvates and hydrates of the invention. n vivo hydrolyzable esters or amides of certain compounds of the invention can be formed by treating those compounds having a free hydroxy or amino functionality with the acid chloride of the desired ester in the presence of a base in an inert solvent such as methylene chloride or chloroform. Suitable bases include triethylamine or pyridine. Conversely, compounds of the invention having a free carboxy group can be esterified using standard conditions which can include activation followed by treatment with the desired alcohol in the presence of a suitable base. Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Particularly preferred salts are sodium, lysine and arginine salts of the compounds of the invention. Such salts can be formed by procedures well known and described in the art.

Other acids such as oxalic acid, which cannot be considered pharmaceutically acceptable, can be useful in the preparation of salts useful as intermediates in obtaining a chemical compound of the invention and its pharmaceutically acceptable acid addition salt. Metal salts of a chemical compound of the invention include alkali metal salts, such as the sodium salt of a chemical compound of the invention containing a carboxy group. Mixtures of isomers obtainable according to the invention can be separated in a manner known per se into the individual isomers; diastereoisomers can be separated, for example, by partitioning between polyphasic solvent mixtures, recrystallization and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallization, or by chromatography over optically active column materials.

As used herein, the term "sample" refers to a biological sample obtained or derived from a source of interest, as described herein. In some embodiments, a source of interest comprises an organism, such as an animal or human. In some embodiments, a biological sample comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

The terms "treating" or "treatment" or "treat" as used herein refer to both 1) therapeutic measures that cure, slow down, lessen symptoms of, and/or halt progression of a diagnosed pathologic condition or disorder and 2) prophylactic or preventative measures that prevent or slow the development of a targeted pathologic condition or disorder. Thus those in need of treatment include those already diagnosed with the disorder; those prone to have the disorder; and those in whom the disorder is to be prevented. In some embodiments, a subject is successfully "treated" according to the methods of the present invention if the patient shows one or more of the following: a reduction in the number of and/or complete absence of cancer cells; a reduction in the tumor size; an inhibition of tumor growth; inhibition of and/or an absence of cancer cell infiltration into peripheral organs including the spread of cancer cells into soft tissue and bone; inhibition of and/or an absence of tumor or cancer cell metastasis; inhibition and/or an absence of cancer growth; relief of one or more symptoms associated with the specific cancer; reduced morbidity and mortality; improvement in quality of life; reduction in tumorigenicity; reduction in the number or frequency of cancer stem cells; or some combination of such effects.

The term "tumor" as used herein, refers to all neoplastic cell growth and proliferation, whether malignant or benign, and all pre-cancerous and cancerous cells and tissues.

The term "T3p" refers to the last 45 nucleotides of non-coding RNA (in a 5' to 3' orientation) encoded or generated by the human TERC nucleotide sequence. The sequence may be found in PCT serial No. PCT/US2008/055709 and associated sequence listing, the contents of which are hereby incorporated by reference in their entirety.

The term "tumor sample" as used herein refers to a sample comprising tumor material obtained from a cancer patient. The term encompasses tumor tissue samples, for example, tissue obtained by surgical resection and tissue obtained by biopsy, such as for example, a core biopsy or a fine needle biopsy. In a particular embodiment, the tumor sample is a fixed, wax-embedded tissue sample, such as a formalin-fixed, paraffin-embedded tissue sample. Additionally, the term "tumor sample" encompasses a sample comprising tumor cells obtained from sites other than the primary tumor, e.g., circulating tumor cells. The term also encompasses cells that are the progeny of the patient's tumor cells, e.g. cell culture samples derived from primary tumor cells or circulating tumor cells. The term further encompasses samples that may comprise protein or nucleic acid material shed from tumor cells in vivo, e.g., bone marrow, blood, plasma, serum, and the like. The term also encompasses samples that have been enriched for tumor cells or otherwise manipulated after their procurement and samples comprising polynucleotides and/or polypeptides that are obtained from a patient's tumor material.

Small RNA Biomarkers of Cancer

The human genome encodes for a vast amount of small non-protein-coding RNA (ncRNAs) transcripts. Multiple ncRNA classes have been described including the highly abundant transfer RNAs (tRNAs), ribosomal RNAs (rRNAs), small nucleolar RNAs (snoRNAs), microRNAs (miRNAs), small interfering RNAs (siRNAs), small nuclear RNAs (snRNAs), and piwi-interacting RNAs (piRNAs) (Amaral et al., 2008; Martens-Uzunova et al., 2013). Small non-coding RNAs act as translational repressors by binding to target mRNAs at sites with adequate sequence complementary (Ameres et al., 2007), while the highly abundant cytoplasmic Y RNAs function in RNA quality control by affecting the subcellular location of Ro proteins (Sim et al., 2009). The repressive activity of mature small non-coding RNAs on mRNA translation is shared by other classes of ncRNAs, including siRNAs and endo-siRNAs, in addition to piRNAs that silence retrotransposons at defined subcellular locations (Chuma and Pillai, 2009). Small non-coding RNA activity relies on sufficient levels of abundance in the cytoplasm, and interaction with RNA-induced silencing complexes (RISC) localized at endosomal membranes (Gibbings et al., 2009; Lee et al., 2009a), whereas low abundant small non-coding RNAs have less impact on translational repression. As a consequence, subtle alterations in the levels of certain small non-coding RNA may already influence cellular processes, while strong perturbations can cause disease. Besides abundance, interactions with (RISC) proteins but also RNA partners and correct subcellular localization are interrelated factors that control small non-coding RNA physiology (Mullokandov et al., 2012; Wee et al., 2012).

Small RNAs can be secreted in cell-derived extracellular vesicles, such as exosomes. Both mRNA and small non-coding RNA species have been found contained in exosomes. As such, exosomes can provide a means for transfer and protection of RNA content from degradation in the environment, enabling a stable source for reliable detection of RNA biomarkers.

The disclosure relates to small non-coding RNA biomarkers found to be differentially present in biological samples derived from subjects having breast cancer, as compared with subjects who are "normal," i.e., subjects who do not have breast cancer. A small non-coding RNA biomarker or set of small non-coding RNA biomarkers is differentially present between samples if the difference between the levels of expression of the small non-coding RNA biomarker or set of small non-coding RNA biomarkers in the samples is determined to be statistically significant. Common tests for statistical significance include, but are not limited to, t-test, ANOVA, Kniskal-Wallis, Wilcoxon, Mann-Whitney, and odds ratio. small non-coding RNA biomarkers, alone or in combination, can be used to provide a measure of the relative risk that a subject has or does not have cancer.

Small non-coding RNA biomarkers of breast cancer were discovered by small RNA sequencing of multiple breast cancer subtypes as well as human mammary epithelial cells, and identifying previously unknown small non-coding RNAs that are specifically expressed in breast cancer cells. 200 previously unknown small non-coding RNAs that are specifically expressed in breast cancer cells were identified in this manner (see Table 1). These small non-coding RNA biomarkers can now be used to determine the cancer status of a subject, for example, a subject whose breast cancer status, was previously unknown or who is suspected to be suffering from breast cancer. This may be accomplished by determining the level of one or more of the identified small non-coding RNAs, or combinations thereof, in a biological sample derived from the subject. A difference in the level of one or more of these small non-coding RNA biomarkers as compared to that in a biological sample derived from a normal subject is an indication that the subject has breast cancer.

A subject having a difference in the level of one or more small non-coding RNA biomarkers as compared to a normal subject may have breast cancer, including early-stage, moderate or mid-stage, or severe or late-stage breast cancer. In one embodiment, the level of one or more small non-coding RNA biomarkers may be used to diagnose breast cancer, in a subject having symptoms characteristic of early-stage cancer.

In one embodiment, the level of one or more small non-coding RNA biomarkers may be used to monitor the course of cancer progression, for example breast cancer progression, in a subject. The cancer status of a subject can change over time. For example, the cancer may worsen or improve over time. With such worsening or improvement, the level of one or more small non-coding RNA biomarkers may change in a statistically significant fashion, as detected in samples derived from the subject. For example, the level of one or more of a small non-coding RNA biomarker may increase over time with the development of breast cancer. Thus, the course of breast cancer, progression, in a subject can be monitored by determining the level of one or more small non-coding RNA biomarkers in a first sample derived from a subject, and determining the level of one or more small non-coding RNA biomarkers in a second sample derived from a subject, where the second sample is obtained after the first sample. The levels in the second sample relative to the levels in the first sample are indicative of disease progression. For example, an increase in the level of one or more of a small non-coding RNA biomarker from Table 1, Table 2 or Table 3, from the first sample to the second sample is indicative that the subject has developed breast cancer, or that the disease has worsened. Conversely, a decrease in the level of one or more of a small non-coding RNA biomarker from Table 1, Table 2 or Table 3 from the first sample to the second sample indicates that the disease has improved. In one embodiment, the one or more small non-coding RNA biomarkers are from Table 3, and combinations thereof.

Whether or not the level of a small non-coding RNA biomarker in a biological sample derived from a test subject is different from the level of the small non-coding RNA biomarker present in a normal subject may be ascertained by comparing the level of the small non-coding RNA biomarker in the sample from the test subject with a suitable control. The skilled person can select an appropriate control for the assay in question. For example, a suitable control may be a biological sample derived from a known subject, e.g., a subject known to be a normal subject that does not have cancer. If a suitable control is obtained from a normal subject, a statistically significant difference in the level of a small non-coding RNA biomarker in a test subject relative to the suitable control is indicative that the subject has breast cancer. In one embodiment, the difference in the level of a small non-coding RNA biomarker is an increase. A suitable control may also be a reference standard. A reference standard serves as a reference level for comparison, such that test samples can be compared to the reference standard in order to infer the breast cancer, status of a subject. A reference standard may be representative of the level of one or more small non-coding RNA biomarkers in a known subject, e.g., a subject known to be a normal subject, or a subject known to have breast cancer. Likewise, a reference standard may be representative of the level of one or more small non-coding RNA biomarkers in a population of known subjects, e.g., a population of subjects known to be normal subjects, or a population of subjects known to have breast cancer. The reference standard may be obtained, for example, by pooling samples from a plurality of individuals and determining the level of a small non-coding RNA biomarker in the pooled samples, to thereby produce a standard over an averaged population. Such a reference standard represents an average level of a small non-coding RNA biomarker among a population of individuals. A reference standard may also be obtained, for example, by averaging the level of a small non-coding RNA biomarker determined to be present in individual samples obtained from a plurality of individuals. Such a standard is also representative of an average level of a small non-coding RNA biomarker among a population of individuals. A reference standard may also be a collection of values each representing the level of a small non-coding RNA biomarker in a known subject in a population of individuals. In certain embodiments, test samples may be compared against such a collection of values in order to infer the breast cancer, status of a subject. In certain embodiments, the reference standard is an absolute value. In such embodiments, test samples may be compared against the absolute value in order to infer the breast cancer, status of a subject. In a one embodiment, a comparison between the level of one or more small non-coding RNA biomarkers in a sample relative to a suitable control is made by executing a software classification algorithm. In some embodiments, the increased expression of one or a combination non-coding RNAs in Table 1, 2 and/or 3 wherein the increased expression is about 10%, 20%, 30%, 40%, 50%, 60%, 70%, 80%, 90%, 95 percent or about 100% or more expression than the expression of the same non-coding RNA in a normal sample. In some embodiments, the increased expression of one or a combination non-coding RNAs in Table 1, 2 and/or 3 wherein the increased expression is about 2×, 3×, 4×, 5×, 6×, 7×, 8×, 9× or about 10× or more expression than the expression of the same one or combination of non-coding RNA in a normal sample. In some embodiments, one or a plurality of the non-coding RNA sequences or nucleic acid sequences with about 70%, 80%, 81%, 82%, 83%, 84, 85%, 86%, 87%, 88%, 89%, 90%, 91%, 92%, 93%, 94%, 95%, 96%, 97%, 98%, or about 99% homology to the nucleic acid sequences in Tables 1, 2, and/or 3. In some embodiments, the mere presence or expression of one or a plurality non-coding RNAs alone or in combination with expression of one or a plurality of the sequences in Tables 1, 2, or 3. In some embodiments, the mere presence or expression of one or a plurality non-coding RNAs homolgous to alone or in combination with expression of one or a plurality of the sequences with about 70%, 80%, 81%, 82%, 83%, 84, 85%, 86%, 87%, 88%, 89%, 90%, 91%, 92%, 93%, 94%, 95%, 96%, 97%, 98%, or about 99% homology to the nucleic acid sequences in Tables 1, 2, and/or 3. In some embodiments, these homologous sequences comprise one or a plurality of fragments of the nucleic acid sequences disclosed in Tables 1, 2, and/or 3.

The skilled person can readily envision additional suitable controls that may be appropriate depending on the assay in question. The aforementioned suitable controls are exemplary, and are not intended to be limiting.

Generally, an increase in the level of one or more of a small non-coding RNA biomarker from Table 1, Table 2 or Table 3 in a biological sample derived from a test subject relative to a suitable control representative of the level of one or more of a small non-coding RNA biomarker from Table 1, Table 2 or Table 3 in a normal subject will indicate that the test subject has breast cancer. In some instances where the levels of two or more small non-coding RNA biomarkers are determined in a test subject, there may be an increase in the level of one or more small non-coding RNA biomarkers, and no change or an increase in the level of one or more additional small non-coding RNA biomarkers, relative to a suitable control. In such instances, a difference in the level of one or more of the small non-coding RNA biomarkers relative to a suitable control representative of the level of the small non-coding RNA biomarkers in a normal subject indicates that the test subject has breast cancer. Determination of such a difference may be aided by the execution of a software classification algorithm, as described herein.

Biological Samples

The expression level of one or more small non-coding RNA biomarkers may be determined in a biological sample derived from a subject. A sample derived from a subject is one that originates from a subject. Such a sample may be further processed after it is obtained from the subject. For example, RNA may be isolated from a sample. In this example, the RNA isolated from the sample is also a sample derived from a subject. A biological sample useful for determining the level of one or more small non-coding RNA biomarkers may be obtained from essentially any source, including cells, tissues, and fluids throughout the body.

In some embodiments, the biological sample used for determining the level of one or more small non-coding RNA biomarkers is a sample containing circulating small non-coding RNAs, e.g., extracellular small non-coding RNAs. Extracellular small non-coding RNAs freely circulate in a wide range of biological material, including bodily fluids, such as fluids from the circulatory system, e.g., a blood sample or a lymph sample, or from another bodily fluid such as urine or saliva. Accordingly, in some embodiments, the biological sample used for determining the level of one or more small non-coding RNA biomarkers is a bodily fluid, for example, blood, fractions thereof, serum, plasma, urine, saliva, tears, sweat, semen, vaginal secretions, lymph, bronchial secretions, CSF, whole blood, etc. In some embodiments, the sample is a sample that is obtained non-invasively. In some embodiments, the sample is a serum sample from a human.

In some embodiments, any of the methods disclosed herein comprise using a small volume sample. In some embodiments, the methods disclosed comprise isolating total RNA and/or amplifying non-coding RNA in a sample of no more than about 20 microliters of sample, 40 microliters of sample, 80 microliters of sample, 100 microliters of sample, 200 microliters of sample, 300 microliters of sample, 400 microliters of sample, 500 microliters of sample, 600 microliters of sample, 700 microliters of sample, 800 microliters of sample, 900 microliters of sample, 1 milliter of sample, 1.1 milliters of sample, 1.2 milliters of sample, 1.3 milliters of sample, 1.4 milliters of sample, 1.5 milliters of sample, 1.6 milliters of sample, 1.7 milliters of sample, 1.8 milliters of sample, 1.9 milliters of sample, 2.0 milliters of sample. In some embodiments, the sample size is from about 25 microliters to about 2 milliliters of liquid sample in the form of subject plasma, whole blood or serum.

In some embodiments, the methods disclosed comprise isolating total RNA and/or amplifying non-coding RNA in a sample of no more than about 20 microliters of serum, 40 microliters of serum, 80 microliters of serum, 100 microliters of serum, 200 microliters of serum, 300 microliters of serum, 400 microliters of serum, 500 microliters of serum, 600 microliters of serum, 700 microliters of serum, 800 microliters of serum, 900 microliters of serum, 1 milliter of serum, 1.1 milliters of serum, 1.2 milliters of serum, 1.3 milliters of serum, 1.4 milliters of serum, 1.5 milliters of serum, 1.6 milliters of serum, 1.7 milliters of serum, 1.8 milliters of serum, 1.9 milliters of serum, 2.0 milliters of serum.

Circulating small non-coding RNAs include small non-coding RNAs in cells, extracellular small non-coding RNAs in microvesicles, in exosomes and extracellular small non-coding RNAs that are not associated with cells or microvesicles (extracellular, non-vesicular small non-coding RNA). In some embodiments, the biological sample used for determining the level of one or more small non-coding RNA biomarkers (e.g., a sample containing circulating small non-coding RNA) may contain cells. In other embodiments, the biological sample may be free or substantially free of cells (e.g., a serum sample). In some embodiments, a sample containing circulating small non-coding RNAs, e.g., extracellular small non-coding RNAs, is a blood-derived sample. Exemplary blood-derived sample types include, e.g., a plasma sample, a serum sample, a blood sample, etc. In other embodiments, a sample containing circulating small non-coding RNAs is a lymph sample. Circulating small non-coding RNAs are also found in urine and saliva, and biological samples derived from these sources are likewise suitable for determining the level of one or more small non-coding RNA biomarkers.

In some embodiments, any of the methods of the disclosure comprise the step of isolating total RNA from a sample or cell or exosome or microvesicle. Methods of isolating RNA for expression analysis from blood, plasma and/or serum (see for example, Tsui NB et al. (2002) Clin. Chem. 48,1647-53, incorporated by reference in its entirety herein) and from urine (see for example, Boom R et al. (1990) J Clin Microbiol. 28, 495-503, incorporated by reference in its entirety herein) have been described.

Determining the Level of Small RNA Biomarkers in a Sample

The level of one or more small non-coding RNA biomarkers in a biological sample may be determined by any suitable method. Any reliable method for measuring the level or amount of small non-coding RNA in a sample may be used. Generally, small non-coding RNA can be detected and quantified from a sample (including fractions thereof), such as samples of isolated RNA by various methods known for mRNA, including, for example, amplification-based methods (e.g., Polymerase Chain Reaction (PCR), Real-Time Polymerase Chain Reaction (RT-PCR), Quantitative Polymerase Chain Reaction (qPCR), rolling circle amplification, etc.), hybridization-based methods (e.g., hybridization arrays (e.g., microarrays), NanoString analysis, Northern Blot analysis, branched DNA (bDNA) signal amplification, in situ hybridization, etc.), and sequencing-based methods (e.g., next-generation sequencing methods, for example, using the Illumina or IonTorrent platforms). Other exemplary techniques include ribonuclease protection assay (RPA) and mass spectroscopy.

In some embodiments, RNA is converted to DNA (cDNA) prior to analysis. cDNA can be generated by reverse transcription of isolated small non-coding RNA using conventional techniques. In some embodiments, small non-coding RNA is amplified prior to measurement. In other embodiments, the level of small non-coding RNA is measured during the amplification process. In still other embodiments, the level of small non-coding RNA is not amplified prior to measurement. Some exemplary methods suitable for determining the level of small non-coding RNA in a sample are described in greater detail below. These methods are provided by way of illustration only, and it will be apparent to a skilled person that other suitable methods may likewise be used.

A. Amplification-Based Methods

Many amplification-based methods exist for detecting the level of small non-coding RNA nucleic acid sequences, including, but not limited to, PCR, RT-PCR, qPCR, and rolling circle amplification. Other amplification-based techniques include, for example, ligase chain reaction, multiplex ligatable probe amplification, in vitro transcription (IVT), strand displacement amplification, transcription-mediated amplification, RNA (Eberwine) amplification, and other methods that are known to persons skilled in the art.

A typical PCR reaction includes multiple steps, or cycles, that selectively amplify target nucleic acid species: a denaturing step, in which a target nucleic acid is denatured; an annealing step, in which a set of PCR primers (i.e., forward and reverse primers) anneal to complementary DNA strands, and an elongation step, in which a thermostable DNA polymerase elongates the primers. By repeating these steps multiple times, a DNA fragment is amplified to produce an amplicon, corresponding to the target sequence. Typical PCR reactions include 20 or more cycles of denaturation, annealing, and elongation. In many cases, the annealing and elongation steps can be performed concurrently, in which case the cycle contains only two steps. A reverse transcription reaction (which produces a cDNA sequence having complementarity to a small non-coding RNA) may be performed prior to PCR amplification. Reverse transcription reactions include the use of, e.g., a RNA-based DNA polymerase (reverse transcriptase) and a primer.

Kits for quantitative real time PCR of small non-coding RNA are known, and are commercially available. Examples of suitable kits include, but are not limited to, the TaqMan miRNA Assay (Applied Biosystems) and the mirVana. qRT-PCR miRNA detection kit (Ambion). The small non-coding RNA can be ligated to a single stranded oligonucleotide containing universal primer sequences, a polyadenylated sequence, or adaptor sequence prior to reverse transcriptase and amplified using a primer complementary to the universal primer sequence, poly(T) primer, or primer comprising a sequence that is complementary to the adaptor sequence.

In some instances, custom qRT-PCR assays can be developed for determination of small non-coding RNA levels. Custom qRT-PCR assays to measure small non-coding RNAs in a biological sample, e.g., a body fluid, can be developed using, for example, methods that involve an extended reverse transcription primer and locked nucleic acid modified PCR. Custom small non-coding RNA assays can be tested by running the assay on a dilution series of chemically synthesized small non-coding RNA corresponding to the target sequence. This permits determination of the limit of detection and linear range of quantitation of each assay. Furthermore, when used as a standard curve, these data permit an estimate of the absolute abundance of small non-coding RNAs measured in biological samples.

Amplification curves may optionally be checked to verify that Ct values are assessed in the linear range of each amplification plot. Typically, the linear range spans several orders of magnitude. For each candidate small non-coding RNA assayed, a chemically synthesized version of the small non-coding RNA can be obtained and analyzed in a dilution series to determine the limit of sensitivity of the assay, and the linear range of quantitation. Relative expression levels may be determined, for example, as described by Livak et al., Methods (2001) Dec.; 25 (4): 402-8.

In some embodiments, two or more small non-coding RNAs are amplified in a single reaction volume. For example, multiplex q-PCR, such as qRT-PCR, enables simultaneous amplification and quantification of at least two small non-coding RNAs of interest in one reaction volume by using more than one pair of primers and/or more than one probe. The primer pairs comprise at least one amplification primer that specifically binds each small non-coding RNA, and the probes are labeled such that they are distinguishable from one another, thus allowing simultaneous quantification of multiple small non-coding RNAs.

Rolling circle amplification is a DNA-polymerase driven reaction that can replicate circularized oligonucleotide probes with either linear or geometric kinetics under isothermal conditions (see, for example, Lizardi et al., Nat. Gen. (1998) 19 (3): 225-232; Gusev et al., Am. J. Pathol. (2001) 159 (1): 63-69; Nallur et al., Nucleic Acids Res. (2001) 29 (23): E118). In the presence of two primers, one hybridizing to the (+) strand of DNA, and the other hybridizing to the (−) strand, a complex pattern of strand displacement results in the generation of over $10^{\wedge}9$ copies of each DNA molecule in 90 minutes or less. Tandemly linked copies of a closed circle DNA molecule may be formed by using a single primer. The process can also be performed using a matrix-associated DNA. The template used for rolling circle amplification may be reverse transcribed. This method can be used as a highly sensitive indicator of small non-coding RNA sequence and expression level at very low small non-coding RNA concentrations (see, for example, Cheng et al., Angew Chem. Int. Ed. Engl. (2009) 48 (18): 3268-72; Neubacher et al., Chembiochem. (2009) 10 (8): 1289-91).

B. Hybridization-Based Methods

Small non-coding RNA may be detected using hybridization-based methods, including but not limited to hybridization arrays (e.g., microarrays), NanoString analysis, Northern Blot analysis, branched DNA (bDNA) signal amplification, and in situ hybridization.

Microarrays can be used to measure the expression levels of large numbers of small non-coding RNAs simultaneously. Microarrays can be fabricated using a variety of technologies, including printing with fine-pointed pins onto glass slides, photolithography using pre-made masks, photolithography using dynamic micromirror devices, ink-jet printing, or electrochemistry on microelectrode arrays. Also useful are microfluidic TaqMan Low-Density Arrays, which are based on an array of microfluidic qRT-PCR reactions, as well as related microfluidic qRT-PCR based methods.

Axon B-4000 scanner and Gene-Pix Pro 4.0 software or other suitable software can be used to scan images. Non-positive spots after background subtraction, and outliers detected by the ESD procedure, are removed. The resulting signal intensity values are normalized to per-chip median values and then used to obtain geometric means and standard errors for each small non-coding RNA. Each signal can be transformed to log base 2, and a one-sample t test can be conducted. Independent hybridizations for each sample can be performed on chips with each small non-coding RNA spotted multiple times to increase the robustness of the data.

Microarrays can be used for the expression profiling of small non-coding RNAs in diseases. For example, RNA can be extracted from a sample and, optionally, the small non-coding RNAs are size-selected from total RNA. Oligonucleotide linkers can be attached to the 5' and 3' ends of the small non-coding RNAs and the resulting ligation products are used as templates for an RT-PCR reaction. The sense strand PCR primer can have a fluorophore attached to its 5' end, thereby labeling the sense strand of the PCR product. The PCR product is denatured and then hybridized to the microarray. A PCR product, referred to as the target nucleic acid that is complementary to the corresponding small non-coding RNA capture probe sequence on the array will hybridize, via base pairing, to the spot at which the, capture probes are affixed. The spot will then fluoresce when excited using a microarray laser scanner.

The fluorescence intensity of each spot is then evaluated in terms of the number of copies of a particular small non-coding RNA, using a number of positive and negative controls and array data normalization methods, which will result in assessment of the level of expression of a particular small non-coding RNA.

Total RNA containing the small non-coding RNA extracted from a body fluid sample can also be used directly without size-selection of the small non-coding RNAs. For example, the RNA can be 3' end labeled using T4 RNA ligase and a fluorophore-labeled short RNA linker. Fluorophore-labeled small non-coding RNAs complementary to the corresponding small non-coding RNA capture probe sequences on the array hybridize, via base pairing, to the spot at which the capture probes are affixed. The fluorescence intensity of each spot is then evaluated in terms of the number of copies of a particular small non-coding RNA, using a number of positive and negative controls and array data normalization methods, which will result in assessment of the level of expression of a particular small non-coding RNA.

Several types of microarrays can be employed including, but not limited to, spotted oligonucleotide microarrays, pre-fabricated oligonucleotide microarrays or spotted long oligonucleotide arrays.

Small non-coding RNAs can also be detected without amplification using the nCounter Analysis System (NanoString Technologies, Seattle, Wash.). This technology employs two nucleic acid-based probes that hybridize in solution (e.g., a reporter probe and a capture probe). After hybridization, excess probes are removed, and probe/target complexes are analyzed in accordance with the manufacturer's protocol. nCounter miRNA assay kits are available from NanoString Technologies, which are capable of distinguishing between highly similar small non-coding RNAs with great specificity.

Small non-coding RNAs can also be detected using branched DNA (bDNA) signal amplification (see, for example, Urdea, Nature Biotechnology (1994), 12:926-928). small non-coding RNA assays based on bDNA signal amplification are commercially available. One such assay is the QuantiGene™. 2.0 miRNA Assay (Affymetrix, Santa Clara, Calif.).

Northern Blot and in situ hybridization may also be used to detect small non-coding RNAs. Suitable methods for performing Northern Blot and in situ hybridization are known in the art.

In some embodiments, biomarker expression is determined by an assay known to those of skill in the art, including but not limited to, multi-analyte profile test, enzyme-linked immunosorbent assay (ELISA), radioimmunoassay, Western blot assay, immunofluorescent assay, enzyme immunoassay, immunoprecipitation assay, chemiluminescent assay, immunohistochemical assay, dot blot assay, or slot blot assay. In some embodiments, wherein an antibody is used in the assay the antibody is detectably labeled. The antibody labels may include, but are not limited to, immunofluorescent label, chemiluminescent label, phosphorescent label, enzyme label, radiolabel, avidin/biotin, colloidal gold particles, colored particles, and magnetic particles. In some embodiments, biomarker expression is determined by an IHC assay.

In some embodiments, biomarker expression is determined using an agent that specifically binds the biomarker. Any molecular entity that displays specific binding to a biomarker can be employed to determine the level of that biomarker protein in a sample. Specific binding agents include, but are not limited to, antibodies, antibody fragments, antibody mimetics, and polynucleotides (e.g., aptamers). One of skill understands that the degree of specificity required is determined by the particular assay used to detect the biomarker protein. In some embodiments, the disclosure relates to a system comprising a solid support (such as an ELISA plate, gel, bead or column comprising an antibody, antibody fragment, antibody mimetic, and/or polynucleotides capable of binding to T3p or a salt thereof.

C. Sequencing-Based Methods

Advanced sequencing methods can likewise be used as available. For example, small non-coding RNAs can be detected using Illumina. Next Generation Sequencing (e.g., Sequencing-By-Synthesis or TruSeq methods, using, for example, the HiSeq, HiScan, GenomeAnalyzer, or MiSeq systems (Illumina, Inc., San Diego, Calif.)). Small non-coding RNAs can also be detected using Ion Torrent Sequencing (Ion Torrent Systems, Inc., Gulliford, Conn.), or other suitable methods of semiconductor sequencing.

D. Additional small non-coding RNA Detection Tools

Mass spectroscopy can be used to quantify small non-coding RNA using RNase mapping. Isolated RNAs can be enzymatically digested with RNA endonucleases (RNases) having high specificity (e.g., RNase TI, which cleaves at the 3'-side of all unmodified guanosine residues) prior to their analysis by MS or tandem MS (MS/MS) approaches. The first approach developed utilized the on-line chromatographic separation of endonuclease digests by reversed phase HPLC coupled directly to ESI-MS. The presence of posttranscriptional modifications can be revealed by mass shifts from those expected based upon the RNA sequence. Ions of anomalous mass/charge values can then be isolated for tandem MS sequencing to locate the sequence placement of the posttranscriptionally modified nucleoside.

Matrix-assisted laser desorption/ionization mass spectrometry (MALDI-MS) has also been used as an analytical approach for obtaining information about posttranscriptionally modified nucleosides. MALDI-based approaches can be differentiated from ESI-based approaches by the separation step. In MALDI-MS, the mass spectrometer is used to separate the small non-coding RNA.

To analyze a limited quantity of intact small non-coding RNAs, a system of capillary LC coupled with nanoESI-MS can be employed, by using a linear ion trap-orbitrap hybrid mass spectrometer (LTQ Orbitrap XL, Thermo Fisher Scientific) or a tandem-quadrupole time-of-flight mass spectrometer (QSTAR XL, Applied Biosystems) equipped with a custom-made nanospray ion source, a Nanovolume Valve (Valco Instruments), and a splitless nano HPLC system (DiNa, KYA Technologies). Analyte/TEAA is loaded onto a nano-LC trap column, desalted, and then concentrated. Intact small non-coding RNAs are eluted from the trap column and directly injected into a Cl 8 capillary column, and chromatographed by RP-HPLC using a gradient of solvents of increasing polarity. The chromatographic eluent is sprayed from a sprayer tip attached to the capillary column, using an ionization voltage that allows ions to be scanned in the negative polarity mode.

Additional methods for small non-coding RNA detection and measurement include, for example, strand invasion assay (Third Wave Technologies, Inc.), surface plasmon resonance (SPR), cDNA, MTDNA (metallic DNA; Advance Technologies, Saskatoon, SK), and single-molecule methods such as the one developed by US Genomics. Multiple small non-coding RNAs can be detected in a microarray format using a novel approach that combines a surface enzyme reaction with nanoparticle-amplified SPR imaging (SPRI). The surface reaction of poly(A) polymerase creates poly(A) tails on small non-coding RNAs hybridized onto locked nucleic acid (LNA) microarrays. DNA-modified nanoparticles are then adsorbed onto the poly(A) tails and detected with SPRI. This ultrasensitive nanoparticle-amplified SPRI methodology can be used for small non-coding RNA profiling at attamole levels.

E. Detection of Amplified or Non-Amplified Small Non-Coding RNAs

In certain embodiments, labels, dyes, or labeled probes and/or primers are used to detect amplified or unamplified small non-coding RNAs. The skilled artisan will recognize which detection methods are appropriate based on the sensitivity of the detection method and the abundance of the target. Depending on the sensitivity of the detection method and the abundance of the target, amplification may or may not be required prior to detection. One skilled in the art will recognize the detection methods where small non-coding RNA amplification is preferred.

A probe or primer may include standard (A, T or U, G and C) bases, or modified bases. Modified bases include, but are not limited to, the AEGIS bases (from Eragen Biosciences), which have been described, e.g., in U.S. Pat. Nos. 5,432,272, 5,965,364, and 6,001,983. In certain aspects, bases are joined by a natural phosphodiester bond or a different chemical linkage. Different chemical linkages include, but are not limited to, a peptide bond or a Locked Nucleic Acid (LNA) linkage, which is described, e.g., in U.S. Pat. No. 7,060,809.

In a further aspect, oligonucleotide probes or primers present in an amplification reaction are suitable for monitoring the amount of amplification product produced as a function of time. In certain aspects, probes having different single stranded versus double stranded character are used to detect the nucleic acid. Probes include, but are not limited to, the 5'-exonuclease assay (e.g., TAQMAN) probes (see U.S. Pat. No. 5,538,848), stem-loop molecular beacons (see, e.g., U.S. Pat. Nos. 6,103,476 and 5,925,517), stemless or linear beacons (see, e.g., WO 9921881, U.S. Pat. Nos. 6,485,901 and 6,649,349), peptide nucleic acid (PNA) Molecular Beacons (see, e.g., U.S. Pat. Nos. 6,355,421 and 6,593,091), linear PNA beacons (see, e.g. U.S. Pat. No. 6,329,144), non-FRET probes (see, e.g., U.S. Pat. No. 6,150,097), Sunrise.™/AmplifluorB.™. probes (see, e.g., U.S. Pat. No. 6,548,250), stem-loop and duplex SCORPION probes (see, e.g., U.S. Pat. No. 6,589,743), bulge loop probes (see, e.g., U.S. Pat. No. 6,590,091), pseudo knot probes (see, e.g., U.S. Pat. No. 6,548,250), cyclicons (see, e.g., U.S. Pat. No. 6,383,752), MGB Eclipse.™. probe (Epoch Biosciences), hairpin probes (see, e.g., U.S. Pat. No. 6,596,490), PNA light-up probes, antiprimer quench probes (Li et al., Clin. Chem. 53:624-633 (2006)), self-assembled nanoparticle probes, and ferrocene-modified probes described, for example, in U.S. Pat. No. 6,485,901.

In certain embodiments, one or more of the primers in an amplification reaction can include a label. In yet further embodiments, different probes or primers comprise detectable labels that are distinguishable from one another. In some embodiments a nucleic acid, such as the probe or primer, may be labeled with two or more distinguishable labels.

In some aspects, a label is attached to one or more probes and has one or more of the following properties: (i) provides a detectable signal; (ii) interacts with a second label to modify the detectable signal provided by the second label, e.g., FRET (Fluorescent Resonance Energy Transfer); (iii) stabilizes hybridization, e.g., duplex formation; and (iv) provides a member of a binding complex or affinity set, e.g., affinity, antibody-antigen, ionic complexes, hapten-ligand (e.g., biotin-avidin). In still other aspects, use of labels can be accomplished using any one of a large number of known techniques employing known labels, linkages, linking groups, reagents, reaction conditions, and analysis and purification methods.

Small non-coding RNAs can be detected by direct or indirect methods. In a direct detection method, one or more small non-coding RNAs are detected by a detectable label that is linked to a nucleic acid molecule. In such methods, the small non-coding RNAs may be labeled prior to binding to the probe. Therefore, binding is detected by screening for the labeled small non-coding RNA that is bound to the probe. The probe is optionally linked to a bead in the reaction volume.

In certain embodiments, nucleic acids are detected by direct binding with a labeled probe, and the probe is subsequently detected. In one embodiment of the invention, the nucleic acids, such as amplified small non-coding RNAs, are detected using FlexMAP Microspheres (Luminex) conjugated with probes to capture the desired nucleic acids. Some methods may involve detection with polynucleotide probes modified with fluorescent labels or branched DNA (bDNA) detection, for example.

In some embodiments, biomarker expression is determined using a PCR-based assay comprising specific primers and/or probes for each biomarker. As used herein, the term "probe" refers to any molecule that is capable of selectively binding a specifically intended target biomolecule. In some embodiments, herein, the term "probe" refers to any molecule that may bind or associate, indirectly or directly, covalently or non-covalently, to any of the substrates and/or reaction products and/or proteases disclosed herein and whose association or binding is detectable using the methods disclosed herein. In some embodiments, the probe is a fluorogenic probe, antibody or absorbance-based probes. If an absorbance-based probe, the chromophore pNA (para-nitroanaline) may be used as a probe for detection and/or quantification of a target nucleic acid sequence disclosed herein. In some embodiments the probe may be a nucleic acid sequence comprising a fluorogenic molecule or a substrate that when exposed to an enzyme becomes fluorogenic and the nucleic acid sequence is complementary to fragment of nucleic acid sequence comprising 70%, 80%, 81%, 82%, 83%, 84, 85%, 86%, 87%, 88%, 89%, 90%, 91%, 92%, 93%, 94%, 95%, 96%, 97%, 98%, 99% or about 100% sequence identity to any one or combination of nucleic acid sequences in Tables 1, 2, and/or 3.

The target molecule could be any one or combination of nucleic acid sequences identified in Tables 1, 2, and/or 3. In some embodiments, the target molecule is a nucleic acid sequence comprising 70%, 80%, 81%, 82%, 83%, 84, 85%, 86%, 87%, 88%, 89%, 90%, 91%, 92%, 93%, 94%, 95%, 96%, 97%, 98%, or about 99% sequence identity to any one or combination of nucleic acid sequences in Tables 1, 2, and/or 3. Probes can be synthesized by one of skill in the art using known techniques, or derived from biological preparations. Probes may include but are not limited to, RNA, DNA, proteins, peptides, aptamers, antibodies, and organic molecules. The term "primer" or "probe" encompasses oligonucleotides that have a specific sequence or oligonucleotides that have a specific sequence. In some embodiments, the target molecule is any amplified fragment of any one or combination of nucleic acid sequences identified in Tables 1, 2, and/or 3 and/or any one or combination of nucleic acid sequence comprising 70%, 80%, 81%, 82%, 83%, 84, 85%, 86%, 87%, 88%, 89%, 90%, 91%, 92%, 93%, 94%, 95%, 96%, 97%, 98%, or about 99% sequence identity to any one or combination of nucleic acid sequences in Tables 1, 2, and/or 3.

In other embodiments, nucleic acids are detected by indirect detection methods. For example, a biotinylated probe may be combined with a streptavidin-conjugated dye to detect the bound nucleic acid. The streptavidin molecule binds a biotin label on amplified small non-coding RNA, and the bound small non-coding RNA is detected by detecting the dye molecule attached to the streptavidin molecule. In one embodiment, the streptavidin-conjugated dye molecule comprises PHYCOLINK. Streptavidin R-Phycoerythrin (PROzyme). Other conjugated dye molecules are known to persons skilled in the art.

Labels include, but are not limited to: light-emitting, light-scattering, and light-absorbing compounds which generate or quench a detectable fluorescent, chemiluminescent, or bioluminescent signal (see, e.g., Kricka, L., Nonisotopic DNA Probe Techniques, Academic Press, San Diego (1992) and Garman A., Non-Radioactive Labeling, Academic Press (1997)). A dual labeled fluorescent probe that includes a reporter fluorophore and a quencher fluorophore is used in some embodiments. It will be appreciated that pairs of fluorophores are chosen that have distinct emission spectra so that they can be easily distinguished.

In certain embodiments, labels are hybridization-stabilizing moieties which serve to enhance, stabilize, or influence hybridization of duplexes, e.g., intercalators and intercalating dyes (including, but not limited to, ethidium bromide and SYBR-Green), minor-groove binders, and cross-linking functional groups (see, e.g., Blackburn et al., eds. "DNA and RNA Structure" in Nucleic Acids in Chemistry and Biology (1996)).

In other embodiments, methods relying on hybridization and/or ligation to quantify small non-coding RNAs may be used, including oligonucleotide ligation (OLA) methods and methods that allow a distinguishable probe that hybridizes to the target nucleic acid sequence to be separated from an unbound probe. As an example, HARP-like probes, as disclosed in U.S. Publication No. 2006/0078894 may be used to measure the quantity of miRNAs. In such methods, after hybridization between a probe and the targeted nucleic acid, the probe is modified to distinguish the hybridized probe from the unhybridized probe. Thereafter, the probe may be amplified and/or detected. In general, a probe inactivation region comprises a subset of nucleotides within the target hybridization region of the probe. To reduce or prevent amplification or detection of a HARP probe that is not hybridized to its target nucleic acid, and thus allow detection of the target nucleic acid, a post-hybridization probe inactivation step is carried out using an agent which is able to distinguish between a HARP probe that is hybridized to its targeted nucleic acid sequence and the corresponding unhybridized HARP probe. The agent is able to inactivate or modify the unhybridized HARP probe such that it cannot be amplified. A probe ligation reaction may also be used to quantify small non-coding RNAs. In a Multiplex Ligation-dependent Probe Amplification (MLPA) technique (Schouten et al., Nucleic Acids Research 30:e57 (2002)), pairs of probes which hybridize immediately adjacent to each other on the target nucleic acid are ligated to each other driven by the presence of the target nucleic acid. In some aspects, MLPA probes have flanking PCR primer binding sites. MLPA probes are specifically amplified when ligated, thus allowing for detection and quantification of small non-coding RNA biomarkers.

Detecting a Level of Small RNA Biomarker

The small non-coding RNA biomarkers described herein can be used individually or in combination in diagnostic tests to assess the breast cancer status of a subject. Breast cancer status includes the presence or absence of breast cancer. Breast cancer status may also include monitoring the course of breast cancer, for example, monitoring disease progression. Based on the breast cancer status of a subject, additional procedures may be indicated, including, for example, additional diagnostic tests or therapeutic procedures.

The power of a diagnostic test to correctly predict disease status is commonly measured in terms of the accuracy of the assay, the sensitivity of the assay, the specificity of the assay, or the "Area Under a Curve" (AUC), for example, the area under a Receiver Operating Characteristic (ROC) curve. As used herein, accuracy is a measure of the fraction of misclassified samples. Accuracy may be calculated as the total number of correctly classified samples divided by the total number of samples, e.g., in a test population. Sensitivity is a measure of the "true positives" that are predicted by a test to be positive, and may be calculated as the number of correctly identified breast cancer samples divided by the total number of breast cancer samples. Specificity is a measure of the "true negatives" that are predicted by a test to be negative, and may be calculated as the number of correctly identified normal samples divided by the total number of normal samples. AUC is a measure of the area under a Receiver Operating Characteristic curve, which is a plot of sensitivity vs. the false positive rate (1-specificity). The greater the AUC, the more powerful the predictive value of the test. Other useful measures of the utility of a test include the "positive predictive value," which is the percentage of actual positives who test as positives, and the "negative predictive value," which is the percentage of actual negatives who test as negatives. In a preferred embodiment, the level of one or more small non-coding RNA biomarkers in samples derived from subjects having different breast cancer statuses show a statistically significant difference of at least $p=0.05$, e.g., $p=0.05$, $p=0.01$, $p=0.005$, $p=0.001$, etc. relative to normal subjects, as determined relative to a suitable control. In other preferred embodiments, diagnostic tests that use small non-coding RNA biomarkers described herein individually or in combination show an accuracy of at least about 75%, e.g., an accuracy of at least about 75%, about 80%, about 85%, about 90%, about 95%, about 97%, about 99% or about 100%. In other embodiments, diagnostic tests that use small non-coding RNA biomarkers described herein individually or in combination show a specificity of at least about 75%, e.g., a specificity of at least about 75%, about 80%, about 85%, about 90%, about 95%, about 97%, about 99% or about 100%. In other embodiments, diagnostic tests that use small non-coding RNA biomarkers described herein individually or in combination show a sensitivity of at least about 75%, e.g., a sensitivity of at least about 75%, about 80%, about 85%, about 90%, about 95%, about 97%, about 99% or about 100%. In other embodiments, diagnostic tests that use small non-coding RNA biomarkers described herein individually or in combination show a specificity and sensitivity of at least about 75% each, e.g., a specificity and sensitivity of at least about 75%, about 80%, about 85%, about 90%, about 95%, about 97%, about 99% or about 100% (for example, a specificity of at least about 80% and sensitivity of at least about 80%, or for example, a specificity of at least about 80% and sensitivity of at least about 95%).

Each biomarker listed in Tables 1, 2 and 3 is differentially present in biological samples derived from subjects having breast cancer as compared with normal subjects, and thus each is individually useful in facilitating the determination of breast cancer in a test subject. Such a method involves determining the level of the biomarker in a sample derived from the subject. Determining the level of the biomarker in a sample may include measuring, detecting, or assaying the level of the biomarker in the sample using any suitable method, for example, the methods set forth herein. Determining the level of the biomarker in a sample may also include examining the results of an assay that measured, detected, or assayed the level of the biomarker in the sample. The method may also involve comparing the level of the biomarker in a sample with a suitable control. A change in the level of the biomarker relative to that in a normal subject as assessed using a suitable control is indicative of the breast cancer status of the subject. A diagnostic amount of a biomarker that represents an amount of the biomarker above or below which a subject is classified as having a particular breast cancer status can be used. For example, if the biomarker is upregulated in samples derived from an individual having breast cancer as compared to a normal individual, a measured amount above the diagnostic cutoff provides a diagnosis of breast cancer. Generally, the individual small non-coding RNA biomarkers in Tables 1-3 are upregulated in breast cancer samples relative to samples obtained from normal individuals. As is well-understood in the art, adjusting the particular diagnostic cut-off used in an assay allows one to adjust the sensitivity and/or specificity of the diagnostic assay as desired. The particular diagnostic cut-off can be determined, for example, by measuring the amount of the biomarker in a statistically significant number of samples from subjects with different breast cancer statuses, and drawing the cut-off at the desired level of accuracy, sensitivity, and/or specificity. In certain embodiments, the diagnostic cut-off can be determined with the assistance of a classification algorithm, as described herein.

Accordingly, methods are provided for diagnosing breast cancer in a subject, by determining the level of at least one small non-coding RNA in a sample containing circulating small non-coding RNA from the subject, wherein a difference in the level of the at least one small non-coding RNA versus that in a normal subject (as determined relative to a suitable control) is indicative of breast cancer in the subject. In one embodiment, the at least one small non-coding RNA preferably includes one or more small non-coding RNAs from Table 1. In one embodiment, the at least one small non-coding RNA preferably includes one or more small non-coding RNAs from Table 2. In one embodiment, the at least one small non-coding RNA preferably includes one or more small non-coding RNAs from Table 3. For example, the present invention provides a method of determining the level of at least one small non-coding RNA in a sample containing circulating small non-coding RNA derived from the subject, wherein an increase in the level of the at least one small non-coding RNA relative to a control is indicative of breast cancer in the subject.

Optionally, the method may further comprise providing a diagnosis that the subject has or does not have breast cancer based on the level of at least one small non-coding RNA in the sample. In addition or alternatively, the method may further comprise correlating a difference in the level or levels of at least one small non-coding RNA relative to a suitable control with a diagnosis of breast cancer in the subject. In some embodiments, such a diagnosis may be provided directly to the subject, or it may be provided to another party involved in the subject's care.

While individual small non-coding RNA biomarkers are useful in diagnostic applications for breast cancer, as shown herein, a combination of small non-coding RNA biomarkers may provide greater predictive value of breast cancer status than the small non-coding RNA biomarkers when used alone. Specifically, the detection of a plurality of small non-coding RNA biomarkers can increase the accuracy, sensitivity, and/or specificity of a diagnostic test. Exemplary small non-coding RNA biomarkers and biomarker combinations are shown in Table 1. Exemplary small non-coding RNA biomarkers and biomarker combinations are shown in Table 2. Exemplary small non-coding RNA biomarkers and biomarker combinations are shown in Table 3. The invention includes the individual biomarkers and biomarker combinations as set forth in these tables, and their use in methods and kits described herein.

Accordingly, methods are provided for diagnosing breast cancer in a subject, by determining the level of two or more small non-coding RNAs in a sample containing circulating small non-coding RNA from the subject, wherein a difference in the level of the small non-coding RNAs versus that in a normal subject (as determined relative to a suitable control) is indicative of breast cancer in the subject. In one embodiment, the small non-coding RNAs preferably include one or more of a small non-coding RNA shown in Table 1. In one embodiment, the small non-coding RNAs preferably include one or more of a small non-coding RNA shown in Table 2. In one embodiment, the small non-coding RNAs preferably include one or more of a small non-coding RNA shown in Table 3.

Also provided is a method of diagnosing breast cancer in a subject by determining the levels of two or more small non-coding RNAs in a sample containing circulating small non-coding RNA from the subject, comparing the levels of the two or more small non-coding RNAs in the sample to a set of data representing levels of the same small non-coding RNAs present in normal subjects and subjects having breast cancer, and diagnosing the subject as having or not having breast cancer based on the comparison. In such a method, the set of data serves as a suitable control or reference standard for comparison with the sample from the subject.

Comparison of the sample from the subject with the set of data may be assisted by a classification algorithm, which computes whether or not a statistically significant difference exists between the collective levels of the two or more small non-coding RNAs in the sample, and the levels of the same small non-coding RNAs present in normal subjects or subjects having breast cancer.

Generation of Classification Algorithms for Qualifying Cancer Status

In some embodiments, data that are generated using samples such as "known samples" can then be used to "train" a classification model. A "known sample" is a sample that has been pre-classified, e.g., classified as being derived from a normal subject, or from a subject having breast cancer. The data that are derived from the spectra and are used to form the classification model can be referred to as a "training data set." Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased versus non-diseased).

In some embodiments, data for the training data set that is used to form the classification model can be obtained directly from quantitative PCR (for example, Ct values obtained using the double delta Ct method), or from high-throughput expression profiling, such as microarray analysis (for example, total counts or normalized counts from a small non-coding RNA expression assay).

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (support vector machines).

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm. Learning algorithms asserted for use in classifying biological information are described, for example, in PCT International Publication No. WO 01/31580 (Barnhill et al., "Methods and devices for identifying patterns in biological systems and methods of use thereof"), U.S. patent application No. 2002 0193950 A1 (Gavin et al, "Method or analyzing mass spectra"), U.S. patent application No. 2003 0004402 A1 (Hitt et al., "Process for discriminating between biological states based on hidden patterns from biological data"), and U.S. patent application No. 2003 0055615 A1 (Zhang and Zhang, "Systems and methods for processing biological expression data"). The contents of the foregoing patent applications are incorporated herein by reference in their entirety.

The classification models can be formed on and used on any suitable digital computer. Suitable digital computers include micro, mini, or large computers using any standard or specialized operating system, such as a Unix, WINDOWS or LINUX based operating system.

The training data set(s) and the classification models can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

The learning algorithms described above can be used for developing classification algorithms for small non-coding RNA biomarkers for breast cancer. The classification algorithms can, in turn, be used in diagnostic tests by providing diagnostic values (e.g., cut-off points) for biomarkers used singly or in combination.

Additional Diagnostic Tests

The level of small non-coding RNA biomarkers indicative of breast cancer, may be used as a stand-alone diagnostic indicator of breast cancer, in a subject. Optionally, the methods may include the performance of at least one additional test to facilitate the diagnosis of breast cancer. For example, other tests in addition to determining the level of one or more small non-coding RNA biomarkers in order to facilitate a diagnosis of breast cancer, may be performed. Any other test or combination of tests used in clinical practice to facilitate a diagnosis of breast cancer, may be used in conjunction with the small non-coding RNA biomarkers described herein.

Methods of Treatment

In some embodiments, where a subject is diagnosed with breast cancer by the methods described herein, the present invention further provides methods of treating such subjects identified to have breast cancer. Accordingly, in one embodiment, the invention relates to a method of treating breast cancer in a subject, comprising determining the level of at least one small non-coding RNA biomarker in a sample derived from the subject, wherein a difference in the level of at least one small non-coding RNA biomarker versus that in a normal subject as determined relative to a suitable control is indicative of breast cancer in the subject, and administering a therapeutically effective amount of a breast cancer therapeutic to the subject. In another embodiment, the invention relates to a method of treating a subject having breast cancer, comprising identifying a subject having breast cancer in which the level of at least one small non-coding RNA biomarker in a sample derived from the subject is different (e.g., increased) versus that in a normal subject as determined relative to a suitable control, and administering a therapeutically effective amount of a breast cancer therapeutic to the subject.

The term "breast cancer therapeutic" includes, for example, substances approved by the U.S. Food and Drug Administration for the treatment of breast cancer. Drugs approved to treat breast cancer include, but are not limited to, Abemaciclib, Abitrexate (Methotrexate), Abraxane (Paclitaxel Albumin-stabilized Nanoparticle Formulation), Ado-Trastuzumab Emtansine, Afinitor (Everolimus), Anastrozole, Aredia (Pamidronate Disodium), Arimidex (Anastrozole), Aromasin (Exemestane), Capecitabine, Clafen (Cyclophosphamide), Cyclophosphamide, Cytoxan (Cyclophosphamide), Docetaxel, Doxorubicin Hydrochloride, Ellence (Epirubicin Hydrochloride), Epirubicin Hydrochloride, Eribulin Mesylate, Everolimus, Exemestane, 5-FU (Fluorouracil Injection), Fareston (Toremifene), Faslodex (Fulvestrant), Femara (Letrozole), Fluorouracil Injection, Folex (Methotrexate), Folex PFS (Methotrexate), Fulvestrant, Gemcitabine Hydrochloride, Gemzar (Gemcitabine Hydrochloride), Goserelin Acetate, Halaven (Eribulin Mesylate), Herceptin (Trastuzumab), Ibrance (Palbociclib), Ixabepilone, Ixempra (Ixabepilone), Kadcyla (Ado-Trastuzumab Emtansine), Kisqali (Ribociclib), Lapatinib Ditosylate, Letrozole, Megestrol Acetate, Methotrexate, Methotrexate LPF (Methotrexate), Mexate (Methotrexate), Mexate-AQ (Methotrexate), Neosar (Cyclophosphamide), Neratinib Maleate, Nerlynx (Neratinib Maleate), Nolvadex (Tamoxifen Citrate), Paclitaxel, Paclitaxel Albumin-stabilized Nanoparticle Formulation, Palbociclib, Pamidronate Disodium, Perjeta (Pertuzumab), Pertuzumab, Ribociclib, Tamoxifen Citrate, Taxol (Paclitaxel), Taxotere (Docetaxel), Thiotepa, Toremifene, Trastuzumab, Tykerb (Lapatinib Ditosylate), Velban (Vinblastine Sulfate), Velsar (Vinblastine Sulfate), Verzenio (Abemaciclib), Vinblastine Sulfate, Xeloda (Capecitabine), Zoladex (Goserelin Acetate).

The breast cancer therapeutics may be administered to a subject using a pharmaceutical composition. Suitable pharmaceutical compositions comprise a pharmaceutically effective amount of a breast cancer therapeutic (or a pharmaceutically acceptable salt or ester thereof), and optionally comprise a pharmaceutically acceptable carrier). In certain embodiments, these compositions optionally further comprise one or more additional therapeutic agents.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J. Pharmaceutical Sciences, 66:1-19 (1977), incorporated herein by reference. The salts can be prepared in situ during the final isolation and purification of the compounds of the invention, or separately by reacting a free base or free acid function with a suitable reagent. For example, a free base function can be reacted with a suitable acid. Furthermore, where the compounds carry an acidic moiety, suitable pharmaceutically acceptable salts thereof may, include metal salts such as alkali metal salts, e.g. sodium or potassium salts; and alkaline earth metal salts, e.g. calcium or magnesium salts.

The term "pharmaceutically acceptable ester", as used herein, refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms.

As described above, the pharmaceutical compositions may additionally comprise a pharmaceutically acceptable carrier. The term carrier includes any and all solvents, diluents, or other liquid vehicle, dispersion or suspension aids, surface active agents, isotonic agents, thickening or emulsifying agents, preservatives, solid binders, lubricants and the like, suitable for preparing the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Compositions for use in the present invention may be formulated to have any concentration of the breast cancer therapeutic desired. In preferred embodiments, the composition is formulated such that it comprises a therapeutically effective amount of the breast cancer therapeutic.

The disclosure generally relates to a method of diagnosing a subject with a benign, pre-malignant, or malignant hyperproliferative cell comprising: detecting the presence, absence, and/or quantity of at least one non-coding RNA or functional fragment thereof in a sample. In some embodiments, the step of detecting comprise exposing a sample from a subject (e.g. a human subject), to one or a plurality of probes, each probe capable of binding one or a plurality of non-coding RNA molecules in the sample. In some embodiments, the probe is a nucleic acid molecule (DNA, RNA or hybrid thereof) that comprises at least 70%, 80%, 85%, 90%, 95%, 96%, 97%, 98%, 99% sequence homology or sequence identity to any nucleic acid sequences of Tables 1, 2, and/or 3. In some embodiments, the probe is a nucleic acid molecule (DNA, RNA or hybrid thereof) that comprises at least 70%, 80%, 85%, 90%, 95%, 96%, 97%, 98%, 99% sequence homology or sequence identity to SEQ ID NO:3, SEQ ID NO:19, SEQ ID NO:32, SEQ ID NO:40, SEQ ID NO: 41, SEQ ID NO:79, SEQ ID NO:82, SEQ ID NO: 83, SEQ ID NO: 126, SEQ ID NO: 148, or SEQ ID NO:191. In some embodiments, the probe is a nucleic acid molecule (DNA, RNA or hybrid thereof) that is an RNA sequence comprising at least 70%, 80%, 85%, 90%, 95%, 96%, 97%, 98%, 99% sequence homology or sequence identity to SEQ ID NO:3, SEQ ID NO: 19, SEQ ID NO:32, SEQ ID NO:40, SEQ ID NO:41, SEQ ID NO:79, SEQ ID NO: 82, SEQ ID NO:83, SEQ ID NO: 126, SEQ ID NO: 148, or SEQ ID NO:191, where each thymine is replaced with a uracil. In some embodiments, the plurality of probes are one or a combination of nucleic acid sequences that are an RNA complementary to the a nucleic acid sequence comprising at least 70%, 80%, 85%, 90%, 95%, 96%, 97%, 98%, 99% sequence homology or sequence identity to SEQ ID NO:3, SEQ ID NO: 19, SEQ ID NO:32, SEQ ID NO: 40, SEQ ID NO:41, SEQ ID NO: 79, SEQ ID NO: 82, SEQ ID NO: 83, SEQ ID NO: 126, SEQ ID NO:148, or SEQ ID NO:191. In some embodiments, the plurality of probes are one or a combination of nucleic acid sequences chosen from: SEQ ID NO:3, SEQ ID NO: 19, SEQ ID NO:32, SEQ ID NO:40, SEQ ID NO:41, SEQ ID NO:79, SEQ ID NO: 82, SEQ ID NO: 83, SEQ ID NO: 126, SEQ ID NO: 148, or SEQ ID NO: 191. In some embodiments, the plurality of probes are one or a combination of nucleic acid sequences complementary to the nucleic acid sequences chosen from: SEQ ID NO:3, SEQ ID NO: 19, SEQ ID NO:32, SEQ ID NO: 40, SEQ ID NO:41, SEQ ID NO: 79, SEQ ID NO: 82, SEQ ID NO: 83, SEQ ID NO: 126, SEQ ID NO: 148, or SEQ ID NO: 191.

In any of the disclosed method embodiments, the subject may be a human diagnosed with or suspected as having a breast cancer. In any of the disclosed method embodiments, wherein the step of detecting is preceded by a step of acquiring a sample from the subject.

In some embodiments, the probe or plurality of probes are one or a plurality of antibodies or antibody fragments comprising a CDR that binds to a nucleic acid molecule (DNA, RNA or hybrid thereof) that comprises at least 70%, 80%, 85%, 90%, 95%, 96%, 97%, 98%, 99% or 100% sequence homology or sequence identity to SEQ ID NO:3, SEQ ID NO: 19, SEQ ID NO:32, SEQ ID NO:40, SEQ ID NO:41, SEQ ID NO: 79, SEQ ID NO: 82, SEQ ID NO: 83, SEQ ID NO: 126, SEQ ID NO: 148, or SEQ ID NO: 191. In some embodiments, the probe or plurality of probes are one or a plurality of antibodies or antibody fragments comprising a CDR that binds to a nucleic acid molecule (DNA, RNA or hybrid thereof) that comprises at least 70%, 80%, 85%, 90%, 95%, 96%, 97%, 98%, 99% or 100% sequence homology or sequence identity to SEQ ID NO:3, SEQ ID NO: 19, SEQ ID NO:32, SEQ ID NO:40, SEQ ID NO:41, SEQ ID NO:79, SEQ ID NO: 82, SEQ ID NO: 83, SEQ ID NO: 126, SEQ ID NO:148, or SEQ ID NO:191, wherein each of sequences are modified such that the thymines in each of SEQ ID NO:3, SEQ ID NO: 19, SEQ ID NO:32, SEQ ID NO: 40, SEQ ID NO:41, SEQ ID NO:79, SEQ ID NO: 82, SEQ ID NO: 83, SEQ ID NO: 126, SEQ ID NO:148, or SEQ ID NO:191 are replaced with a uracil. In some of the embodiments, the methods further comprise isolating RNA from the sample before exposing the sample to one or a plurality of probes. In some embodiments, the method comprises detecting or quantifying an amount of non-coding RNAs, such as small RNAs (smRNAs), in a sample by performing semiquantitative or quantitative PCR or sequencing analysis of the non-coding RNAs in a sample. Probes may be immobilized to a solid support such as an ELISA plate, plastic, slide, microarray, silica chip or other surface such that the single-strand nucleotide sequences are exposed to a sample comprising non-coding RNAs from a subject. The probes may comprise, in some embodiments, from about 5 to bout 100 nucleotides in length and comprise any of the sequences in Tables 1, 2, and/or 3 or any complementary sequence in RNA or DNA of the sequences set forth in Tables 1, 2, and/or 3. In any of the disclosed method embodiments, the step of detecting the presence, absence, and/or quantity of at least one non-coding RNA or homologous sequence thereof at least 70% homolgous to one of the noncoding RNAs in a sample comprises using a chemiluminescent probe, fluorescent probe, and/or fluorescence microscopy, calculating the presence or quantity by correlating the signal of the detectable probe to the presence of the non-coding RNA.

The disclosure generally relates detecting the presence of T3p in a sample and correlating the presence of the T3p in the sample with the presence of breast cancer. The disclosure also relates to detecting the presence of a nucleic acid molecule (DNA, RNA or hybrid thereof) that comprises, consists of or consists essentially of at least 70%, 80%, 85%, 90%, 95%, 96%, 97%, 98%, 99% or 100% sequence homology or sequence identity to SEQ ID NO:3, SEQ ID NO: 19, SEQ ID NO:32, SEQ ID NO:40, SEQ ID NO:41, SEQ ID NO:79, SEQ ID NO:82, SEQ ID NO: 83, SEQ ID NO: 126, SEQ ID NO: 148, or SEQ ID NO: 191 or an RNA molecule thereof wherein one or more of the thymines in any of the sequence identifiers are replaced by uracil. In some embodiments, the probe or plurality of probes on a solid support comprise a sequence complementary to SEQ ID NO:3, SEQ ID NO: 19, SEQ ID NO:32, SEQ ID NO:40, SEQ ID NO:41, SEQ ID NO:79, SEQ ID NO:82, SEQ ID NO:83, SEQ ID NO: 126, SEQ ID NO: 148, or SEQ ID NO: 191 that is from about 5 to about 1000 nucleotides in length. In some embodiments, the probe or plurality of probes on a solid support comprise a sequence complementary to SEQ ID NO:3, SEQ ID NO:19, SEQ ID NO:32, SEQ ID NO:40, SEQ ID NO:41, SEQ ID NO:79, SEQ ID NO: 82, SEQ ID NO: 83, SEQ ID NO: 126, SEQ ID NO: 148, or SEQ ID NO: 191 that is from about 5 to about 500 nucleotides in length. In some embodiments, the probe or plurality of probes on a solid support comprise a sequence complementary to SEQ ID NO:3, SEQ ID NO: 19, SEQ ID NO: 32, SEQ ID NO:40, SEQ ID NO:41, SEQ ID NO: 79, SEQ ID NO: 82, SEQ ID NO: 83, SEQ ID NO:126, SEQ ID NO: 148, or SEQ ID NO:191 that is from about 5 to about 100 nucleotides in length. In some embodiments, the probe or plurality of probes on a solid support comprise a sequence complementary to SEQ ID NO:3, SEQ ID NO:19, SEQ ID NO: 32, SEQ ID NO:40, SEQ ID NO:41, SEQ ID NO: 79, SEQ ID NO:82, SEQ ID NO: 83, SEQ ID NO: 126, SEQ ID NO:148, or SEQ ID NO: 191 that is from about 5 to about 50 nucleotides in length.

In some embodiments, any of the methods disclosed herein further comprise a step of correlating the presence or quantity of non-coding RNAs such as those disclosed in Tables 1, 2, and/or 3 or any combination thereof to the likelihood that the subject has cancer, such as breast cancer.

Kits for Detection Small RNA Biomarkers

In another aspect, the present invention provides kits for diagnosing breast cancer status in a subject, which kits are useful for determining the level of one or more of a small non-coding RNA biomarkers from Table 1, Table 2 or Table 3 (wherein the sequences optionally comprise uracils in place of one, more than one or all of the disclosed thymines), and combinations thereof. In one embodiment, the one or more small non-coding RNAs are selected from the biomarkers listed in Table 1. In one embodiment, the one or more small non-coding RNAs are selected from the biomarkers listed in Table 2. In one embodiment, the one or more small non-coding RNAs are selected from the biomarkers listed in Table 3. Kits may include materials and reagents adapted to selectively detect the presence of a small non-coding RNA or group of small non-coding RNAs diagnostic for breast cancer in a sample derived from a subject. For example, in one embodiment, the kit may include a reagent that specifically hybridizes to a small non-coding RNA. Such a reagent may be a nucleic acid molecule in a form suitable for detecting the small noncoding RNA, for example, a probe or a primer. The kit may include reagents useful for performing an assay to detect one or more small non-coding RNAs, for example, reagents which may be used to detect one or more small non-coding RNAs in a qPCR reaction. The kit may likewise include a microarray useful for detecting one or more small non-coding RNAs.

In a further embodiment, the kit may contain instructions for suitable operational parameters in the form of a label or product insert. For example, the instructions may include information or directions regarding how to collect a sample, how to determine the level of one or more small non-coding RNA biomarkers in a sample, or how to correlate the level of one or more small non-coding RNA biomarkers in a sample with the breast cancer status of a subject.

In another embodiment, the kit can contain one or more containers with small non-coding RNA biomarker samples, to be used as reference standards, suitable controls, or for calibration of an assay to detect the biomarkers in a test sample.

Other embodiments are described in the following non-limiting Examples. Various publications, including patents, published applications, technical articles and scholarly articles are cited throughout the specification. Each of these cited publications is incorporated by reference herein in its entirety.

Examples

Example 1. Methods

Examples 2-6 were carried out with methods including, but not limited to, the following:
Tissue Culture
MDA-MB-231 and MDA-LM2 cells were cultured in Dulbecoco's medium supplemented with 10% fetal bovine serum, L-glutamine, sodium pyruvate, penicillin-streptomycin, and amphotericin. Cell lines were obtained from American Type and Culture Collection (ATCC) and were grown according to protocol.

All cells were cultured in a 37° C., 5% $CO_2$ humidified incubator. Cell lines MDA-MB-231, MDA-LM2, CN34-par, CN34-Lm1a, MCF7 and MDA-MB-453 were propagated in DMEM base media supplemented with 4.5 g/L glucose, 10% FBS, 4 mM L-glutamine, 1 mM sodium pyruvate, penicillin (100 units/mL), streptomycin (100 g/mL) and amphotericin (1 µg/mL). Cell lines HCC1395, ZR-75-1 and HCC38 were propagated in RPMI 1640 base media supplemented with 10% FBS, 2 mM L-glutamine, penicillin (100 units/mL), streptomycin (100 µg/mL) and amphotericin (1 µg/mL). SK-BR-3 cell line was propagated in McCoy's 5a modified media supplemented with 10% FBS, penicillin (100 units/mL), streptomycin (100 µg/mL) and amphotericin (1 µg/mL). HMECs were obtained from Thermo Fisher Scientific and propagated in HuMEC ready media (Thermo Fisher Scientific).

Small and Exosomal RNA Extraction and Sequencing: Preparation of conditioned media for isolation of RNA from extracellular vesicle and total conditioned media was carried out by seeding cells at $7 \times 10^5$. 24 hours later, cells were washed twice with PBS and 10 mL exosome-depleted media was added. 48 hours later, media was harvested by spinning at 200×g for 15 minutes and taking the supernatant. Exosome-depleted media was prepared by substituting exosome-depleted FBS (Thermo Fisher Scientific) for FBS. Exosome-depleted HMEC media was prepared by centrifuging the bovine pituitary extract media component at 100,000×g at 4° C. for 16 hours.

Extracellular vesicle RNA was isolated from 5 mL conditioned media, prepared as outlined above, using the Cell Culture Media Exosome Purification and RNA Isolation kit (Norgen Biotek). RNA from conditioned media was isolated from 400 ul total conditioned media using the miRNeasy serum/plasma kit (Qiagen). Total cellular small RNA samples were extracted using Norgen Biotek small RNA purification kit according to the manufacturer's protocol. RNA samples were subsequently prepared for high-throughput sequencing with the NEXTflex Small RNA Sequencing Kit v3 using the manufacturer's protocol (Bioo Scientific). The resulting libraries were then sequenced and processed as recommended by the manufacturer. Briefly, cutadapt (v1.4) was used to remove the adapter sequences and trim the degenerate sequences at the beginning and end of each read. We then used bowtie2 (v2.3.3) to align the resulting sequences to the human genome (build hg38). The resulting BAM files were then sorted and converted to BED for further analysis. Extracellular vesicle RNA was isolated from serum samples using the Plasma/serum Exosome Purification and RNA isolation kit (Norgen Biotek) according to the manufacturer's instructions.

TCGA-BRCA small RNA sequencing data and identification of oncRNAs Reads from the TCGA-BRCA project were downloaded from the Genomic Data Commons (GDC) in BAM format (hg38) and the samples were annotated using the GDC API. Upon conversion to the BED format, the Piranha package[40] was used to identify the expressed small RNA loci. The resulting loci were merged across all samples using mergeBed to create a comprehensive list of small RNA loci expressed in breast tissue and breast cancer.

By enumerating the small RNA sequences obtained from breast cancer cell lines and HMECs, we generated a count table for each small RNA locus. We then normalized the resulting table by library size and retained only those loci with no observed reads across the three HMEC replicates. We used two independent statistical tests to compare either all cancer cell lines or each subtype individually (TNBC, HER2+, and Luminal): (i) we used the DESeq package in R to calculate an adjusted p-value, and (ii) we used Fisher's exact test to compare presence and absence of each small RNA. We selected those loci with either an adjusted P<0.05 in the former or P<0.1 in the latter test across all comparisons.

Four thirty-seven loci, listed in FIG. 1A, satisfied these criteria. For visualization, we max-normalized each row and performed a k-means clustering (k=3). For the TCGA-BRCA database, we generated a similar count table across all subtype annotated samples (based on PAM50 classification) and all small RNA loci and normalized the resulting table to generate a count-per-million reads (cpm) table. In order to identify 'orphan' small RNAs, i.e. small RNAs that are largely absent in normal cells, we first retained only the loci with their $90^{th}$ percentile expression in normal samples below 0.5 cpm. Of the 437 loci above, 268 passed this step. We then performed Fisher's exact tests to compare the presence of all small RNAs across the tumor samples and normal biopsies. We performed similar comparisons between normal samples and each of the breast cancer subtypes. We then retained those loci that were significant in at least one of these tests with an adjusted p-value of <0.05. 201 of small RNAs satisfied this final step and were thus classified as orphan non-coding RNAs. We confirmed that none of these small RNAs were previously annotated as miRNAs, snoRNA, or tRNAs.

Small RNA Sequencing of PDX Models and Normal Epithelial Samples:

All human samples used to generate PDX tumors, as well as the human non-tumor samples, were previously described. Small RNA profiling and data pre-processing was carried out by Q²Solutions. The abundance of oncRNAs these samples was determined as described above.

Comparing oncRNA Expression Between Poorly and Highly Metastatic Cells

Figure 1B:
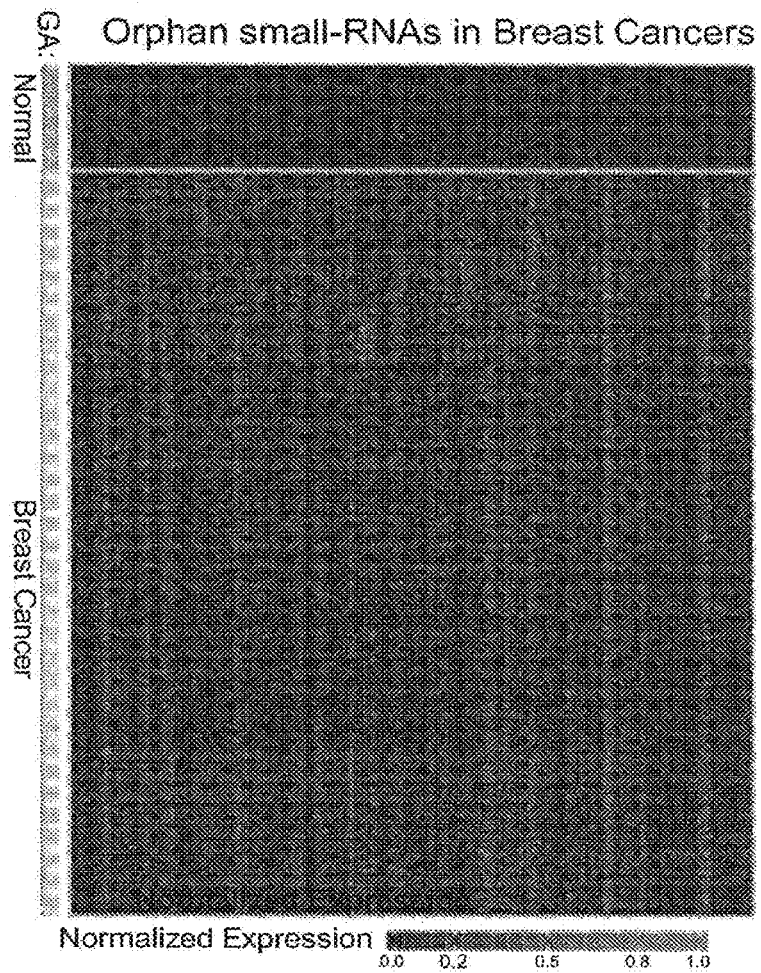

We used the R package DESeq2 to compare expression of oncRNAs between parental cell lines in FIG. 1 (MDA231 and CN34) and their highly metastatic in vivo selected derivatives (MDA-MB-231 background) to identify those oncRNAs that were significantly upregulated in highly metastatic cells. We identified T3p in this analysis, which we also confirmed in a small RNA dataset we had previously generated for these lines[7]. In addition, we also performed quantitative RT-PCR assays. For this, we extracted small RNAs from MDA-231 parental cells and their highly metastatic MDA-LM2 (microRNA Purification Kit; Norgen) and performed stem-loop qPCR, using the following primers: R: 5'-CCAGTGCAGGGTCCGAGGTA (SEQ ID NO:202) and F: 5'-CCCAGGACTCGGCTCACAC (SEQ ID NO:203).

T3p Expression and Clinical Association in the TCGA-BRCA Dataset

We used the metadata accompanying the TCGA-BRCA dataset to perform survival analysis based on T3p expression in tumor samples. We stratified the patients based on T3p levels and generated Kaplan-Meier curves using all tertiles and performed log-rank (Mantel-Cox) test to calculate the associated p-value. We similarly used the clinical data to compare T3p expression across early and late stage tumors (one-tailed Mann-Whitney U-test). T3p modulation and gene expression profiling: We used miRCURY LNA inhibitors (Exiqon) against the following sequences: T3p: CAGGACTCGGCTCACACATGC (SEQ ID NO: 204); TERC: TTGTCTAACCCTAACTGAGAAGG (SEQ ID NO:205); Scrambled: AGACGACAGCTGGATCACACG (SEQ ID NO:206). Similarly, we used T3p mimetics (IDT): rC*rArGrGrArCrUrCrG rGrCrUrCrArCrArCrArUrG*rC (T3p mimetic) (SEQ ID NO:207) and rA*rGrA rCrGrA rCrArG rCrUrG rGrArU rCrArC rArC*rG (control) (SEQ ID NO:208). We then transfected the LNAs in the highly metastatic MDA-LM2 cells and the mimetics in the parental MDA-MB-231 cells and performed gene expression profiling as previously described[7]. Differential gene expression analysis was also performed as previously described[7].

Tough Decoys and In Vivo Lung Colonization and Tumor Growth Assays

MDA-LM2 cells were transfected with anti-T3p or scrambled LNA (same as above) and after 48 hours, cells were injected via tail-vein into the vasculature of immunocompromised NOD SCID gamma (NSG) mice ($2.5 \times 10^4$ per mouse; n=5 per cohort). In vivo imaging and comparison of curves was performed as previously described[19]. Lungs from at least three mice per cohort (middle signal) were then extracted, fixed, sectioned, stained (H&E) and quantified as previously described[19].

To generate stable inhibition of T3p, we designed TuDs against this small RNA in a lentiviral backbone under a RNA PolIII promoter (pLKO.1). We then stably transduced MDA-LM2 cells and performed lung colonization assays (same as above; $5 \times 10^4$ cells per mouse). HCC1395 cells were similarly transduced and injected at $2 \times 10^5$ cells per mouse. Orthotopic tumor growth assays were performed by injecting $2.5 \times 10^5$ cells resuspended in 50 ul PBS mixed with 50 ul matrigel into the mammary glands of age-matched 6-8 week old female NOD/SCID gamma mice using a 28 gauge needle. Tumor volume was determined by using calipers to measure the tumor length (L) and width (W) every two days and calculated using the formula $\pi LW2/6$. The experiment endpoint was reached once tumors reached a volume of 800 mm³. Cell proliferation In vitro: cancer cell proliferation assays are performed by seeding $5 \times 10^4$ cells at day 0 and then counting them in triplicate on day 3 and day 5. The slope of the best fitted line, estimated using linear models, between log of cell counts and days is the reported proliferation rate (days$^{-1}$). For cell-cycle analysis, cells were grown to 80% confluency in 6 cm plates, harvested and fixed in 70% ethanol. Cells were then pelleted and resuspended in 50 μg/mL propidium iodide (Thermo Fisher Scientific) and 1 mg/mL RNase A (Thermo Fisher Scientific) and allowed to incubate 1 hour at 37° C. BD Aria2 flow cytometer was then used for FACS analysis; post-FACS analysis and cell cycle quantification was performed using the python package 'fcsparser'.

Co-expression analysis for finding T3p biogenesis factors: In order to identify the regulators of T3p biogenesis, we listed the genes with known nuclease activity (GO: 0004540 and GO: 0004525) and further added RNA-binding proteins that are known to interact with these nucleases. We then performed co-expression analysis between T3p levels and those of the genes on this list across the TCGA-BRCA dataset. We overlapped the genes with strong associations with those that are upregulated in highly metastatic MDA-LM2 cells and are similarly higher in breast cancer samples relative to normal biopsies in the TCGA-BRCA dataset. Based on these criteria, we identified seven candidates, two of which had known double-stranded binding activity. Since the CR7 domain of TERC is structured (i.e. form double-stranded regions), we reasoned that these proteins, namely DROSHA and TARBP2, were the best candidates for follow-up. We used siRNAs to knockdown DROSHA and TARBP2, and also DGCR8 and DICER1 that are known to interact with these proteins respectively (IDT). We used the following target sequences: TARBP2: 5'-ACCTGGGAT-TCTCTACGAAATTCAGT (SEQ ID NO:209), DROSHA: 5'-CCTTGATTGAGGTATAGTTCTTGTCT (SEQ ID NO:210), DICER1: 5'-TGGTGCT-TAGTAAACTCTTGGTTCCA (SEQ ID NO:211), and DGCR8: 5'-CTGCAGGAGTAAGGACAGGAAGGTGC (SEQ ID NO:212). Following siRNA transfection and knockdown verification, we performed small RNA sequencing as described above.

Training and testing of oncRNA-based classifiers: Of the 201 oncRNAs, 100 were detected in at least one serum sample. We used these 100 oncRNAs to train a GBC on subtype-annotated TCGA-BRCA samples (sklearn module). We then bootstrapped our compendium of serum samples from 35 healthy and 40 cancer patients 100 times to calculate the performance parameters of the classifier, namely average AUROC, precision, and accuracy scores. We also performed an independent assessment of oncRNAs by performing training and testing on the serum data as opposed to TCGA-BRCA (5-fold cross-validation). We used the following miRNAs to perform similar analyses as above: miR-10b-5p, miR-10b-3p, miR-148b-3p, miR-148b-5p, miR-155-3p, miR-155-5p, miR-34a-3p, miR-376a-3p, miR-652-3p, miR-133a-3p, miR-139-3p, miR-143-3p, miR-145-3p, miR-15a-3p, miR-18a-3p, miR-425-3p, miR-34a-5p, miR-376a-5p, miR-652-5p, miR-133a-5p, miR-139-5p, miR-143-5p, miR-145-5p, miR-15a-5p, miR-18a-5p, miR-425-5p, miR-127-3p, miR-194-5p, miR-205-5p, miR-21-5p, miR-375, miR-376c-3p, miR-382-5p, miR-409-3p, and miR-411-5p. Animal Studies: All animal studies were completed according to University of California San Francisco IACUC guidelines. Statistical Methods: Statistical tests used to assess data significance are described in the legends. Briefly, unless otherwise stated, we have used non-parametric tests to perform pair-wise comparisons. For mouse experiments, we have used two-way ANOVA with time as a co-variate. For proliferation rates, we have used linear models. The analyses were performed in python, R, and prism environments.

Example 2. A Systematic Search for Orphan Small Non-Coding RNAs in Breast Cancer To search for a new class of cancer-specific small-RNAs that are expressed in breast cancer cells, yet are undetectable in normal breast tissue, an unbiased approach was used based on small RNA sequencing of multiple breast cancer subtypes as well as human mammary epithelial cells. Roughly 200 previously unknown small RNAs were discovered and annotated that are specifically expressed in breast cancer cells. Borrowing terminology from bacterial genetics, these RNAs have been named 'orphan' non-coding RNAs (oncRNAs) to highlight their cancer-specific biogenesis.

It was first determined if a set of small RNAs exists that are only present in cancer cells and can provide an accessible pool of potential regulators in these cells. It was reasoned that such oncRNAs would only be detectable in cancer cell lines and not in normal cells. To test this hypothesis, small RNA sequencing was performed on nine breast cancer cell lines (representing all major breast cancer subtypes) as well as human mammary epithelial cells (HMEC) as a reference. 437 unannotated small RNAs were identified that were significantly detected across all of the breast cancer lines while remaining undetected in HMEC samples (FIG. 1A).

Figure 2A:
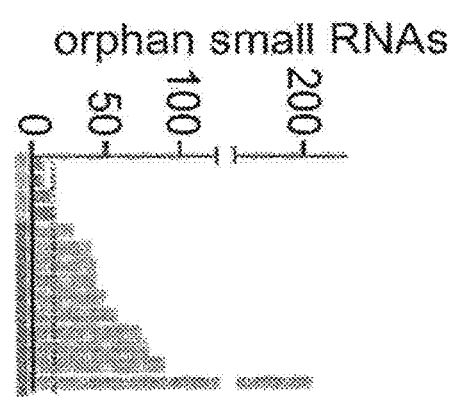
FIG. 2A and FIG. 2B show that orphan small RNAs are relatively abundant in cancer cells and are largely undetected in normal tissue.

To further narrow the search and strengthen these findings, a similar analysis was performed on the small RNA sequencing data obtained from The Cancer Genome Atlas (TCGA), which provided small RNA expression profiles across roughly 200 normal tissue samples and 1200 breast cancer biopsies. In this analysis, 268 cancer-specific small RNAs were identified, 201 of which were also present in the analysis of breast cancer lines. The highly significant overlap between these two independent analyses revealed a high-confidence set of 201 oncRNAs (FIG. 1B and FIG. 2A), shown in Table 1, below.

TABLE 1

| Chromosome Location | Start on Chromosome | End on Chromosome | OncRNA ID | Chromosome strand | SEQ ID NO | Nucleotide Sequence |
|---|---|---|---|---|---|---|
| chr1 | 6554450 | 6554500 | tag_281 | − | 1 | GGCGGACTCGGGACTGCTGCTAAAGCGGG GTTCCTGCCGTTCCACTTGGC |
| chr1 | 9690200 | 9690250 | tag_390 | + | 2 | GGGTGGCAGACCCAGATCCTGAGGTCCTG CGGCTTCCTCCCCGGGGAGC |
| chr1 | 20787250 | 20787300 | tag_860 | − | 3 | GGCGGCTGGGACTGGAGGACAGCGGTGGC GGAGGCGACTAGCGGCGGCGG |
| chr1 | 28914600 | 28914650 | tag_1217 | + | 4 | GCTCGCTCGCTCCCTCCCTCCGCTGGTGC GTTTAGTCAGTCAGCCAGCAG |
| chr1 | 55126400 | 55126450 | tag_2286 | + | 5 | GCTTCCTTCTTTATTTTTCTCTACAGCTC TCCTCACCATCTGACACATAC |
| chr1 | 103470900 | 103470950 | tag_3856 | + | 6 | TTTTACAAGCCATTTCTGAGATGGGAAAC TATTAGGTCAGTGCAAAAGTG |
| chr1 | 110019500 | 110019550 | tag_4074 | + | 7 | GTCTAAGAAATATTTTTGTGCTTTCTGGC CTTCTTTTCCCACCTTAGGCT |
| chr1 | 120723950 | 120724000 | tag_4510 | + | 8 | ACTTCCGGCGGCGGCTGAGGCGGCGGCCG AGGAGCGGCGGACTCGGGCG |
| chr1 | 149888200 | 149888250 | tag_4908 | + | 9 | TCAAACAAAATACTGGTTTTGTTTTACTG AGAGGCACTGTGGGTTTTTGT |
| chr1 | 151372650 | 151372700 | tag_5001 | − | 10 | AGCGGCCTCTGACACCAGCACAGCAAACC CGCCGGGATCAAAGTGTACCA |
| chr1 | 153968100 | 153968150 | tag_5136 | − | 11 | CGGTAGGGCCGCTGTATCTGGGAGTAGGG GACTAAGAGTCTGAGGGTCCA |
| chr1 | 154975050 | 154975100 | tag_5206 | + | 12 | TACTGACCACCCTCACCCATGAGGCTTTC TGGATCATTCTCTGAACTTTA |
| chr1 | 155063750 | 155063800 | tag_5214 | + | 13 | TTGTACCTTTCTCTCCTCGACTGTGAAGC GGGCCGGGACCTGCCAGGCCA |
| chr1 | 162157100 | 162157150 | tag_5638 | + | 14 | ATGGGGCTGGCTGGTTGTGGGATCTGGAG GCATCTGGGGTTGGAATGTGA |
| chr1 | 162497850 | 162497900 | tag_5657 | + | 15 | GGCTGCTTGAAGTCCCGGGAGTCGGTGAG GCGGCTGCAGGTCCCTCCCTG |

TABLE 1-continued

| Chromosome Location | Start on Chromosome | End on Chromosome | OncRNA ID | Chromosome strand | SEQ ID NO | Nucleotide Sequence |
|---|---|---|---|---|---|---|
| chr1 | 164559150 | 164559200 | tag_5733 | + | 16 | CTGTATATGTTTCTGGAGTCCTGAGCCTGAGCTAAACAAAAGCAGGAGGC |
| chr1 | 164589500 | 164589550 | tag_5737 | − | 17 | TCTGGAAGAAGTAATTTGCTCTATGGTTCTCTGGTGTCCTGAAAAGTGTA |
| chr1 | 167935950 | 167936000 | tag_5869 | − | 18 | GGTTCACAGCGGGCAGGGAAAGCCGCGGGAAGGGTACTCCAGGCGAGAGG |
| chr1 | 174159550 | 174159600 | tag_6119 | + | 19 | TGGCGGAGCGAACGGGACCGGCCCGGCTTCAGAGCGCGAGGTGGAGGGTG |
| chr1 | 182589200 | 182589250 | tag_6440 | − | 20 | GCAGGAGGAAACTGCTCGGGCTGCAAGCAGTCTTCCAGGCTTTGCGGCTG |
| chr1 | 211260850 | 211260900 | tag_7552 | − | 21 | CGCAAGCTGGGTTGGCAGAGGACGCTGGAACCTGGCTGGTCGGGAGAAA |
| chr1 | 222618100 | 222618150 | tag_7990 | + | 22 | TGACCACAACATGGCTGCGGCGCCTGGGCTGCTCGTCTGGCTGCTCGTGC |
| chr1 | 224378600 | 224378750 | tag_8061 | + | 23 | GGAACATCTGAATGCTGAGGCCTAGAGATCGTTCAGGGTGTTGTAACTGGGAACATCTGAATGCTGAGGCCTAGAGATCGTTCAGGGTGTTGTAACTGGGAACATCTGAATGCTGAGGCCTAGAGATCGTTCAGGGTGTTGTAACTGGGA |
| chr1 | 226940300 | 226940350 | tag_8179 | + | 24 | TCCGGAGCGCGTGGCGGGCGTCAGCGCGGTGGCCAGCGCGCAGAGGCGGG |
| chr1 | 228458100 | 228458150 | tag_8247 | + | 25 | GCGTTTCTGTTTGGAGAGACTCAGCCATCATGCCAGACCCGTCCAAATCG |
| chr1 | 235450000 | 235450050 | tag_8590 | − | 26 | TGTTTGCACAAATTTCCTTAAAAATCAACTTGTACTGTAGCATAAGAAAA |
| chr1 | 239459700 | 239459750 | tag_8751 | − | 27 | CTTTATGGCACTGGTAGACAAAACTATCAACTGTGTTAAAATAATTCTAG |
| chr1 | 245513450 | 245513500 | tag_8967 | − | 28 | CTGCCCTTATCAGTTTTGACCTGCTAGGTGCTTCACAGAACTTTGCTTGA |
| chr10 | 8074750 | 8074900 | tag_9414 | + | 29 | TCATCATATTATACAGACCGAACTGTTGTATAAATTTATTTACTGCTAGTCTTAAGAACTGCTTTCTTTCGTTTGTTTGTTTCAATATTTTCCTTCTCTCTCAATTTTTGGTTGAATAAACTAGATTACATTCAGTTGGCCTAAGGTGGT |
| chr10 | 42843200 | 42843250 | tag_10565 | + | 30 | CCAGCCTGAGCAACATAGCGAGACCCCGTGTCTCTTTTTTTTTTTTTTTT |
| chr10 | 47570550 | 47570600 | tag_10732 | + | 31 | GTGGGAGGATCACTTGAGCCCGGAAGTTCAAGACCACCCTAGGCAATATA |
| chr10 | 89306850 | 89306900 | tag_12154 | + | 32 | ATGAATCTAAGAGAGAATGGAATGTATGGGAAAACAAAGTTACTGCAACT |
| chr10 | 98879600 | 98879650 | tag_12513 | + | 33 | AATAAATATGCATTCTCTTATTGGAGCAGGCAGCCAGGAATGTAGAGCTC |
| chr11 | 1256600 | 1256650 | tag_13943 | + | 34 | GGACTCACGTGGATGACAGTGGAGGCCTCCTGGATCTCTAGGTCTCAGGG |
| chr11 | 67464850 | 67464900 | tag_16543 | + | 35 | AGACACCTGCGGGAGGGACCAGAGCCCGGTCAGGGCGAGGGGCGGAGGC |
| chr11 | 70203300 | 70203350 | tag_16694 | + | 36 | TGTCGATTTCCTGTAGTGAATCAGGCACCGGAGTGCAGGTTCGGGGTGG |
| chr11 | 112677900 | 112677950 | tag_18237 | − | 37 | CCCCCGCCACTGCTGAATTTGACTGGCTATAAAAATAAATAAATAAATCCA |
| chr11 | 134609150 | 134609200 | tag_19163 | − | 38 | TCCTTGATGTATAAAAATTAACAAAAATAATTTTACTTGTGGCAATGTTC |

TABLE 1-continued

| Chromosome Location | Start on Chromosome | End on Chromosome | OncRNA ID | Chromosome strand | SEQ ID NO | Nucleotide Sequence |
|---|---|---|---|---|---|---|
| chr12 | 6537600 | 6537950 | tag_19454 | + | 39 | CACTGCCACCCAGAAGACTGTGGATGGCCCCTCCGGGAAACTGTGGCGTGATGGCCGCGGGGCTCTCCAGAACATCATCCCTGCCTCTACTGGCGCTGCCAAGGCTGTGGGCAAGGTCATCCCTGAGCTGAACGGGAAGCTCACTGGCATGGCCTTCCGTGTCCCCACTGCCAACGTGTCAGTGGTGGACCTGACCTGCCGTCTAGAAAAACCTGCCAAATATGATGACATCAAGAAGGTGGTGAAGCAGGCGTCGGAGGGCCCCCTCAAGGGCATCCTGGGCTACACTGAGCACCAGGTGGTCTCCTCTGACTTCAACAGCGACACCCACTCCTCCACCTTTGACGCTG |
| chr12 | 29394350 | 29394400 | tag_20390 | + | 40 | ACTTTTTTTTTTTTTTTTAGCAGTTTGAGTTGGTGTAGTGTATTCTTGG |
| chr12 | 52899800 | 52899900 | tag_21160 | − | 41 | TATGAGGAGCTGCAGAGCCTGGCTGGGAAGCACGGGGATGACCTGCGGCGCACAAAGACTGAGATCTCTGAGATGAACCGGAACATCAGCCGGCTCCAGG |
| chr12 | 57846650 | 57846700 | tag_21447 | − | 42 | TGGACCCAAACTGAGGAGCCCGGAGCTGCCGCTGGGGGATCGGGGCCGGG |
| chr12 | 107761050 | 107761100 | tag_23158 | − | 43 | AGGGCCGGGCGGGACGGGAAACGTTAGGGCAGCGGCCCCCGGGGTGAGGG |
| chr12 | 113050900 | 113050950 | tag_23371 | + | 44 | CGTAGCCCCAGCTGAGGCAGGAGAATTGCTTGAGCCCAGGAACTGGAGGC |
| chr12 | 120198900 | 120198950 | tag_23669 | − | 45 | GCCAGCCCAGAACACTGGTCTCGGGCCCGAGAAGACCTCCTTTTTCCAGG |
| chr13 | 45418300 | 45418350 | tag_25246 | − | 46 | CTTGTTACAACTGAGTCCGGGTTGGAGGAGGTGTGGGGCCGCTGCCGCCA |
| chr13 | 69167900 | 69167950 | tag_26012 | − | 47 | CCCCCACAACCGCGCCTGGCTACTTTTTGTATTTTTAGTAGAGACAGGGT |
| chr13 | 72494150 | 72494200 | tag_26094 | − | 48 | AATGTCAAGTTAGAAAAAATGTTGTAGTTTCATGTTGTTGGTTTGCAAAT |
| chr13 | 96427200 | 96427250 | tag_26846 | + | 49 | TGGGTCTGAATTCCAGTCTATCACTTGTTATGTGACCTCGGATGAATCAC |
| chr13 | 101898250 | 101898300 | tag_27053 | − | 50 | TGAAATGCTTAGGACCAAAAGTGTTTCAGATTTCAGATTTTTAAAATATT |
| chr14 | 37590000 | 37590050 | tag_28303 | − | 51 | TAAGCCGTGGAAAATGTTCTTGATCATTTGCAGTTAAGGACTTTAAATAA |
| chr14 | 39432100 | 39432150 | tag_28366 | − | 52 | TTGTCAGTGCCGCAGCCCCGACCGCCGGGAGCTCGAACCCGAGCCGGGGC |
| chr14 | 42274950 | 42275000 | tag_28442 | − | 53 | TTGTGGGTAAGTTCTCTCTGAGATTTGGGAGATTCATAAATTTGTGTTTT |
| chr14 | 47937850 | 47937900 | tag_28594 | − | 54 | CACTCCTGACATCATCTGATAAAAGAAAGTCTTCAGCCGAATTTAATTTA |
| chr14 | 58244600 | 58244650 | tag_28961 | − | 55 | TGAGCCGCTTGGCGTCGTGGTATCTGAGAAGCTGCTCTATTCCTTTCCTT |
| chr14 | 63853000 | 63853050 | tag_29171 | + | 56 | CTCAGCTGCGCCCAGAGCCTTCGGCCGGACCTGAAAAAGCGAGAGGGAGA |
| chr14 | 67816550 | 67816600 | tag_29318 | − | 57 | TCTGTCACCTGACTCGGCTCAAACATGGCTGCGCTGAGAGCTCTATTGCT |
| chr14 | 69486050 | 69486100 | tag_29391 | + | 58 | GTTCTGAGATTCACTACTGGTATGGCCTGGAGAATGCAGACCCTGTCCAG |
| chr14 | 88649650 | 88649700 | tag_30094 | + | 59 | CCAAAACTATTCATTTGCATTGTAGTAGTTTGTACAGTCATATGTAAAAC |

TABLE 1-continued

| Chromosome Location | Start on Chromosome | End on Chromosome | OncRNA ID | Chromosome strand | SEQ ID NO | Nucleotide Sequence |
|---|---|---|---|---|---|---|
| chr14 | 90396800 | 90396850 | tag_30143 | - | 60 | GTCGGGGAAGCGTTCTAGGCTGGGCGCGCGGTCTCGGGTCAGGTGTGGCG |
| chr14 | 92486050 | 92486100 | tag_30219 | + | 61 | TATGTCCTGGTGAGGCTCCAGCAAGCAGTGAAGCCCCACCTGTCCATCCC |
| chr15 | 38351850 | 38351900 | tag_31664 | + | 62 | CATGTTTTGTTACAGGTTGTAGAGTATTTGCAGAAGGAAACCATTTCTGG |
| chr15 | 40873650 | 40873700 | tag_31796 | - | 63 | GGGACACAGCGGGACAGGTGAGAAGCTGGGCGCGGCCTCTACTGGTCTGC |
| chr15 | 62053800 | 62053850 | tag_32551 | - | 64 | TTTATCCCACTCCTGACAGTTTATCCCACTCTTGACACTTCCCCTTGAGC |
| chr15 | 69058600 | 69058650 | tag_32828 | - | 65 | ACACCAGGTCTCCTGGCCTTGCTGACTCCCAGTCCAGGGAGATGGAGGCT |
| chr15 | 90294050 | 90294100 | tag_33736 | + | 66 | ATATGGTGACCTCCTGGGAGCGGGGGACCACCAGGTTGCCTAAGGATGGG |
| chr16 | 2762350 | 2762600 | tag_34360 | + | 67 | CACCAGCCCGGAGGGGCAGGTCTCGGTCTAGAACACCTGCTAGGCGCAGATCTAGGACCCGATCACCAGTACGACGCAGGTCTCGTAGTAGATCACCAGCCAGGAGAAGTGGCAGGTCACGCTCTAGAACCCCAGCTAGACGTGGCCGCTCACGCTCCAGAACCCAGCCAGACGTGGCCGCTCACGCTCTAGAACCCCAGCTAGACGCAGTGGTCGCTCACGCTCCAGAACACCAGCCAGGAGAGGGAG |
| chr16 | 3305500 | 3305550 | tag_34437 | + | 68 | TGGCTCTGTACCTGGACAGGGCTGCGGTAGGCCAGCGGTGGGCTGGCGGT |
| chr16 | 15866000 | 15866050 | tag_34894 | - | 69 | CTGCAATATCTGATTACATTGATGAATTCCGTTGTATTGTATGTGTGAAT |
| chr16 | 16144500 | 16144550 | tag_34906 | + | 70 | ATTAGAATGAGTAGTAGTGTCTGGGTGCAGTGACTCATGCCCCATTGAAA |
| chr16 | 24205200 | 24205250 | tag_35164 | - | 71 | TGAGCCCAGGAACTGGAGGCTGCAGTGAGCTATGACTGTTCCACTTCACT |
| chr16 | 25107050 | 25107100 | tag_35202 | - | 72 | GTCGCAGCCACCGGTCACCTCAGCTGTGAACCATGTAGGAGCCGTCTGGG |
| chr16 | 30535100 | 30535150 | tag_35448 | + | 73 | CCTCGTGAACTCAGAAGTTAGTTTTCGTCTCTGGACCTTTTTATAATCGG |
| chr16 | 48178000 | 48178050 | tag_35696 | - | 74 | CCATCATGTTCTTTATTATTGTGATTGAGACCTTTCTGTGGGCCAGGCAT |
| chr16 | 53503150 | 53503200 | tag_35882 | - | 75 | TGTCGGGCCGCGGCGGCGCTTGGCAGCCAGGAGCTCTGCATTGAAGGCAC |
| chr16 | 67928900 | 67928950 | tag_36401 | + | 76 | TGCCAGGGGCACTGCCTTCTCACAGCTGGCCTTGCCCCGTCCACCCTGTG |
| chr16 | 68237500 | 68237550 | tag_36417 | - | 77 | GTGCTACTCGCTCGAACCCGCCGGGCGAAGGAAGCACTTCCCATGCTCTC |
| chr16 | 70780900 | 70780950 | tag_36529 | - | 78 | AGTGGACTCAGGCATCAAAGAAGTGGCCAACGTGTGCAACCAGAGCCTGA |
| chr16 | 78380500 | 78380550 | tag_36827 | + | 79 | ATTCAGCCGTATCAGTGAAGAGTGAAGCACTGCACTCTTTAAGGATAGGG |
| chr16 | 85659500 | 85659600 | tag_37112 | + | 80 | AGCACAAATATGGTGACCTCCTGGGAGCGGGGGACCACCAGGTTGCCTAAGGAGGGGTGAACCAGGGCAGGTCGGAAATGGAGCATGTCAAAACTCCCGC |
| chr17 | 17591900 | 17591950 | tag_38147 | + | 81 | CCTTGGATCCGGCCTCCCGCCCAGTGCCTTTGGTCGCCGGCTGCCGCACC |

TABLE 1-continued

| Chromosome Location | Start on Chromosome | End on Chromosome | OncRNA ID | Chromosome strand | SEQ ID NO | Nucleotide Sequence |
|---|---|---|---|---|---|---|
| chr17 | 31534850 | 31534900 | tag_38643 | + | 82 | CCCTGAGCTGCCCTTGCGTTCAGTTGGAA GCCACGCAAAATGAACTGAAC |
| chr17 | 36486650 | 36486700 | tag_38844 | + | 83 | GCGTGAGAGGCGCGCGGCGGCGCAGTGAA CAGTCTCCTTCCACAAAACCA |
| chr17 | 38604550 | 38604600 | tag_38922 | − | 84 | GCAGCCCTGGCAGTGCCTCCGGCGCTTTG CCCTGGCCTGGTGGGAGAGGA |
| chr17 | 39723550 | 39723600 | tag_39047 | + | 85 | TGACACCTAGCGGAGCGATGCCCAACCAG GCGCAGATGCGGATCCTGAAA |
| chr17 | 39737900 | 39738000 | tag_39057 | + | 86 | TCCCCTGGACCCGCCCCCATCTGCCCAAG ATAATTTTAGTTTCCTTGGGCCTGGAATC TGGACACACAGGGCTCCCCCCCGCCTCTG ACTTCTCTGTCCG |
| chr17 | 39744000 | 39744050 | tag_39062 | + | 87 | ACATCCTGGTGGTAGAGGGGAAGGGAGGA GGTCAGACCTGTCACTCTCCT |
| chr17 | 40054350 | 40054400 | tag_39075 | − | 88 | CCAAAATGGCGATGCCTACCACCTAGAAC TGGATTGTGCGGTAGGCTTAA |
| chr17 | 49995200 | 49995250 | tag_39625 | − | 89 | TAACCGGCTGGCCGGGCGGAGCTGGCAGC ATTTGATTGTGGCTTGGGACG |
| chr17 | 50187300 | 50187350 | tag_39646 | − | 90 | GAATCCTGAACAAACAATCTGATCTAGCT TTGGCCTCTCTGCTCCCCAAT |
| chr17 | 50867150 | 50867200 | tag_39714 | − | 91 | CGCCACACTCTGGGCACGGCGTGGGCTGG GACATTTGGAATAAACGGATC |
| chr17 | 58083400 | 58083450 | tag_39984 | + | 92 | CGCGCGTCGGCCGCGCTCAGCGGCAGAGC GGAGCGCAGCTGTGAGGCGCC |
| chr17 | 63827000 | 63827050 | tag_40255 | − | 93 | TAGTGTGCGGAGAGGGGCGCGGGGTGGAA TTGCTGCGGGAAGTGGGAAAC |
| chr17 | 64919400 | 64919450 | tag_40314 | − | 94 | GCGGCTGAAGGCGATCCGCAGTGAGGCCC CAGCCATTCGGATTGAGCCTT |
| chr17 | 67717950 | 67718000 | tag_40442 | + | 95 | GCAGCGCTGGAGGAAGAATTCACGTTGTC TTCGGTAGTCCTGAGCGCCGG |
| chr17 | 68248100 | 68248150 | tag_40474 | + | 96 | GGCCTGTCGGGTCAGGGCGGTTCGCGGGT GCTGTCAGAGCTGGGCCGGGG |
| chr17 | 75261900 | 75261950 | tag_40741 | + | 97 | ATGGCTGCCCCCGCAGTGAAGGTTGCCCG AGGATGGTCGGGCCTGGCGTT |
| chr17 | 79782300 | 79782350 | tag_40981 | + | 98 | GGGCAGAGGCAGTGTGGGCTGATGATGTG CTTTTGGCCTTCTCGGGACTGT |
| chr17 | 81133250 | 81133300 | tag_41079 | − | 99 | CTGGCCTGGCAGGTGACGGTGCTGGATGT GGCCTTTTTGCCTTTTCTAAA |
| chr18 | 750700 | 750750 | tag_41311 | − | 100 | TTTCCTTAACATTCTTCCTCCCCTGCCTG GCCCAGTCCTTATCCCCTGCT |
| chr18 | 797950 | 798150 | tag_41315 | − | 101 | AAGAAAATAGACAATACACTTATCTGGCT GGGGAGATACCATGATCATGAAGGTGGTT CTCAGAGTGAGGCTCATCCATTGCACTTT GGTTGTGCTGACCCCTGTGATTTCCCCAA ATGCAGAATTTGTAGTAGTGAGGGACTGT GTTCGTGCTTTCCCCTGTCATTTTTTGTC CTAAGAGATCATAGTGTGAAGTTTAT |
| chr18 | 14830150 | 14830250 | tag_41793 | + | 102 | ACTGCCATGAAGCTCTGCAGAAGAAAGAT CTGGAAGTGGGAGACACTTTCACTATATA TAGTGGCTCCCACTTCCAGATCTTTCTCT CTGTATATATAGT |
| chr18 | 51356800 | 51356850 | tag_42903 | − | 102 | CATTGGTGATTAAGGCTTCAACATACAAA TTTCGGGGGGGACAAAAACAT |

TABLE 1-continued

| Chromosome Location | Start on Chromosome | End on Chromosome | OncRNA ID | Chromosome strand | SEQ ID NO | Nucleotide Sequence |
|---|---|---|---|---|---|---|
| chr19 | 29942250 | 29942300 | tag_45203 | + | 104 | GCGGCCGCCACGCGACGCCTGGCTGGGCC CGCACCGGAGAGGCGTCTCGG |
| chr19 | 46346900 | 46346950 | tag_45995 | − | 105 | CCCTTTCGCCACAGAGCGCGCGGAGGACA AGGTGACCAGAGGTTCCCCAG |
| chr19 | 52962800 | 52962850 | tag_46333 | − | 106 | AGTTGCACGGCGGCGTGTGCGTTTCCTAG TTGTCTGGTGCTGCTATATAG |
| chr19 | 53671950 | 53672000 | tag_46359 | + | 107 | TCAGACATGACATTCAGACTGAGGTCCTC AAAACTGAGGGGCATTTTCTG |
| chr19 | 57819550 | 57819600 | tag_46611 | − | 108 | AGGCTGTAAAGAGGGCGCTACCCAGAGGT GCATCTGCAGGAAAAGCCCAC |
| chr2 | 9615450 | 9615500 | tag_47042 | + | 109 | ATATAGGAAAGAACCACAGGTAGTTTCAT GTGGTTGGAGGACAGAGGGAA |
| chr2 | 10302900 | 10302950 | tag_47066 | + | 110 | GGCAGGCGGGCCGCGGCGGCGGCGGGCAG CGGACGGGCGGACTGACGGGC |
| chr2 | 69518000 | 69518050 | tag_49256 | + | 111 | AGTCCTAGCTACTTGAGAGACTCAGCTGG GATGATCACTTGAGCCCAGGA |
| chr2 | 85539000 | 85539050 | tag_49878 | − | 112 | AGGGCAGCTCGCCCCGCGGAGTCCGGGCT GAACCACACTGCGCGGCCGCG |
| chr2 | 152284400 | 152284450 | tag_52186 | − | 113 | AGGTAGTGAGTTATCTCAATTGATTGTTC GCTTTCAGTTACAGATTAAGC |
| chr2 | 173395050 | 173395100 | tag_52889 | − | 114 | TGCTGTTCTCCAACCAGTGCTTATGCTGC AGGCAATTTTGTTGTTCAGAA |
| chr2 | 174594100 | 174594150 | tag_52936 | − | 115 | CTAATCAGACGTTGCTGAAGTATTGTTTT TCAATGATGATTGACTGAGAA |
| chr2 | 218341950 | 218342000 | tag_54843 | + | 116 | CCTTCTGTCCCCTGCTCCCTTGTTCCCCA GTCCCTGTGTCATCAAGATG |
| chr2 | 239069350 | 239069500 | tag_55663 | − | 117 | CTCACCAAGCAAGTGTCGTGGGGCTTGCT GGCTTGCACCGTGACTCACTCTCACTAAG CAAGTGTCGTGGGGCTTGCTGGCTTGCAC CGTGACTCACTCTCACTAAGCAAGTGTCG TGGGGCTTGCTGGCTTGCACCGTGACTCC CTCTC |
| chr20 | 9068700 | 9068750 | tag_56150 | + | 118 | CGAGGCGACAGCTCGGGCTCTGGAGCCGG GAGGCGAGAACGAGGAGGGAG |
| chr20 | 25390750 | 25390800 | tag_56729 | − | 119 | TTCCGGGCTCCGGGCTCTGGGTGGCGGCG GCTGTGAGCGGCGGCACTGCG |
| chr20 | 35765850 | 35765900 | tag_57047 | + | 120 | GAGTCTGAGATCAGTCTGGGCCACATAGC GAGACCCCGTCTCTATGTTAA |
| chr20 | 36870700 | 36870750 | tag_57094 | + | 121 | GTTCAAGACCAGCCTTGGCAATATAGCGA GACCCCGTCTCTACAAAAACA |
| chr20 | 50750550 | 50750600 | tag_57742 | + | 122 | AAAAGCATATATACCTCTGACCAGTGACG TGCAATAGGCATGACACGAGT |
| chr20 | 50752950 | 50753000 | tag_57747 | + | 123 | TTACAAATTTGACTCTTGAATGGCAAAAT AATGTTAGTATGTAGAAGGTT |
| chr20 | 53738650 | 53738800 | tag_57859 | + | 124 | ACGACTCCTGGTTTGCCACAAGCCCGGCC TCTGTAGTGAGAGAGCTGTGACTGCGTTT CCAGCTCCTTGAAGGCAGAGAGACTCCTG CCTTTCGGGGCGGGCGGGCTGGAACAAAG ACACCAACGGGGCCACCTCGGAAAGTCTT TTTGA |
| chr20 | 54208100 | 54208150 | tag_57876 | + | 125 | ATGGCGGCCACCATGAAGAAGGCGGTGAG TGGGGAGCTCGGGCTCTGGA |

TABLE 1-continued

| Chromosome Location | Start on Chromosome | End on Chromosome | OncRNA ID | Chromosome strand | SEQ ID NO | Nucleotide Sequence |
|---|---|---|---|---|---|---|
| chr20 | 58448250 | 58448350 | tag_58054 | + | 126 | AACACCAAGAGCAGCTCTGAGATCATGCTGGCCCTACGCGAATTGAGTTTCTGTGGCCTAATTGGATTTGGAGAACGCCTTCCCTGGCCCCTTTTCCTCA |
| chr20 | 62861750 | 62861800 | tag_58278 | - | 127 | AACGGCGCGCCGGCTGTGGCCGGCGCAGAGTAGTGCTCGGGCCGGGGGTC |
| chr22 | 27922350 | 27922400 | tag_60225 | - | 128 | TGAGATTGGTAGACATATGACACTGGTAGAATTAGTTTGAACATCTGTGT |
| chr22 | 33704900 | 33704950 | tag_60463 | - | 129 | TGTGGGTCCTCTGCTCTGGCAACAGGCAGAGCACTGCTTTAGAGCCTCTG |
| chr22 | 36775050 | 36776100 | tag_60618 | - | 130 | TTGGAGAGTGCATCCGGCCCGGTACTTGTGATCGGAGGAGAGCCGGATCG |
| chr22 | 50508250 | 50508300 | tag_61228 | + | 131 | TGGCGCCAGAACTAGTGGCGGGCTGAGGACGCCGTACCCCTCGGAAGGCA |
| chr3 | 47266450 | 47266500 | tag_62984 | + | 132 | CTTGCAACATAGCGAGACCCCGTCTCTACAAAAAAATTTAAAAATTAGC |
| chr3 | 48159000 | 48159050 | tag_63026 | - | 133 | CCACGAGGACTTTAAAGAAGACCTGAAGAAGTTCCGCACCAAGAGCCGGA |
| chr3 | 113263200 | 113263250 | tag_65168 | + | 134 | AGGCTGCTAAGTCATCCTGGCAGCATTGCCACATGAGCCCCATGCGGTGC |
| chr3 | 149752400 | 149752450 | tag_66565 | - | 135 | GTGAAGATGCTGCTGGAATTGTCCGAGGAGCATAAGGAACACCTGGCCTTT |
| chr3 | 169764600 | 169764650 | tag_67280 | - | 136 | TGAGCTGTGGGACGTGCACCCAGGACTCGGCTCACACATGCAGTTCGCTT |
| chr3 | 184298900 | 184298950 | tag_67762 | - | 137 | CACTGCTGTAGATGGGCGGTCTGCGAGCGGAGTTACCGAGTTTTACTCCG |
| chr3 | 194159250 | 194159300 | tag_68175 | + | 138 | CCCTGGATGCCTGCCCCTTGAATGGGGGTCAGGCTGTGCATACATTGTGA |
| chr3 | 195658050 | 195658100 | tag_68250 | + | 139 | CAGTCTGCGCAGGGACTGGCGGGACTGCGCGGCGGCGACTACAGACGTGT |
| chr4 | 7112150 | 7112400 | tag_68635 | - | 140 | GGGATGTGAGGGCGATCTGGCTGCGACATCTGTCACGCCATTGATTGCCAGGGTTGATTCGGTTGATCTTGCTGGCTAGACGGGTGTCCCCTTCCTCCCTCACTGCTCCACATGCGTCCCTCCCAAAGCTGCATGCTCCATTGACCATCCCCAACAGAGGAGGACCGGTCTTCGGTCAAGGGTATATGAGTAGCTGCACTCCCCTGCTAGAACCTCCAAACAAGCTCTCAAGGTCCAAATGACACTGGGG |
| chr4 | 28712100 | 28712150 | tag_69423 | + | 141 | GCTTAAAGGAAAGCAAAAGCTGTGTTGAGAGAATAAAACAGGGATAAGTC |
| chr4 | 81382050 | 81382100 | tag_71049 | + | 142 | AAAATGCCTATTTAAATTACTATTTCATTATTTTTCTCAAAAGTGTGAAA |
| chr4 | 87505600 | 87505650 | tag_71261 | - | 143 | CCCAGGAACTGGAGGCTGCAGTGAGCTATGATTGCAATTACACTCCAGCC |
| chr4 | 140152300 | 140152350 | tag_72898 | + | 144 | TGGGGAGAGGAGGCGAGAGGCTCTCCTTCCCCGCTTCCCCCCTAGGGGTT |
| chr4 | 145186850 | 145186900 | tag_73067 | + | 145 | GACTGCAGTCCTGAGACCCTATAACCTGTATGACTAGAGAAGTGAAACTA |
| chr4 | 151442350 | 151442400 | tag_73273 | + | 146 | GAAAACCCCCCAAACCTTAAAAATGTAGAATCTCTCAGCTAATCTATAT |
| chr4 | 165112750 | 165112800 | tag_73762 | - | 147 | CAGGGCTTCGGCCTCCGGCGTCGGGAAATGGCGGCGGGGGGCAGGATGGA |

TABLE 1-continued

| Chromosome Location | Start on Chromosome | End on Chromosome | OncRNA ID | Chromosome strand | SEQ ID NO | Nucleotide Sequence |
|---|---|---|---|---|---|---|
| chr4 | 173268150 | 173268200 | tag_74031 | + | 148 | AAAAATGTTAGGGTGGTGCAAAAGTGATCGTGGTTTTTGCAATTTTTTAA |
| chr5 | 14001200 | 14001250 | tag_75126 | - | 149 | TATTGTGTGATACTGAGGCTTGGAGTGTGAATGAATCCTTCACCCAGGTA |
| chr5 | 173888350 | 173888400 | tag_80583 | + | 150 | TCGGCTCGGTCCTGAGGAGAAGGACTCAGCCGCGGCTGCGGGACCCGGGC |
| chr5 | 174724600 | 174724650 | tag_80619 | + | 151 | CGCCGCTGCCGGGTTGCCAGCGGAGTCGCGCGTCGGGAGCTACGTAGGGC |
| chr6 | 16453150 | 16453200 | tag_81642 | - | 153 | CCCCTCTATCAATGATGAGACTGATGCTGAGAAAAGTAACATGATTATGT |
| chr6 | 24705400 | 24705450 | tag_81899 | - | 153 | TACACATTAAAGCAGATCTGGAGTCTGAAGTAGCTATAAAGCAGCTATAA |
| chr6 | 38229900 | 38229950 | tag_82871 | + | 154 | AGAAGCATGCCTTTCAGGGCATTGATAAAAAGAGTGAAATGTTCAGGACC |
| chr6 | 52264600 | 52264650 | tag_83427 | - | 155 | CTGAGCAAGATGCAGGATGACAATCAGGTCATGGTGTCTGAGGGCATCAT |
| chr6 | 127266850 | 127266900 | tag_85800 | + | 156 | GCGCGTTCCCGGCAGCTGCGGGCTCCGAGGCCAGAGAGAAAAGACTGCGA |
| chr6 | 166956500 | 166956550 | tag_87323 | - | 157 | GAGCAACGCGACTGACCGTGGTCGTGGGCGGACGGCGGCTGCAGCGTGGA |
| chr7 | 6059100 | 6059200 | tag_87724 | - | 158 | CTGGTTTTCCGTCTGGTGAGGGGTTACTTCCGGGTCGGACGGCGCTAGCTGCAGCATCGGAGTGTGGCAGTGCTGGGCTGGCCGGCGGGCTGGGCTGGGG |
| chr7 | 6448050 | 6448100 | tag_87734 | + | 159 | CTGCGCAGAAACGCTGATCCGGAAGGCGCTGGCTGAGTCGATTGCAGGTC |
| chr7 | 45111800 | 45111850 | tag_89181 | + | 160 | CTTTCGGCGGGTGACATCTTTGCTGAGGGCTCAAGCGGAGCGATAGGTCA |
| chr7 | 56289400 | 56289450 | tag_89671 | + | 162 | CTTCGAAAATGAGGGTGAAGATGAAGCCATGTTTGTAGAATATAGAAAAC |
| chr7 | 95434950 | 95435000 | tag_90904 | - | 162 | GGAGCTGCTGGCCAGGCCGGAGCGAGGCAGCGCGCCCGGCTCCCGCGCCA |
| chr7 | 128839300 | 128839350 | tag_92163 | + | 163 | TGGCAGGTCTAGTGTCTTTGCCACTTGCCTGGTGATTTCTATGATGAAAT |
| chr7 | 157410800 | 157410950 | tag_93308 | + | 164 | GGTTACTTCTGTGGACTTGGGCCGAACAGCACTGTCTAAGCAGGACATGAAAAGAAGGGGGAAGCGTCTCTCCTTTTCCCTTCATGGAACTTTCCATTGAAAAATTAGCCCCTTCCAGTCCTTCTCGGATGAAGCACAGTTGCCGGTTAC |
| chr8 | 9780950 | 9781000 | tag_93694 | + | 165 | CAGCAACTGTGATACCTTGTAGAATATGAGTGATATGCAAGCTGTGTTTT |
| chr8 | 48198250 | 48198300 | tag_95072 | - | 166 | AACCCCAGGCCAGGGAGGCCCGGGTTTGGGATGCCTTCCTCGGGAGTGTG |
| chr8 | 60281350 | 60281400 | tag_95457 | - | 167 | AGGCCACAGCCGCTCCCTCGCTCTGCTGGGGCCTCCGGACGCGCTTCCCA |
| chr8 | 99893500 | 99893650 | tag_96875 | - | 168 | GTTGGTGTTGAGGTGAGTCCGGTCCCTTTTGCATCCCTACCCCGACACTGCGGGTTGTCACAACGGCACCCTCCCGCTTTCTCTCTGCCTCGGATTTAGTCGTGACTGTGTGTCTCCGCCGTGGTGCAGCTTCAGGCCTCTCCCGCATCT |
| chr8 | 100397100 | 100397150 | tag_96893 | + | 169 | TGAAGTGAGGTAGGAGGTTGATCAAATTTTCTGTATAACAGGAATATGGA |

TABLE 1-continued

| Chromosome Location | Start on Chromosome | End on Chromosome | OncRNA ID | Chromosome strand | SEQ ID NO | Nucleotide Sequence |
|---|---|---|---|---|---|---|
| chr8 | 112519350 | 112519400 | tag_97345 | + | 170 | TGAATAATAGGCTTATATGTTATAACATCAAAATATAATTCGAGTTTGAC |
| chr8 | 118111800 | 118111850 | tag_97581 | - | 171 | TAAGTGTAACATTCAGAACCGGGTAACATTCGGCGACCGAACGCGGCGGT |
| chr8 | 119325150 | 119325200 | tag_97636 | + | 172 | CACAAAGTAGGGAATATTCAAGATTGTATTAGGTTGGTGCAAAAGTGATT |
| chr8 | 122782950 | 122783000 | tag_97758 | - | 173 | CTGCTGGTTTCCAACTTTCCGCTCATCTTCGTCTCCGCAGCCTCCTGCAA |
| chr8 | 129984200 | 129984250 | tag_98078 | + | 174 | GCAGGGACAACAGTCAGAGGGCTGCAGGGGCCTGAAGCCAGACACGGGAC |
| chr8 | 133571800 | 133571850 | tag_98219 | - | 175 | GACCGGAGGGAGGAGGAGGAGGAAGAAGAGCGGAGAGAGAAGGAAGAGGC |
| chr8 | 135645650 | 135645700 | tag_98308 | - | 176 | GACTTTGGACATGAAGTCCCCAGCATCTCTACCAGCTCCACTGAATTAAG |
| chr8 | 143858250 | 143858350 | tag_98645 | - | 177 | GCTGTCGGCCGAGCGCGCCGTCACCGGCTACACCGACCCCTACACCGGGCAGCAGATCTCCCTCTTCCAGGCCATGCAGAAGGACCTCATCGTCCGGGAG |
| chr8 | 143859850 | 143859950 | tag_98647 | - | 178 | TGCTGTCGGCCGAGCGCGCCGTCACCGGCTACACCGACCCCTACACCGGGCAGCAGATCTCCCTCTTCCAGGCCATGCAGAAGGACCTCATCGTCCGGGA |
| chr8 | 143861450 | 143861550 | tag_98649 | - | 179 | CTGTCGGCCGAGCGCGCCGTCACCGGCTACACCGACCCCTACACCGGGCAGCAGATCTCCCTCTTCCAGGCCATGCAGAAGGACCTCATCGTCCGGGAGC |
| chr8 | 143863050 | 143863150 | tag_98651 | - | 180 | GTCGGCCGAGCGCGCCGTCACCGGCTACACCGACCCCTACACCGGGCAGCAGATCTCCCTCTTCCAGGCCATGCAGAAGGACCTCATCGTCCGGGAGCAC |
| chr8 | 143864600 | 143864750 | tag_98653 | - | 181 | AGCTGCTGTCGGCCGAGCGCGCCGTCACCGGCTACACCGACCCCTACACCGGGCAGCAGATCTCCCTCTTCCAGGCCATGCAGAAGGACCTCATCGTCCGGGAGCACGGCATCCGCCTGCTGGAGGCCCAGATCGCCACGGGCGGCGTCA |
| chr8 | 143866250 | 143866350 | tag_98656 | - | 182 | TCGGCCGAGCGCGCCGTCACCGGCTACACCGACCCCTACACCGGGCAGCAGATCTCCCTCTTCCAGGCCATGCAGAAGGACCTCATCGTCCGGGAGCACG |
| chr8 | 143868300 | 143868400 | tag_98658 | - | 183 | GGAGAACCGGAAGCTGACCGTGGAGGAGGCGTTCAAAGCAGGAATGTTCGGGAAAGAAACCTACGTGAAGCTGCTGTCGGCCGAGCGCGCCGTCACCGGC |
| chr8 | 143878400 | 143878450 | tag_98664 | - | 184 | GGCGAGCGGGCAGGTGCGGCGGGTGCGGCGGGTGCGGCGGGTGCGGCGGG |
| chr8 | 144789800 | 144789900 | tag_98753 | - | 185 | CAGAGATGCCCCTGCTGGCCGCAAAGTGGGTCTCATTGCTGCCCGCCGGACTGGACGTCTCCGGGGAACCAAGACTGTGCAGGAGAAAGAGAACTAGTGC |
| chr9 | 25677700 | 25677750 | tag_99624 | + | 186 | GGGCTCCGAGTCCCGGGAGCGGAGGCCGGAGTCGGGTTCCTGTAGAGGCT |
| chr9 | 90099550 | 90099600 | tag_101017 | - | 187 | AGACAAGCTCGGTCTGAGGTTGTTTTCCTTTGAACTGGCTCTCTCACATT |
| chr9 | 107363050 | 107363100 | tag_101649 | + | 188 | GAGATTGAGACCAGCCTGGGCTAACATAGCGAGACCCCGTCTCTACAAAA |

TABLE 1-continued

| Chromosome Location | Start on Chromosome | End on Chromosome | OncRNA ID | Chromosome strand | SEQ ID NO | Nucleotide Sequence |
|---|---|---|---|---|---|---|
| chr9 | 110800700 | 110800750 | tag_101776 | - | 189 | ACCACGCCATAGGCCCACACATCAGACTCTGTAGTGTAGCGGTTATAAAA |
| chr9 | 114168900 | 114168950 | tag_101915 | + | 190 | CCTCTAAAAAACCCATTCCCACACTAGCTCGGACTGAGGCCAAGATAACC |
| chr9 | 123110200 | 123110250 | tag_102264 | - | 191 | TGTAGTGGTCCTGCAGGAGTGGAGCCTGTAGGACTTGCTTCTCAGCGGCT |
| chr9 | 123111550 | 123111600 | tag_102265 | - | 192 | TGTCAGGCAGTGGAGTTACTTACAGACAAGAGCCTTGCTCAGGCCAGCCC |
| chrX | 2792950 | 2793000 | tag_103388 | - | 193 | TGGAGGCTGCAGTTAGCTATGATCACACCACTGCATTCCAGCCTGAGTGA |
| chrX | 10061250 | 10061300 | tag_103625 | + | 194 | CTAATTGATCACAACCAATTACAGATTTCTTTGTTTCTTCTCCTCTCCCA |
| chrX | 16719400 | 16719450 | tag_103865 | - | 195 | CTTTTCCTCATTCGCCAGCTTTGTAGGTGACTGACCTAGTAGGCATGTGG |
| chrX | 47829700 | 47829750 | tag_104884 | + | 196 | CTGGGCAACATAGCGAGACCCCGTCTCTCTCTAGTGTGTGTGTGTGTGTG |
| chrX | 74844500 | 74844550 | tag_105594 | - | 197 | CAGGGGAGTTGAGGAGGTTTACTGCAAACAACTGTTCTTTTTTCTTTTGG |
| chrX | 144927750 | 144927800 | tag_107740 | + | 198 | GATTCTAGAATCACAAATAAAGCCAATTAAAATCTTTAAATTTGTTGTAC |
| chrX | 145820500 | 145820550 | tag_107766 | + | 199 | TGGCACATCTAGCAACAGAGCCAGATCAGAACCCAGGTAAGCTCGGTCTC |
| chrX | 152393300 | 152393500 | tag_107993 | - | 200 | ACCATGGTTGTCTGAGCATGCAGCATGCTTGTCTGCTCATACCCCATGGTTTCTGAGCAGGAACCTTCATTGTCTACTGCTTTACAGGGAAATAGTGTTTTATGCATCGTGTATATGAGTTTAGTATTTACTCATATTCTATGACTCTCTACTCTTAGATCACTTCTGCCTTTTTCTGCACATTGTTTATCTGTTCCAAA |
| chrX | 155066050 | 155066100 | tag_108138 | - | 201 | AACCCAAAAAGTCACACCTGTGTCCTGTGCGCGGGTGCTGCAGGCTTAGG |

Figure 1C:
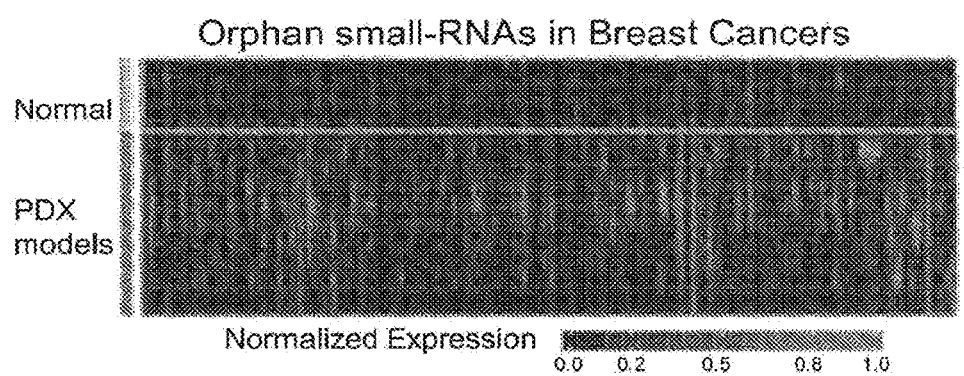
Figure 2B:
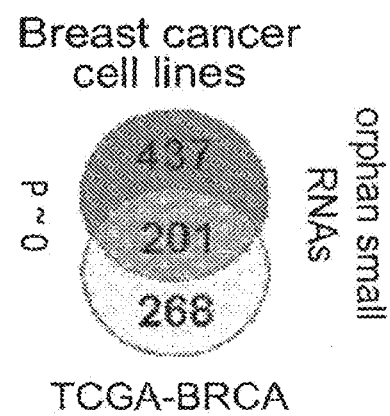

As a third line of evidence a dataset of small RNA profiles from 10 patient-derived xenograft (PDX) models and four normal epithelial samples (unmatched) was analyzed. As shown in FIG. 1C, these oncRNAs are largely absent in normal samples; yet can be frequently detected in PDX models. By summing the expression of all 201 oncRNAs across every sample, a simple classification rule can be derived that perfectly groups the normal and PDX profiles (FIG. 2B). Together, these findings establish the existence of a large pool of oncRNAs whose expression is strongly associated with breast cancer.

Figure 3A:
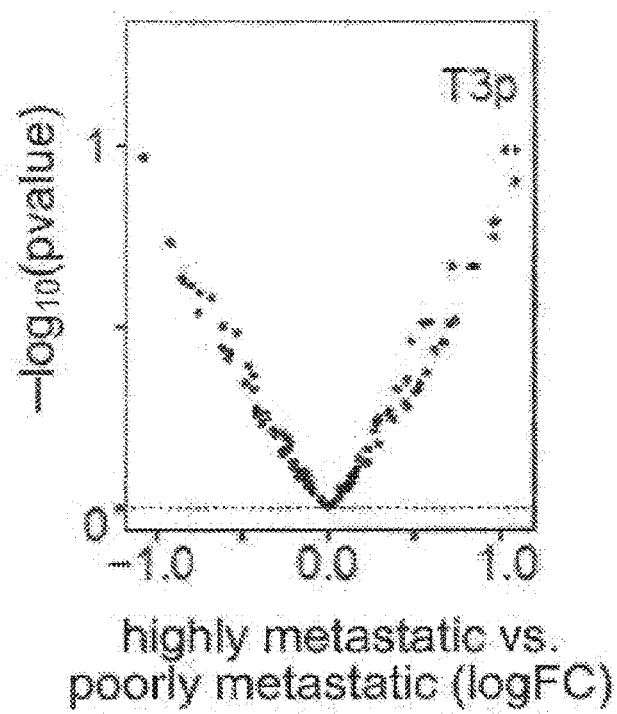
FIG. 3A-FIG. 3F show that the oncRNA T3p is strongly associated with breast cancer progression.
Figure 3B:
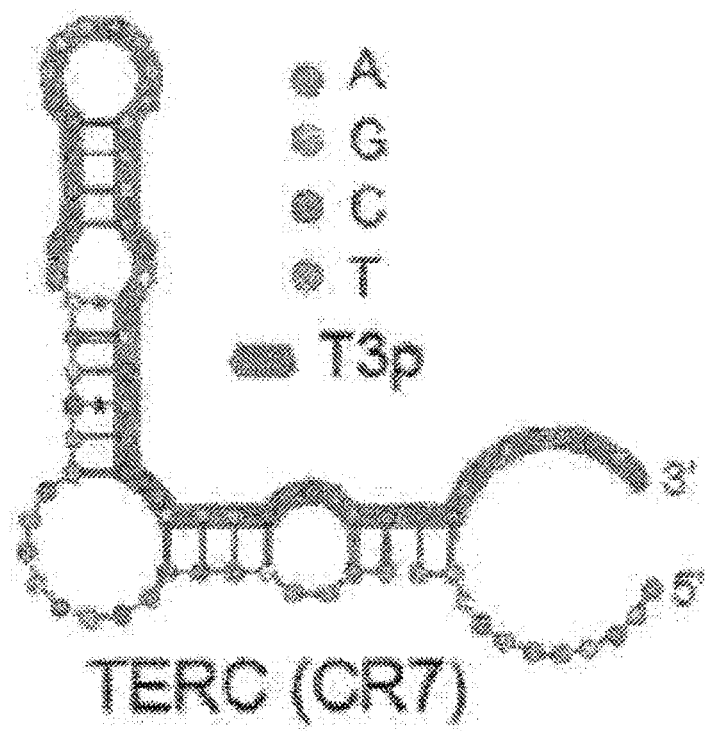
Figure 3C:
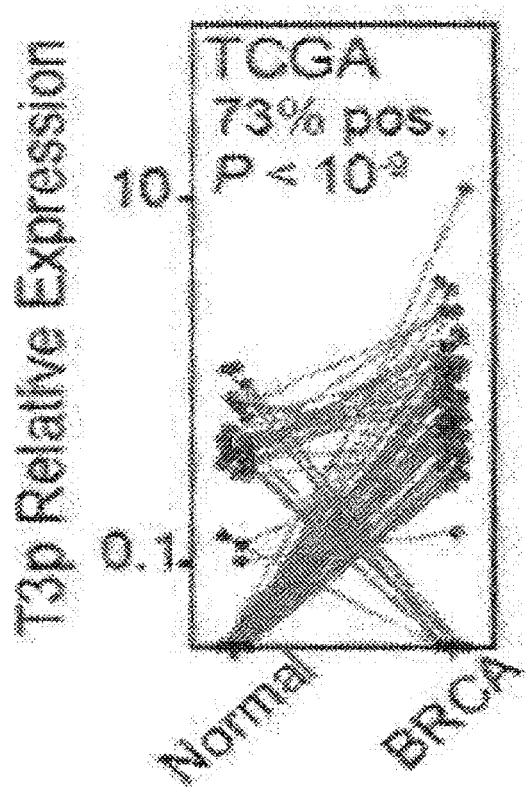

Example 3. Identification of T3p, an oncRNA Associated with Breast Cancer Progression In addition to the cell lines mentioned above, highly metastatic cell lines were also profiled that had been in vivo selected in immunocompromised mice for higher metastatic capacity (1, 15). Comparing the expression of oncRNAs in these highly metastatic cells relative to their poorly metastatic parental lines, one oncRNA was noted that had significantly increased levels in highly metastatic cells (FIG. 3A). This 40-nucleotide oncRNA is generated from the 3' end of the TERC gene, which codes for the RNA component of telomerase (FIG. 3B). As such, this previously unknown small RNA was named T3p for TERC 3' RNA. Analysis of a previously published dataset from the same cell lines (7) further corroborated the higher expression of T3p in highly metastatic cells (FIG. 3C). This upregulation of T3p expression in metastatic cells was validated by qPCR (FIG. 3C).

Figure 3D:
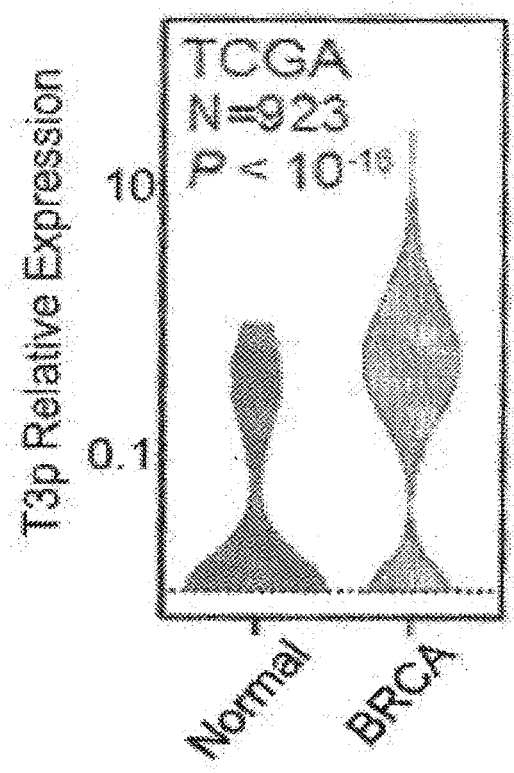
Figure 3E:
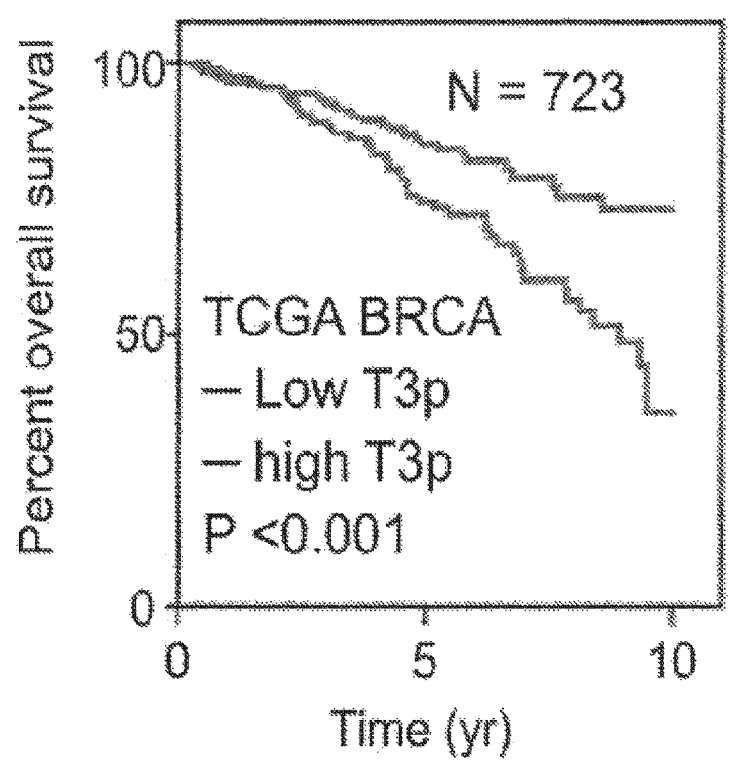
Figure 3F:
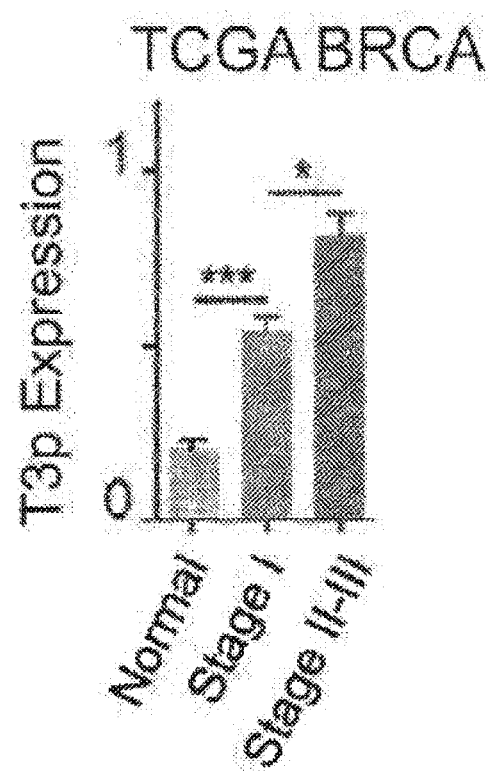
Figure 4B:
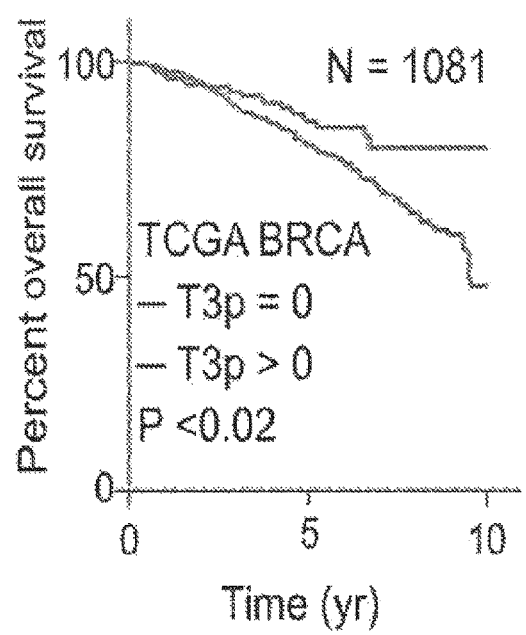
Figure 4C:
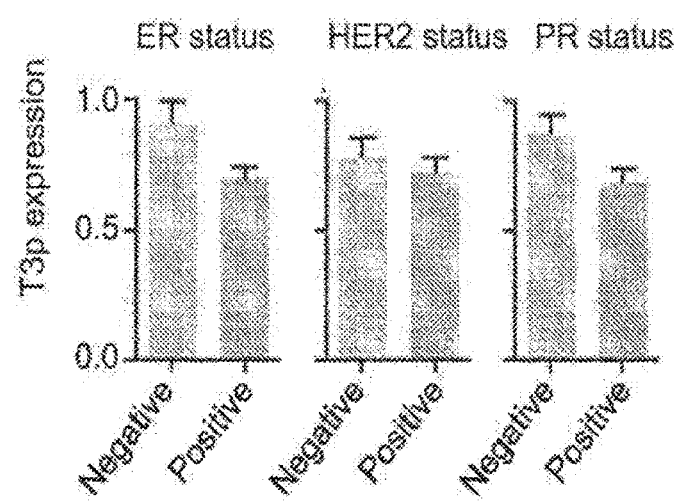
Figure 4D:
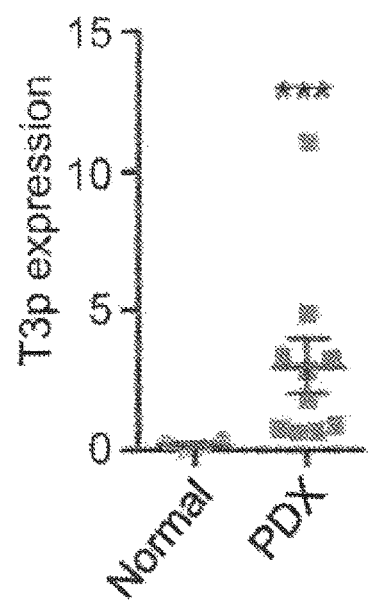

Next, whether the increased expression of T3p contributed to the pathogenesis of the underlying disease was investigated. Approximately 400 matched normal and breast cancer tumor tissue samples from TCGA-BRCA (The Cancer Genome Atlas, Breast Cancer) were analyzed, and it was noted that expression of T3p was highly cancer-specific (FIG. 3D). Then, the entire TCGA-BRCA dataset with roughly 1000 tumor samples was included. As shown in FIG. 3E, consistent with its identity as an oncRNA, T3p was not detected in the majority of normal samples, yet was detected at relatively high levels in tumor biopsies. More importantly, consistent with the higher expression of T3p in highly metastatic cell lines, a highly significant association between patient survival and T3p expression was observed (FIG. 3F). Further, as shown in FIG. 3G, expression of T3p increases across normal, stage I, and stage II or III samples in the TCGA-BRCA dataset. Detection of any level of T3p in tumor samples was strongly associated with both breast cancer and shorter overall survival (FIG. 4A and FIG. 4B). Higher expression of T3p in clinical breast cancer samples was also strongly correlated with advanced stage breast cancer (FIG. 3E). Interestingly, stratification of these cancer samples by hormone receptor and HER2 status showed no strong association of T3p levels with estrogen receptor, progesterone receptor, or HER2 receptor expression (FIG. 4C). Consistent with this finding, increased expression of T3p in PDX models of breast cancer relative to normal epithelial tissue was also noted (FIG. 4D). Together, these results establish the oncRNA T3p as a cancer-specific biomarker with robust prognostic value.

Figure 5:
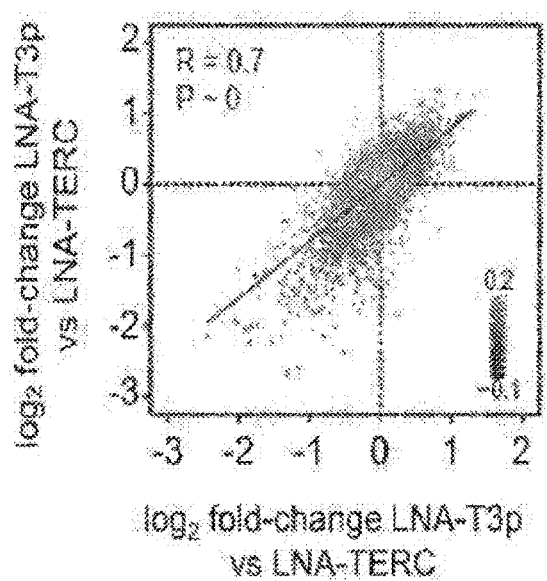
FIG. 5 shows T3p promotes metastatic progression. Gene expression changes induced by an anti-T3p LNA is largely comparable regardless which control is used: (i) an scrambled LNA, or (ii) an anti-TERC (but not T3p) LNA. Included is the Pearson correlation coefficient and the associated p-value.
Figure 6A:
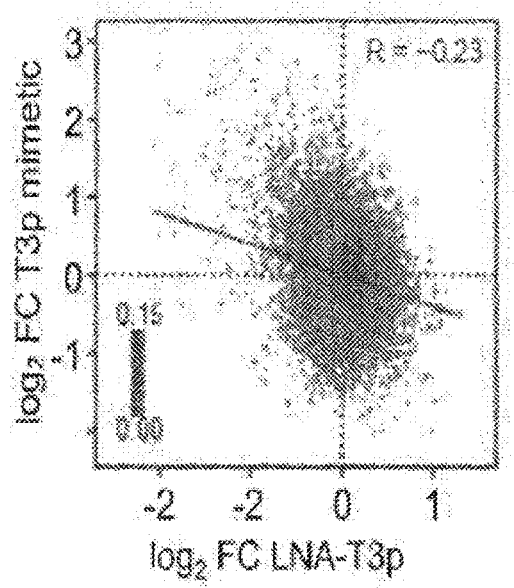
FIG. 6A-FIG. 6C shows T3p as a gene expression regulator and a driver of metastatic progression.

Example 4. T3p Acts as a Broad Regulator of Gene Expression in Breast Cancer Cells The strong associations between T3p expression and breast cancer progression from multiple independent datasets raise the possibility that T3p plays a direct and functional role in breast cancer progression. To elucidate its molecular function, it was investigated if modulating T3p expression levels resulted in regulatory consequences. To this end, T3p was silenced by transfecting highly metastatic MDA-LM2 cells with antisense locked nucleic acids (LNA) targeting T3p, or with control scrambled LNAs. Gene expression profiling was then performed to measure the genome wide regulatory impact of T3p silencing. Surprisingly, a highly significant change in the gene expression landscape of the cell upon T3p silencing, affecting thousands of genes, was observed. This is on par with the impact of many well-established post-transcriptional regulators such as small non-coding RNAs (7, 16). However, the full length TERC transcript remains a potential confounding factor, as the T3p-targeting LNA also impacts TERC function, which in turn could be responsible for the observed gene expression changes. To distinguish between these two possibilities, two independent approaches were used. First, in addition to the scrambled LNA, an anti-sense LNA against full length TERC, 5' of T3p was also used. As shown in FIG. 5, gene expression changes induced by the anti-T3p LNA are similar regardless of whether the scrambled or anti-full length TERC LNA is used as the reference. This observation indicates that inhibition of full length TERC does not induce the same dramatic regulatory changes generated by T3p inhibition. To further strengthen these findings, a gain-of-function experiment was also performed. Using synthetic oligonucleotide as a T3p mimetic, the parental MDA-MB-231 breast cancer cells were transfected with scrambled oligonucleotide as control and then gene expression profiling was performed. Similar to the LNA experiment, a significant change in the gene expression landscape of the cell was observed. Importantly, these gene expression changes were generally anti-correlated with those observed in the loss-of-function LNA experiment (FIG. 6A). This is consistent with the expectation that anti-T3p LNAs and T3p mimetics should elicit opposite gene expression changes. Together, these observations establish T3p as a broad regulator of gene expression in breast cancer cells.

Example 5. T3p Promotes Breast Cancer Metastasis

Figure 6B:
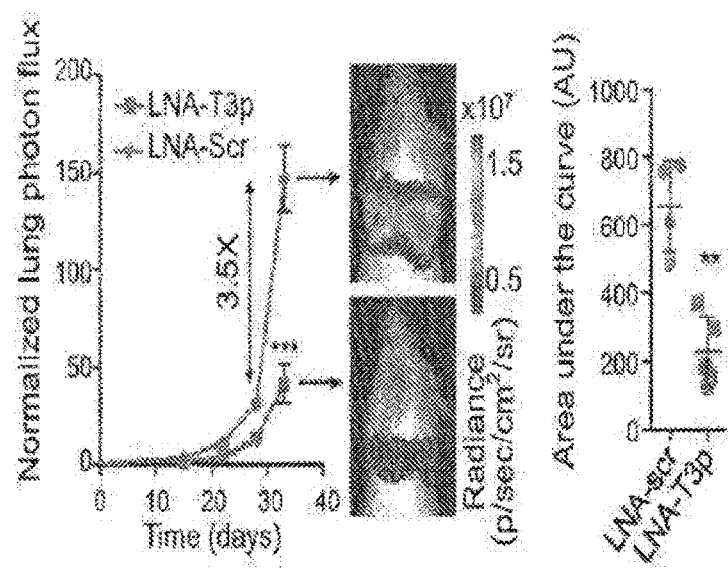
Figure 6C:
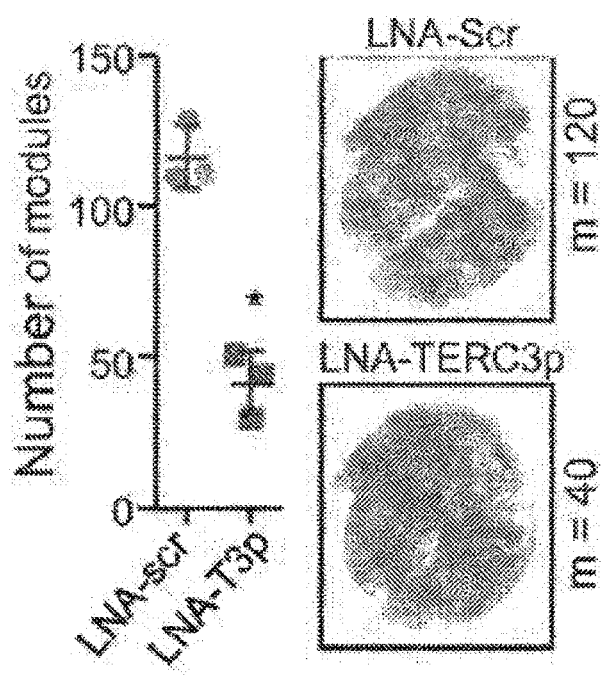

Given the broad regulatory effect on gene expression of T3p, as well as its association with metastasis and with poor survival in breast cancer, it was next tested whether this oncRNA could affect metastasis in vivo. To test this hypothesis, highly metastatic MDA-LM2 cells were transfected with anti-T3p LNAs and metastatic lung colonization assays were carried out by injecting these cells into the venous circulation of immunocompromised mice. In vivo imaging was then used to measure the impact of T3p inhibition on metastatic lung colonization of these cells over time. As shown in FIG. 6B, cells transfected with anti-T3p LNAs had significantly diminished lung colonization capacity. Gross histology of lungs from each cohort also revealed a significantly lower number of visible metastatic nodules in the lungs of mice injected with T3p-LNA transfected cells. As shown in FIG. 6C, visible metastatic nodules were counted in three mice from each cohort. Also shown are H&E stained representative lung sections from each cohort along with the median counts. These observations strongly support a functional role for T3p, a previously unknown ncRNA, in driving breast cancer metastasis.

Example 6. Specific oncRNAs are Sorted into the Exosomal Compartment

Figure 7A:
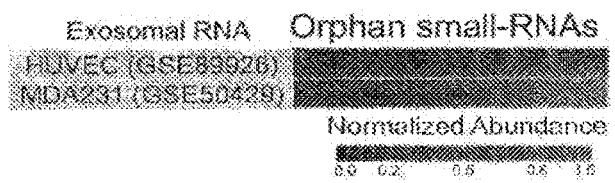
FIG. 7A-FIG. 7C shows systematic profiling of oncRNAs in the exosomal compartment.
Figure 7B:
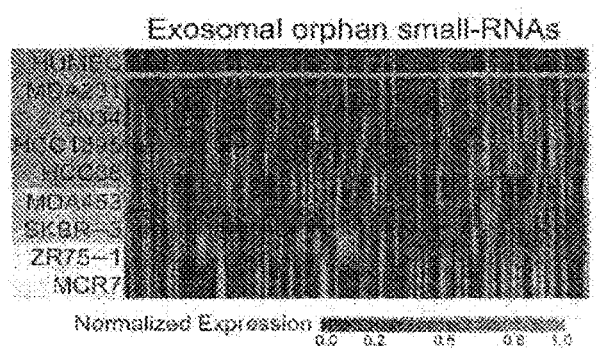
Figure 8A:
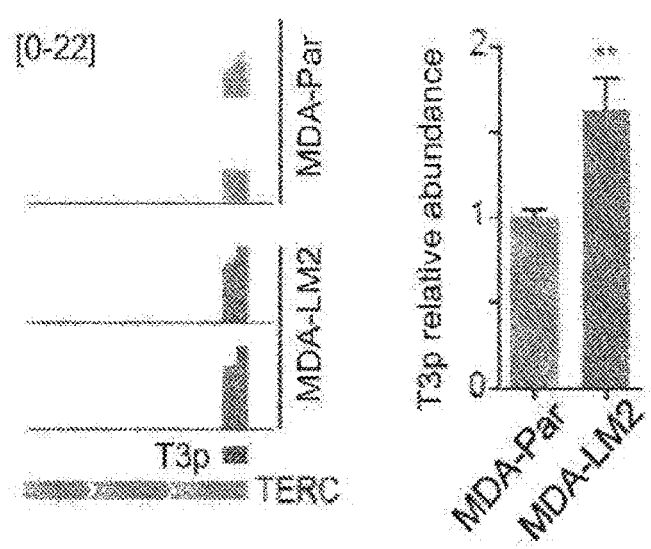
FIG. 8A and FIG. 8B show T3p can be detected in the exosomal and circulating compartments.

The exosomal compartment has been previously reported as a biologically relevant destination for small RNAs, such as small non-coding RNAs and tRNA fragments (28). Analysis of publicly available exosomal small RNA-seq data from MDA-MB-231 cells (29) revealed that a large number of annotated oncRNAs from this study can be detected in exosomes secreted from cancer cells (FIG. 7A). In comparison, only a handful of these oncRNAs were detected in exosomal samples from HUVEC cells (30). T3p, for example, was present in exosomes collected from MDA-MB-231 cells but not HUVEC cells (FIG. 8A). These observations prompted the next set of experiments aimed at profiling exosomal small RNAs. To this end, small RNA were isolated from exosomes secreted from eight breast cancer cell lines as well as from HMECs. Small RNA sequencing of this material revealed that of the 201 annotated oncRNAs, close to two thirds were detected in exosomal RNA from one or more of these breast cancer lines but not in HMECs (FIG. 7B). Interestingly, T3p was detected in 5 out of 8 cell lines.

Figure 7C:
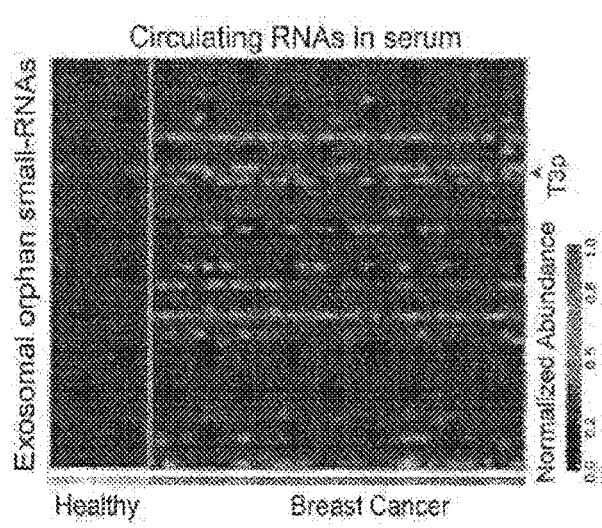
Figure 8B:
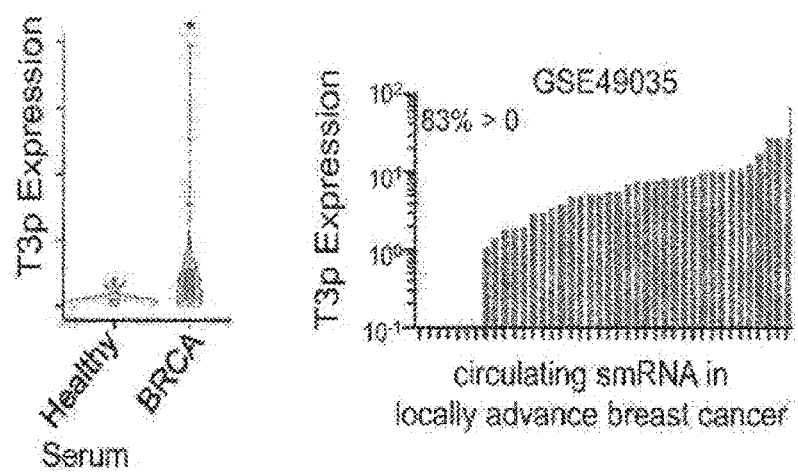
Figure 9A:
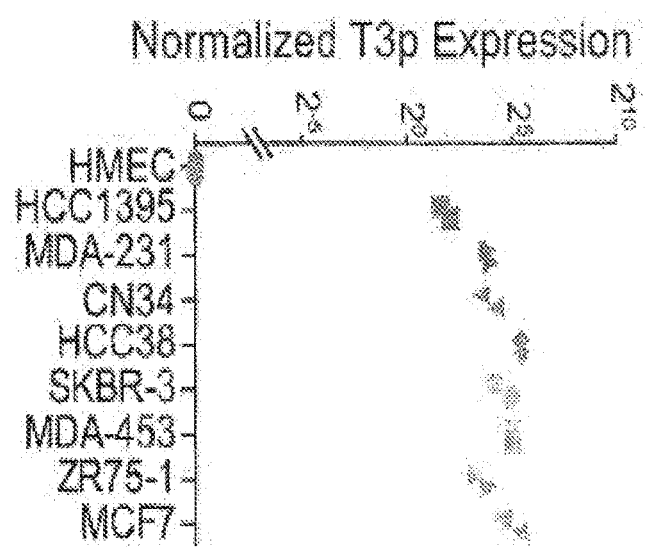
FIG. 9A through FIG. 9C show that the oncRNA T3p is associated with aggressive breast cancers.
Figure 9B:
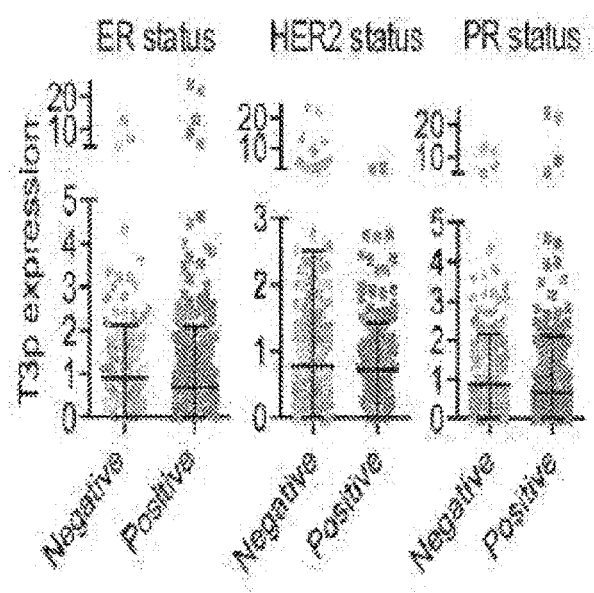
Figure 9C:
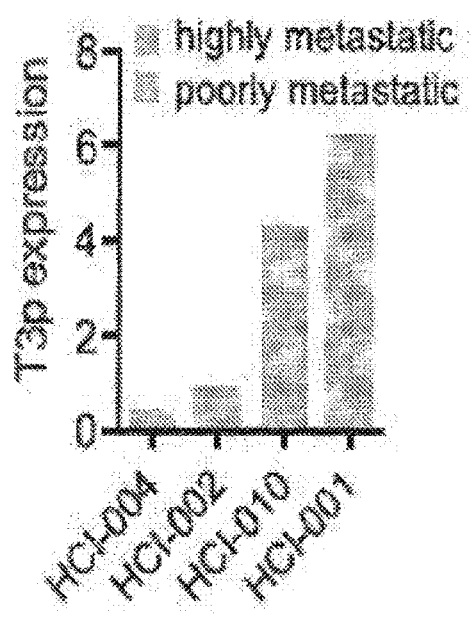
Figure 10A:
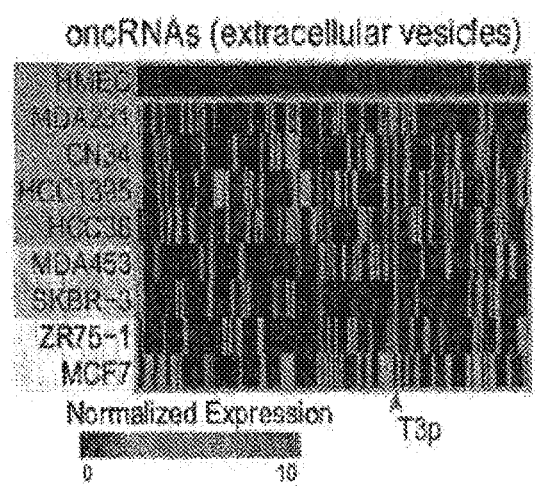
FIG. 10A through FIG. 10F show that T3p can be detected in the extracellular and circulating compartments.
Figure 10B:
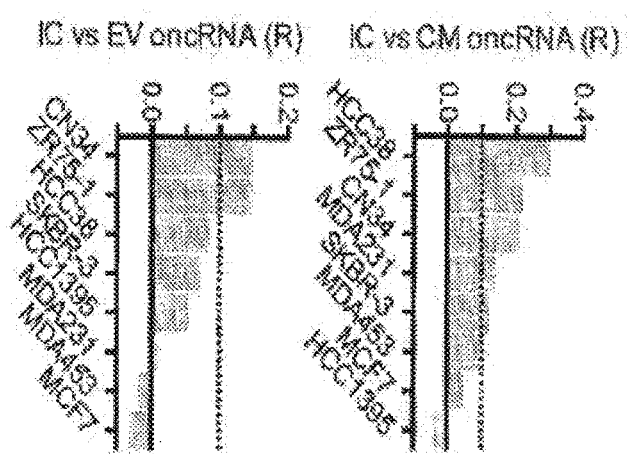
Figure 10C:
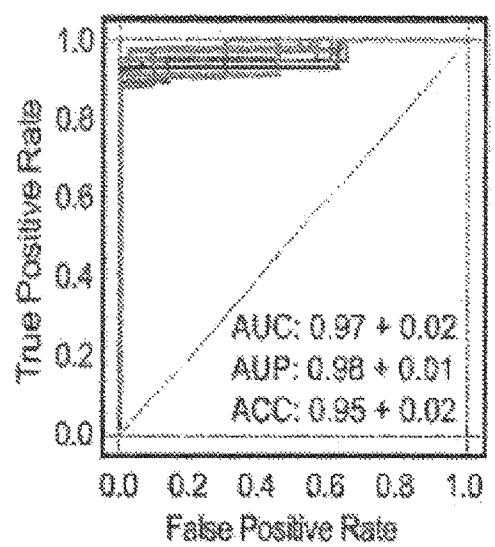
Figure 10D:
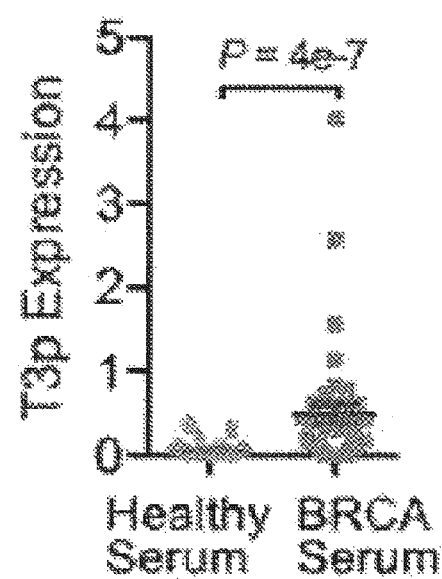
Figure 10E:
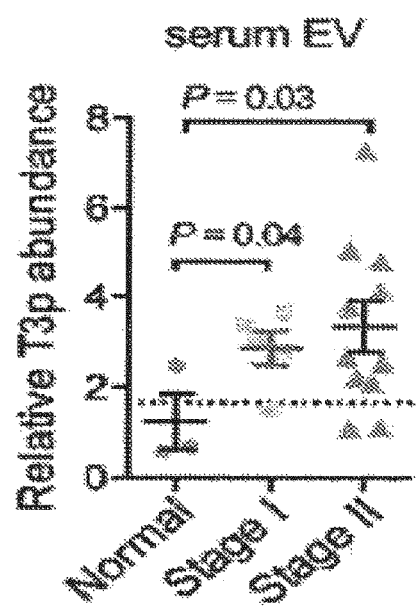
Figure 10F:
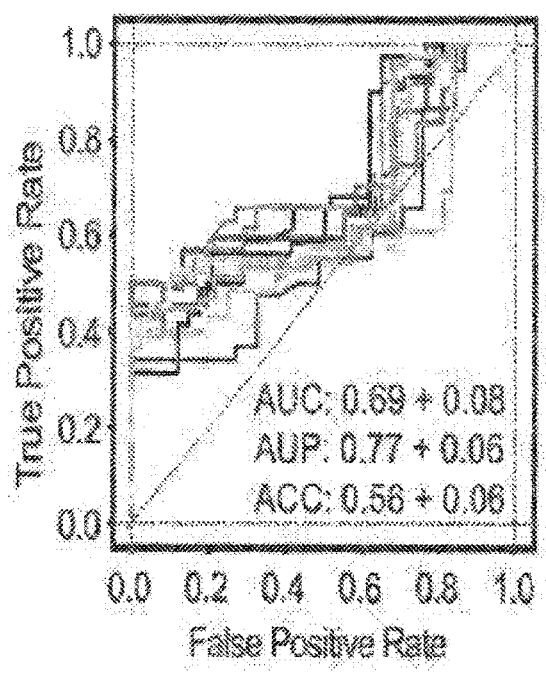

To assess whether oncRNAs are also present in the circulating RNA population, a collection of RNA-seq data generated from RNA isolated from sera from breast cancer patients was re-analyzed (31). As a point of reference, data collected from sera of 11 healthy individuals was included (32). As shown in FIG. 7C, a large fraction of oncRNAs could be detected in circulating RNA samples from breast cancer patients but were generally absent from healthy individuals. This observation raises the possibility that circulating oncRNAs can be used for cancer fingerprinting from liquid biopsies. To assess this possibility, a linear model was trained on the exosomal oncRNA dataset collected from cell lines (FIG. 7B) and used it to predict the classification of circulating RNA profiles (FIG. 7C). The trained model successfully assigned 11/11 healthy samples and 31/40 samples from cancer patients (AUC: 0.96, AUPRC: 0.99, and ACC: 0.82). For example, T3p alone showed markedly different expression levels between breast cancer patients and healthy volunteers (FIG. 7C and FIG. 8B). Given the success of this simple classifier, a more generalizable machine learning approach was tested by training a Gradient Boosted Classifier on the 201 oncRNAs in the TCGA-BRCA dataset. This model, which was trained on the TCGA data, was tested on the circulating small RNA profiles in FIG. 7C. This classifier successfully classified 11/11 healthy and 37/40 patient samples (AUC: 0.976, AUPRC: 0.993, and ACC: 0.948). Based on these results, we surmise that detection of circulating oncRNAs can be used as a robust readout for the presence of an underlying cancer with high specificity. A list of 67 circulating oncRNAs that were identified is shown in Table 2, below.

TABLE 2

| Chromosome Location | Start on chromosome | End on chromosome | OncRNA ID | Chromosome strand | Nucleotide Sequence |
|---|---|---|---|---|---|
| chr1 | 20787250 | 20787300 | tag_860 | − | GGCGGCTGGGACTGGAGGACAGCGGTGGCGGAGGC GACTAGCGGCGGCGG |
| chr1 | 28914600 | 28914650 | tag_1217 | + | GCTCGCTCGCTCCCTCCCTCCGCTGGTGCGTTTAG TCAGTCAGCCAGCAG |
| chr1 | 149888200 | 149888250 | tag_4908 | + | TCAAACAAAATACTGGTTTTGTTTTACTGAGAGGC ACTGTGGGTTTTGT |
| chr1 | 151372650 | 151372700 | tag_5001 | − | AGCGGCCTCTGACACCAGCACAGCAAACCCGCCGG GATCAAAGTGTACCA |
| chr1 | 154975050 | 154975100 | tag_5206 | + | TACTGACCACCCTCACCCATGAGGCTTTCTGGATC ATTCTCTGAACTTTA |
| chr1 | 162157100 | 162157150 | tag_5638 | + | ATGGGGCTGGCTGGTTGTGGGATCTGGAGGCATCT GGGGTTGGAATGTGA |
| chr1 | 162497850 | 162497900 | tag_5657 | + | GGCTGCTTGAAGTCCCGGGAGTCGGTGAGGCGGCT GCAGGTCCCTCCCTG |
| chr1 | 164559150 | 164559200 | tag_5733 | + | CTGTATATGTTTCTGGAGTCCTGAGCCTGAGCTAA ACAAAAGCAGGAGGC |
| chr1 | 167935950 | 167936000 | tag_5869 | − | GGTTCACAGCGGGCAGGGAAAGCCGCGGGAAGGGT ACTCCAGGCGAGAGG |
| chr1 | 174159550 | 174159600 | tag_6119 | + | TGGCGGAGCGAACGGGACCGGCCCGGCTTCAGAGC GCGAGGTGGAGGGTG |
| chr1 | 222618100 | 222618150 | tag_7990 | + | TGACCACAACATGGCTGCGGCGCCTGGGCTGCTCG TCTGGCTGCTCGTGC |
| chr1 | 228458100 | 228458150 | tag_8247 | + | GCGTTTCTGTTTGGAGAGACTCAGCCATCATGCCA GACCCGTCCAAATCG |
| chr1 | 245513450 | 245513500 | tag_8967 | − | CTGCCCTTATCAGTTTTGACCTGCTAGGTGCTTCA CAGAACTTTGCTTGA |
| chr10 | 47570550 | 47570600 | tag_10732 | + | GTGGGAGGATCACTTGAGCCCGGAAGTTCAAGACC ACCCTAGGCAATATA |
| chr10 | 89306850 | 89306900 | tag_12154 | + | ATGAATCTAAGAGAGAATGGAATGTATGGGAAAAG AAAGTTACTGGAACT |
| chr11 | 70203300 | 70203350 | tag_16694 | + | TGTCGATTTCCTGTAGTGAATCAGGCACCGGAGTG CAGGTTCGGGGGTGG |
| chr12 | 6537600 | 6537950 | tag_19454 | + | CACTGCCACCCAGAAGACTGTGGATGGCCCCTCCG GGAAACTGTGGCGTGATGGCCGCGGGGCTCTCCAG AACATCATCCCTGCCTCTACTGGCGCTGCCAAGGC TGTGGGCAAGGTCATCCCTGAGCTGAACGGGAAGC TCACTGGCATGGCCTTCCGTGTCCCCACTGCCAAC GTGTCAGTGGTGGACCTGACCTGCCGTCTAGAAAA ACCTGCCAAATATGATGACATCAAGAAGGTGGTGA AGCAGGCGTCGGAGGGCCCCCTCAAGGGCATCCTG GGCTACACTGAGCACCAGGTGGTCTCCTCTGACTT CAACAGCGACACCCACTCCTCCACCTTTGACGCTG |
| chr12 | 29394350 | 29394400 | tag_20390 | + | ACTTTTTTTTTTTTTTTAGCAGTTTGAGTTGGT GTAGTGTATTCTTGG |
| chr12 | 52899800 | 52899900 | tag_21160 | − | TATGAGGAGCTGCAGAGCCTGGCTGGGAAGCACGG GGATGACCTGCGGCGCACAAAGACTGAGATCTCTG AGATGAACCGGAACATCAGCCGGCTCCAGG |
| chr12 | 57846650 | 57846700 | tag_21447 | − | TGGACCCAAACTGAGGAGCCCGGAGCTGCCGCTGG GGGATCGGGGCCGGG |
| chr12 | 107761050 | 107761100 | tag_23158 | − | AGGGCCGGGCGGGACGGGAAACGTTAGGGCAGCGG CCCCGGGGTGAGGG |
| chr12 | 120198900 | 120198950 | tag_23669 | − | GCCAGCCCAGAACACTGGTCTCGGGCCCGAGAAGA CCTCCTTTTTCCAGG |

TABLE 2-continued

| Chromosome Location | Start on chromosome | End on chromosome | OncRNA ID | Chromosome strand | Nucleotide Sequence |
|---|---|---|---|---|---|
| chr13 | 45418300 | 45418350 | tag_25246 | − | CTTGTTACAACTGAGTCCGGGTTGGAGGAGGTGTGGGGCCGCTGCCGCCA |
| chr13 | 69167900 | 69167950 | tag_26012 | − | CCCCCACAACCGCGCCTGGCTACTTTTTGTATTTTTAGTAGAGACAGGGT |
| chr14 | 47937850 | 47937900 | tag_28594 | − | CACTCCTGACATCATCTGATAAAAGAAAGTCTTCAGCCGAATTTAATTTA |
| chr14 | 88649650 | 88649700 | tag_30094 | + | CCAAAACTATTCATTTGCATTGTAGTAGTTTGTACAGTCATATGTAAAAC |
| chr14 | 90396800 | 90396850 | tag_30143 | − | GTCGGGGAAGCGTTCTAGGCTGGGCGCGCGGTCTCGGGTCAGGTGTGGCG |
| chr15 | 62053800 | 62053850 | tag_32551 | − | TTTATCCCACTCCTGACAGTTTATCCCACTCTTGACACTTCCCCTTGAGC |
| chr15 | 69058600 | 69058650 | tag_32828 | − | ACACCAGGTCTCCTGGCCTTGCTGACTCCCAGTCCAGGGAGATGGAGGCT |
| chr16 | 2762350 | 2762600 | tag_34360 | + | CACCAGCCCGGAGGGGCAGGTCTCGGTCTAGAACACCTGCTAGGCGCAGATCTAGGACCCGATCACCAGTACGACGCAGGTCTCGTAGTAGATCACCAGCCAGGAGAAGTGGCAGGTCACGCTCTAGAACCCCAGCTAGACGTGGCCGCTCACGCTCCAGAACCCCAGCCACACCTGGCCGCTCACGCTCTAGAACCCCAGCTAGACGCAGTGGTCGCTCACGCTCCAGAACACCAGCCAGGAGAGGGAG |
| chr16 | 16144500 | 16144550 | tag_34906 | + | ATTAGAATGAGTAGTAGTGTCTGGGTGCAGTGACTCATGCCCCATTGAAA |
| chr16 | 67928900 | 67928950 | tag_36401 | + | TGCCAGGGGCACTGCCTTCTCACAGCTGGCCTTGCCCCGTCCACCCTGTG |
| chr16 | 78380500 | 78380550 | tag_36827 | + | ATTCAGCCGTATCAGTGAAGAGTGAAGCACTGCACTCTTTAAGGATAGGG |
| chr17 | 31534850 | 31534900 | tag_38643 | + | CCCTGAGCTGCCCTTGCGTTCAGTTGGAAGCCACGCAAAATGAACTGAAC |
| chr17 | 36486650 | 36486700 | tag_38844 | + | GCGTGAGAGGCGCGCGGCGGCGCAGTGAACAGTCTCCTTCCACAAAACCA |
| chr17 | 38604550 | 38604600 | tag_38922 | − | GCAGCCCTGGCAGTGCCTCCGGCGCTTTGCCCTGGCCTGGTGGGAGAGGA |
| chr17 | 58083400 | 58083450 | tag_39984 | + | CGCGCGTCGGCCGCGCTCAGCGGCAGAGCGGAGCGGAGCTGTGAGGCGCC |
| chr17 | 64919400 | 64919450 | tag_40314 | − | GCGGCTGAAGGCGATCCGCAGTGAGGCCCCAGCCATTCGGATTGAGCCTT |
| chr17 | 81133250 | 81133300 | tag_41079 | − | CTGGCCTGGCAGGTGACGGTGCTGGATGTGGCCTTTTTGCCTTTTCTAAA |
| chr18 | 797950 | 798150 | tag_41315 | − | AAGAAAATAGACAATACACTTATCTGGCTGGGGAGATACCATGATCATGAAGGTGGTTCTCAGAGTGAGGCTCATCCATTGCACTTTGGTTGTGCTGACCCCTGTGATTTCCCCAAATGCAGAATTTGTAGTAGTGAGGGACTGTGTTCGTGCTTTCCCCTGTCATTTTTTGTCCTAAGAGATCATAGTGTGAAGTTTAT |
| chr19 | 29942250 | 29942300 | tag_45203 | + | GCGGCCGCCACGCGACGCCTGGCTGGGCCCGCACCGGAGAGGCGTCTCGG |
| chr19 | 53671950 | 53672000 | tag_46359 | + | TCAGACATGACATTCAGACTGAGGTCCTCAAAACTGAGGGGCATTTTCTG |
| chr2 | 10302900 | 10302950 | tag_47066 | + | GGCAGGCGGCCGCGGCGGCGGCGGGCAGCGGACGGCGGACTGACGGGC |
| chr20 | 9068700 | 9068750 | tag_56150 | + | CGAGGCGACAGCTCGGGCTCTGGAGCCGGGAGGCGAGAACGAGGAGGAG |

TABLE 2-continued

| Chromosome Location | Start on chromosome | End on chromosome | OncRNA ID | Chromosome strand | Nucleotide Sequence |
|---|---|---|---|---|---|
| chr20 | 25390750 | 25390800 | tag_56729 | - | TTCCGGGCTCCGGGCTCTGGGTGGCGGCGGCTGTGAGCGGCGGCACTGCG |
| chr20 | 35765850 | 35765900 | tag_57047 | + | CAGTCTGAGATCAGTCTGGGCCACATAGCGACACCCCGTCTCTATGTTAA |
| chr20 | 36870700 | 36870750 | Tag_57094 | + | GTTCAAGACCAGCCTTGGCAATATAGCGAGACCCCGTCTCTACAAAACA |
| chr20 | 58448250 | 58448350 | tag_58054 | + | AACACCAAGAGCAGCTCTGAGATCATGCTGGCCCTACGCGAATTGAGTTTCTGTGGCCTAATTGGATTTGGAGAACGCCTTCCCTGGCCCCTTTTCCTCA |
| chr3 | 47266450 | 47266500 | tag_62984 | + | CTTGGCAACATAGCGAGACCCCGTCTCTACAAAAAAATTTAAAAATTAGC |
| chr3 | 169764600 | 169764650 | tag_67280 | - | TGAGCTGTGGGACGTGCACCCAGGACTCGGCTCACACATGCAGTTCGCTT |
| chr3 | 195658050 | 195658100 | tag_68250 | + | CAGTCTGCGCAGGGACTGGCGGGACTGCGCGGCGGCGACTACAGACGTGT |
| chr4 | 81382050 | 81382100 | tag_71049 | + | AAAATGCCTATTTAAATTACTATTTCATTATTTTTCTCAAAAGTGTGAAA |
| chr4 | 140152300 | 140152350 | tag_72898 | + | TGGGGAGAGGAGGCGAGAGGCTCTCCTTCCCCGCTTCCCCCCTAGGGGTT |
| chr4 | 145186850 | 145186900 | tag_73067 | + | GACTGCAGTCCTGAGACCCTATAACCTGTATGACTAGAGAAGTGAAACTA |
| chr4 | 173268150 | 173268200 | tag_74031 | + | AAAAATGTTAGGGTGGTCAAAAGTGATCGTGGTTTTTGCAATTTTTTAA |
| chr5 | 14001200 | 14001250 | tag_75126 | - | TATTGTGGGATACTGAGGCTTGGAGTGTGAATGAATCCTTCACCCAGGTA |
| chr5 | 173888350 | 173888400 | tag_80583 | + | TCGGCTCGGTCCTGAGGAGAAGGACTCAGCCGCGGCTGCGGGACCCGGGC |
| chr6 | 127266850 | 127266900 | tag_85800 | + | GCGCGTTCCCGGCAGCTGCGGGCTCCGAGGCCAGAGAGAAAAGACTGCGA |
| chr6 | 166956500 | 166956550 | tag_87323 | - | GAGCAACGCGACTGACCGTGGTCGTGGGCGGACGGCGGCTGCAGCGTGGA |
| chr7 | 6059100 | 6059200 | tag_87724 | - | CTGGTTTTCCGTCTGGTGAGGGGTTACTTCCGGGTCGGACGGCGCTAGCTGCAGCATCGGAGTGTGGCAGTGCTGGGCTGGCCGGCGGGCTGGGCTGCGG |
| chr7 | 157410800 | 157410950 | tag_93308 | + | GGTTACTTCTGTGGACTTGGGCCGAACAGCACTGTCTAAGCAGGACATGAAAAGAAGGGGGAAGCGTCTCTCCTTTTCCCTTCATGGAACTTTCCATTGAAAAATTAGCCCCTTCCAGTCCTTCTCGGATGAAGCACAGTTGCCGGTTAC |
| chr8 | 143859850 | 143859950 | tag_98647 | - | TGCTGTCGGCCGAGCGCGCCGTCACCGGCTACACCGACCCCTACACCGGGCAGCAGATCTCCCTCTTCCAGGCCATGCAGAAGGACCTCATCGTCCGGGA |
| chr8 | 143868300 | 143868400 | tag_98658 | - | GGAGAACCGGAAGCTGACCGTGGAGGAGGCGTTCAAGCAGGAATGTTCGGGAAAGAAACCTACGTGAAGCTGCTGTCGGCCGAGCGCGCCGTCACCGGC |
| chr8 | 144789800 | 144789900 | tag_98753 | - | CAGAGATGCCCCTGCTGGCCGCAAAGTGGGTCTCATTGCTGCCCGCCGGACTGGACGTCTCCGGGGAACCAAGACTGTGCAGGAGAAAGAGAACTAGTGC |
| chr9 | 123110200 | 123110250 | tag_102264 | - | TGTAGTGGTCCTGCAGGAGTGGAGCCTGTAGGACTTGCTTCTCAGCGGCT |
| chr9 | 123111550 | 123111600 | tag_102265 | - | TGTCAGGCAGTGGAGTTACTTACAGACAAGAGCCTTGCTCAGGCCAGCCC |

TABLE 2-continued

| Chromosome Location | Start on chromosome | End on chromosome | OncRNA ID | Chromosome strand | Nucleotide Sequence |
|---|---|---|---|---|---|
| chrX | 152393300 | 152393500 | tag_107993 | − | ACCATGGTTGTCTGAGCATGCAGCATGCTTGTCTG CTCATACCCCArGGTTTCTGAGCAGGAACCTTCAT TGTCTACTGCTTTACAGGGAAATAGTGTTTTATGC ATCGTGTATATGAGTTTAGTATTTACTCATATTCT ATGACTCTCTACTCTTAGATCACTTCTGCCTTTTT CTGCACATTGTTTATCTGTTCCAAA |

Finally, from the 201 oncRNAs identified, the following oncRNAs shown in Table 3 were found to be the strongest performers in predicting the presence of breast cancer in a subject through analysis of serum samples.

TABLE 3

| Chromosome Location | Start on Chromosome | End on Chromosome | OncRNA ID | Chromosome strand | Nucleotide Sequence | Sequence Identifier |
|---|---|---|---|---|---|---|
| chr1 | 20787250 | 20787300 | tag_860 | − | GGCGGCTGGGACTGGAGGAC AGCGGTGGCGGAGGCGACTA GCGGCGGCGG | SEQ ID NO: 3 |
| chr1 | 174159550 | 174159600 | tag_6119 | + | TGGCGGAGCGAACGGGACCG GCCCGGCTTCAGAGCGCGAG GTGGAGGGTG | SEQ ID NO: 19 |
| chr10 | 89306850 | 89306900 | tag_12154 | + | ATGAATCTAAGAGAGAATGG AATGTATGGGAAAAGAAAGT TACTGGAACT | SEQ ID NO: 32 |
| chr12 | 29394350 | 29394400 | tag_20390 | + | ACTTTTTTTTTTTTTTTA GCAGTTTGAGTTGGTGTAGT GTATTCTTGG | SEQ ID NO: 40 |
| chr12 | 52899800 | 52899900 | tag_21160 | − | TATGAGGAGCTGCAGAGCCT GGCTGGGAAGCACGGGGATG ACCTGCGGCGCACAAAGACT GAGATCTCTGAGATGAACCG GAACATCAGCCGGCTCCAGG | SEQ ID NO: 41 |
| chr16 | 78380500 | 78380550 | tag_36827 | + | ATTCAGCCGTATCAGTGAAG AGTGAAGCACTGCACTCTTT AAGGATAGGG | SEQ ID NO: 79 |
| chr17 | 31534850 | 31534900 | tag_38643 | + | CCCTGAGCTGCCCTTGCGTTC AGTTGGAAGCCACGCAAAAT GAACTGAAC | SEQ ID NO: 82 |
| chr17 | 36486650 | 36486700 | tag_38844 | + | GCGTGAGAGGCGCGCGGCGG CGCAGTGAACAGTCTCCTTC CACAAAACCA | SEQ ID NO: 83 |
| chr20 | 58448250 | 58448350 | tag_58054 | + | AACACCAAGAGCAGCTCTGA GATCATGCTGGCCCTACGCG AATTGAGTTTCTGTGGCCTA ATTGGATTTGGAGAACGCCT TCCCTGGCCCCTTTTCCTCA | SEQ ID NO: 126 |
| chr4 | 173268150 | 173268200 | tag_74031 | + | AAAAATGTTAGGGTGGTGCA AAAGTGATCGTGGTTTTTGC AATTTTTTAA | SEQ ID NO: 148 |
| chr9 | 123110200 | 123110250 | tag_102264 | − | TGTAGTGGTCCTGCAGGAGT GGAGCCTGTAGGACTTGCTT CTCAGCGGCT | SEQ ID NO: 191 |

The current hypothesis of breast cancer development and progression emphasizes the transformation of aberrant cell machinery leading to increased selection for oncogenic phenotypes. Consequently, the development of cancer therapy and diagnostics aims to target these pathways to reduce the ability of these cancer cells to survive, divide, or spread. In the present examples, it was proposed that cancer cells may also evolve to create cancer-specific regulatory pathways. Through a systematic and unbiased discovery step across eight breast cancer cell lines and HUMECs combined with clinical breast cancer data, a population of 201 RNA species that are expressed in breast cancer cells, but are largely undetectable in normal tissue, have been identified. These RNA molecules, which have collectively been named orphan non-coding RNAs, provide a pool of novel potential regulators that cancer cells can utilize to engineer new regulatory circuits. Poorly and highly metastatic cells were compared to ask whether oncRNAs can function in breast cancer progression. It was discovered that one of these RNAs, which was termed T3p, is strongly associated with metastatic progression in both cell line models and clinical datasets. Finally, the examples described herein show that oncRNAs can be detected in circulating and exosomal compartments.

These findings offer a new paradigm for cancer progression and how tumors can evolve and rewire regulatory pathways en route to metastatic spread. Moreover, these results also suggest a novel avenue for breast cancer detection and monitoring that could complement current methods. Current screening methods for breast cancer, including mammography and ultrasounds, offer limited detection signals due to low resolution, and are biased given their reliance on user interpretation. Other strategies in development for detecting early cancer have focused on "liquid biopsies," which attempt to detect cancer biologic markers, including circulating tumor cells and DNA, from a patient's serum. The higher abundance of secreted exosomes within patient serum and the cancer cell specificity of oncRNA may provide a potent addition to our repertoire for a more reliable method of early detection or screening. In other words, the work described herein supports the notion that oncRNAs act as a digital fingerprint—i.e., each marker is detected or not detected—for the underlying tumors.

Although the examples described herein have largely focused on the role of T3p in breast cancer metastasis, the approaches and concepts presented here are generalizable and can be applied across several cancers. Taken together, these findings open the possibility that further examination of the cancer-specific RNA landscape and investigation into oncRNAs may yield alternative therapeutic and diagnostic methods across many cancer types.

REFERENCES

1 S. F. Tavazoie et al., Endogenous human microRNAs that suppress breast cancer metastasis. Nature. 451, 147-U3 (2008).
2. C. J. David, M. Chen, M. Assanah, P. Canoll, J. L. Manley, HnRNP proteins controlled by c-Myc deregulate pyruvate kinase mRNA splicing in cancer. Nature. 463, 364-368 (2010).
3. S. Vanharanta et al., Loss of the multifunctional RNA-binding protein RBM47 as a source of selectable metastatic traits in breast cancer. eLife. 3 (2014), doi: 10.7554/eLife.02734.
4. L. Fish et al., Muscleblind-like 1 suppresses breast cancer metastatic colonization and stabilizes metastasis suppressor transcripts. Genes Dev. 30, 386-398 (2016).
5. L.-Y. Chen, J. Lingner, AUF1/HnRNP D RNA binding protein functions in telomere maintenance. Mol. Cell. 47, 1-2 (2012).
6. H. Goodarzi et al., Modulated expression of specific tRNAs drives gene expression and cancer progression. Cell. 165, 1416-1427 (2016).
7. H. Goodarzi et al., Endogenous tRNA-Derived Fragments Suppress Breast Cancer Progression via YBX1 Displacement. Cell. 161, 790-802 (2015).
8. D. K. Simanshu, D. V. Nissley, F. McCormick, RAS Proteins and Their Regulators in Human Disease. Cell. 170, 17-33 (2017).
9. R. Ren, Mechanisms of BCR-ABL in the pathogenesis of chronic myelogenous leukaemia. Nat. Rev. Cancer. 5, 172-183 (2005).
10. R.-K. Lin, Y.-C. Wang, Dysregulated transcriptional and post-translational control of DNA methyltransferases in cancer. Cell Biosci. 4, 46 (2014).
11. A. A. Alizadeh et al., Toward understanding and exploiting tumor heterogeneity. Nat. Med. 21, 846-853 (2015).
12. A. Nguyen, M. Yoshida, H. Goodarzi, S. F. Tavazoie, Highly variable cancer subpopulations that exhibit enhanced transcriptome variability and metastatic fitness. Nat. Commun. 7, 11246 (2016).
13. R. J. Taft, K. C. Pang, T. R. Mercer, M. Dinger, J. S. Mattick, Non-coding RNAs: Regulators of disease. J. Pathol. 220 (2010), pp. 126-139.
14. M. Esteller, Non-coding RNAs in human disease. Nat. Rev. Genet. 12, 861-874 (2011).
15. A. J. Minn et al., Distinct organ-specific metastatic potential of individual breast cancer cells and primary tumors. J. Clin. Invest. 115, 44-55 (2005).
16. J. M. Loo et al., Extracellular Metabolic Energetics Can Promote Cancer Progression. Cell. 160, 393-406 (2015).
17. D. N. Cooper, L. P. Berg, V. V Kakkar, J. Reiss, Ectopic (illegitimate) transcription: new possibilities for the analysis and diagnosis of human genetic disease. Ann. Med. 26, 9-14 (1994).
18. A. A. Margolin et al., ARACNE: An Algorithm for the Reconstruction of Gene Regulatory Networks in a Mammalian Cellular Context. BMC Bioinformatics. 7, S7 (2006).
19. H. Goodarzi et al., Metastasis-suppressor transcript destabilization through TARBP2 binding of mRNA hairpins. Nature (2014), doi: 10.1038/nature13466.
20. B. Kim, K. Jeong, V. N. Kim, Genome-wide Mapping of DROSHA Cleavage Sites on Primary MicroRNAs and Noncanonical Substrates. Mol. Cell. 66, 258-269.e5 (2017).
21. D. Ray et al., A compendium of RNA-binding motifs for decoding gene regulation. Nature. 499, 172-177 (2013).
22. Y.-C. T. Yang et al., CLIPdb: a CLIP-seq database for protein-RNA interactions. BMC Genomics. 16, 51 (2015).
23. E. L. Van Nostrand et al., Robust transcriptome-wide discovery of RNA-binding protein binding sites with enhanced CLIP (eCLIP). Nat. Methods. 13, 508-514 (2016).
24. H. Goodarzi et al., Systematic discovery of structural elements governing stability of mammalian messenger RNAs. Nature. 485, 264-268 (2012).
25. S. Memczak et al., Circular RNAs are a large class of animal RNAs with regulatory potency. Nature. 495, 333-8 (2013).

26. P. Sumazin et al., An extensive microRNA-mediated network of RNA-RNA interactions regulates established oncogenic pathways in glioblastoma. Cell. 147, 370-381 (2011).
27. A. Helwak, G. Kudla, T. Dudnakova, D. Tollervey, Mapping the human small non-coding RNA interactome by CLASH reveals frequent noncanonical binding. Cell. 153, 654-65 (2013).
28. T. Fiskaa et al., Distinct Small RNA Signatures in Extracellular Vesicles Derived from Breast Cancer Cell Lines. PLOS ONE. 11 (2016), doi: 10.1371/journal.pone.0161824.
29. W. Zhou et al., Cancer-secreted miR-105 destroys vascular endothelial barriers to promote metastasis. Cancer Cell. 25, 501-515 (2014).
30. S. K. Chakrabortty, A. Prakash, G. Nechooshtan, S. Hearn, T. R. Gingeras, Extracellular vesicle-mediated transfer of processed and functional RNY5 RNA. RNA N. Y. N. 21, 1966-1979 (2015).
31. X. Wu et al., De novo sequencing of circulating small non-coding RNAs identifies novel markers predicting clinical outcome of locally advanced breast cancer. J. Transl. Med. 10, 42-42 (2012).
32. M. D. Giraldez et al., Accuracy, Reproducibility And Bias Of Next Generation Sequencing For Quantitative Small RNA Profiling: A Multiple Protocol Study Across Multiple Laboratories. bioRxiv, 113050 (2017).
33. O. Elemento, N. Slonim, S. Tavazoie, A universal framework for regulatory element discovery across all Genomes and data types. Mol. Cell. 28, 337-350 (2007).

---

The invention claimed is:

1. A method for sequencing a non-coding ribonucleic acid (RNA) molecule from a cell-free sample obtained from a human female subject, comprising:
   (a) providing the cell-free sample from the human female subject, wherein the cell-free sample comprises a first set of non-coding RNA molecules;
   (b) subjecting the first set of non-coding RNA molecules to reverse transcription to generate one or more complementary deoxyribonucleic acid (cDNA) molecules;
   (c) sequencing the one or more cDNA molecules or derivatives thereof; and
   (d) based on the sequencing in (c), determining whether the first set of non-coding RNA molecules contains one or more non-coding RNA molecules of a second set of non-coding RNA molecules, wherein the second set of non-coding RNA molecules are present in breast tumor samples, and wherein the second set of non-coding RNA molecules have a $90^{th}$ percentile expression in normal samples below 0.5 cpm (count-per-million) reads.

2. The method of claim 1, wherein the non-coding RNA molecule has a length of less than 200 nucleotides.

3. The method of claim 1, wherein the non-coding RNA molecule has a length between 50 and 100 nucleotides.

4. The method of claim 1, further comprising, after (b), amplifying a cDNA molecule of the one or more cDNA molecules.

5. The method of claim 1, further comprising, after (a), isolating the first set of non-coding RNA molecules from other components of the cell-free sample.

6. The method of claim 5, wherein the isolating comprises filtration.

7. The method of claim 1, further comprising using a result of the sequencing to determine an amount of a non-coding sequence of a non-coding RNA molecule of the first set of non-coding RNA molecules in the cell-free sample.

8. The method of claim 1, wherein the cell-free sample comprises serum.

9. The method of claim 1, wherein the cell-free sample comprises plasma.

10. The method of claim 1, wherein the cell-free sample comprises urine.

11. The method of claim 1, wherein the cell-free sample comprises lymph.

12. The method of claim 1, wherein the cell-free sample comprises saliva.

13. The method of claim 1, wherein a total volume of the cell-free sample is between 20 microliters and 2 milliliters.

14. The method of claim 1, wherein a total volume of the cell-free sample is between 100 microliters to 500 microliters.

15. The method of claim 1, wherein the cell-free sample comprises plasma, and wherein a total volume of the cell-free sample is between 100 microliters and 1 milliliter.

16. The method of claim 1, wherein the sequencing in (c) generates sequencing reads, and wherein the sequencing reads are processed to identify a non-coding sequence of a non-coding RNA molecule of the first set of non-coding RNA molecules.

17. The method of claim 1, wherein the sequencing in (c) comprises sequencing-by-synthesis.

18. The method of claim 1, wherein the normal samples are from subjects who do not have breast cancer.

19. The method of claim 4, wherein the amplifying comprises performing a polymerase chain reaction (PCR).

20. The method of claim 4, wherein the amplifying comprises rolling circle amplification.

* * * * *